US008911722B2

(12) United States Patent
Bellgrau et al.

(10) Patent No.: US 8,911,722 B2
(45) Date of Patent: Dec. 16, 2014

(54) MODULATION OF YEAST-BASED IMMUNOTHERAPY PRODUCTS AND RESPONSES

(75) Inventors: Donald Bellgrau, Highlands Ranch, CO (US); Beth Tamburini, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 13/395,965

(22) PCT Filed: Sep. 14, 2010

(86) PCT No.: PCT/US2010/048699
§ 371 (c)(1),
(2), (4) Date: May 24, 2012

(87) PCT Pub. No.: WO2011/032119
PCT Pub. Date: Mar. 17, 2011

(65) Prior Publication Data

US 2012/0321664 A1 Dec. 20, 2012

Related U.S. Application Data

(60) Provisional application No. 61/242,355, filed on Sep. 14, 2009, provisional application No. 61/242,353, filed on Sep. 14, 2009, provisional application No. 61/288,568, filed on Dec. 21, 2009.

(51) Int. Cl.

| | |
|---|---|
| ***A61K 39/39*** | (2006.01) |
| *A61K 39/395* | (2006.01) |
| *A61K 36/06* | (2006.01) |
| *C12Q 1/02* | (2006.01) |
| *A61K 39/00* | (2006.01) |

(52) U.S. Cl.
CPC ..... *A61K 39/39541* (2013.01); *A61K 2039/523* (2013.01); *A61K 2039/57* (2013.01); *A61K 2039/505* (2013.01)
USPC .................... 424/93.51; 424/93.1; 424/184.1; 424/192.1; 435/29

(58) Field of Classification Search
None
See application file for complete search history.

(56) References Cited

U.S. PATENT DOCUMENTS

| | | | |
|---|---|---|---|
| 4,775,622 | A | 10/1988 | Hitzeman et al. |
| 5,234,830 | A | 8/1993 | Oshima et al. |
| 5,310,654 | A | 5/1994 | Isberg et al. |
| 5,413,914 | A | 5/1995 | Franzusoff |
| 5,830,463 | A | 11/1998 | Duke et al. |
| 5,858,378 | A | 1/1999 | Bostwick |
| 5,919,651 | A | 7/1999 | Hitzeman et al. |
| 7,083,787 | B2 | 8/2006 | Duke et al. |
| 7,439,042 | B2 | 10/2008 | Duke et al. |
| 7,465,454 | B2 | 12/2008 | Franzusoff et al. |
| 7,563,447 | B2 | 7/2009 | Franzusoff et al. |
| 7,595,060 | B2 | 9/2009 | Duke et al. |
| 7,625,569 | B2 | 12/2009 | Duke et al. |
| 7,632,511 | B2 | 12/2009 | Duke et al. |
| 2002/0044948 | A1 | 4/2002 | Khleif et al. |
| 2003/0035810 | A1 | 2/2003 | Caplan |
| 2007/0172503 | A1 | 7/2007 | Selitrennikoff et al. |
| 2007/0224208 | A1 | 9/2007 | Guo et al. |
| 2008/0003239 | A1 | 1/2008 | Duke et al. |
| 2009/0074805 | A1 | 3/2009 | Duke et al. |
| 2009/0098154 | A1 | 4/2009 | Franzusoff et al. |
| 2009/0142366 | A1 | 6/2009 | Franzusoff et al. |
| 2009/0142367 | A1 | 6/2009 | Franzusoff et al. |
| 2009/0304741 | A1 | 12/2009 | Duke et al. |
| 2010/0034840 | A1 | 2/2010 | Apelian et al. |
| 2010/0104604 | A1 | 4/2010 | Selitrennikoff et al. |
| 2010/0111912 | A1 | 5/2010 | Apelian et al. |
| 2010/0150963 | A1 | 6/2010 | Duke et al. |
| 2010/0189749 | A1 | 7/2010 | Franzusoff et al. |
| 2010/0196411 | A1 | 8/2010 | Duke et al. |
| 2010/0215678 | A1 | 8/2010 | Guo et al. |
| 2011/0150909 | A1 | 6/2011 | Franzusoff et al. |
| 2011/0256098 | A1 | 10/2011 | Apelian et al. |
| 2012/0107347 | A1 | 5/2012 | Hodge et al. |

FOREIGN PATENT DOCUMENTS

| | | | |
|---|---|---|---|
| EP | 0414404 | | 2/1991 |
| EP | 2096438 | | 9/2009 |
| FR | 2486400 | | 1/1982 |
| JP | 2006-510718 | | 3/2006 |
| JP | 2008-516610 | | 5/2008 |
| WO | WO 2006/044923 | * | 4/2006 |
| WO | WO 2007/130493 | | 11/2007 |
| WO | WO 2008/115610 | | 9/2008 |
| WO | WO 2010/065626 | | 6/2010 |
| WO | WO 2011/115914 | | 9/2011 |
| WO | WO 2012/019127 | | 2/2012 |
| WO | WO 2012/083302 | | 6/2012 |

OTHER PUBLICATIONS

Wansley et al., Clinical Cancer Research, Jul. 1, 2008. vol. 14, Issue 13.*

Karayiannis et al, British Medical Bulletin 2004; vol. 70, pp. 29-49.*

Van de Veerdonk et al, BMB Reports, Dec. 2009, vol. 42, No. 12, pp. 776-787.*

Acosta-Rodriguez et al. "Surface phenotype and antigenic specificity of human interleukin 17-producing T helper memory cells," Nature Immunology, Jun. 2007, vol. 8, No. 6, pp. 639-646.

Backer et al. "CD8—dendritic cells preferentially cross-present *Saccharomyces cerevisiae* antigens," European Journal of Immunology, Feb. 2008, vol. 38, No. 2, pp. 370-380.

Barron et al. "Human Dendritic Cell Interactions with Whole Recombinant Yeast: Implications for HIV-1 Vaccine Development," Journal of Clinical Immunology, May 2006, vol. 26, No. 3, pp. 251-264, XP019400134.

(Continued)

*Primary Examiner* — Elizabeth C Kemmerer
*Assistant Examiner* — Fozia Hamud
(74) *Attorney, Agent, or Firm* — Sheridan Ross P.C.

(57) ABSTRACT

Disclosed are methods to modulate yeast-based immunotherapy products and the immune responses, prophylactic responses, and/or therapeutic responses elicited by such products. Also disclosed are modified yeast-based immunotherapy products, kits and compositions.

12 Claims, 14 Drawing Sheets

(56) References Cited

OTHER PUBLICATIONS

Bizzini et al. "Use of live *Saccharomyces cerevisiae* cells as a biological response modifier in experimental infections," FEMS Microbiology Immunology, 1990, vol. 64, pp. 155-168.

Brake et al. "alpha-Factor-directed synthesis and secretion of mature foreign proteins in *Saccharomyces cerevisiae,*" Proceedings of the National Academy of Sciences USA, Aug. 1984, vol. 81, pp. 4642-4646.

Brown et al. "Dectin-1 Mediates the Biological Effects of b-Glucans," The Journal of Experimental Medicine, May 2003, vol. 197, No. 9, pp. 1119-1124.

Dennehy et al. "Reciprocal regulation of IL-23 and IL-12 following co-activation of Dectin-1 and TLR signaling pathways," European Journal of Immunology, May 2009, vol. 39, No. 5, pp. 1379-1386, XP007915687.

Eto et al., "Immunization with recombinant *Escherichia coli* expressing retinal S-antigen-induced experimental autoimmune uveitis (EAU) in Lewis rats", Cellular Immunology, vol. 147, No. 1 Mar. 1993, pp. 203-214.

Ferwerda et al. "The role of Toll-like receptors and C-type lectins for vaccination against *Candida albicans,*" Vaccine, Jan. 2010, vol. 28, No. 3, pp. 614-622.

Ferwerda et al. "Human Dectin-1 Deficiency and Mucocutaneous Fungal Infections," The New England Journal of Medicine,Oct. 2009, vol. 361, No. 18, pp. 1760-1767.

Franzusoff, A. et al. "Yeasts Encoding Tumour Antigens in Cancer Immunotherapy," Expert Opinion on Biological Therapy, Apr. 2005, vol. 5, No. 4, pp. 565-575.

Franzusoff et al. "Biochemical and Genetic Definition of the Cellular Protease Required for HIV-1 gp160 Processing," The Journal of Biological Chemistry, Feb. 1995, vol. 270, No. 7, pp. 3154-3159.

Fujita et al. "Studies in the development of Japanese encephalitis vaccine: expression of virus envelope glycoprotein V3 (E) gene in yeast," Bulletin of the World Health Organization, Feb. 1987, vol. 65, No. 3, pp. 303-308.

Gantner et al. "Dectin-1_mediates macrophage recognition of *Candida albicans* yeast but not filaments," The EMBO Journal, Feb. 2005, Vo. 24, No. 6, pp. 1277-1286.

Gerosa et al. "Differential regulation of interleukin 12 and interleukin 23 production in human dendritic cells," The Journal of Experimental Medicine, Jun. 2008, vol. 205, No. 6, pp. 1447-1461.

Holland et al. "Yeast Infections—Human Genetics on the Rise," The New England Journal of Medicine, Oct. 2009, vol. 361, No. 18, pp. 1798-1801.

Huang et al. "Distinct Patterns of Dendritic Cell Cytokine Release Stimulated by Fungal beta-Glucans and Toll-Like Receptor Agonists," Infection and Immunity, May 2009, vol. 77, No. 5, pp. 1774-1781, XP007915686.

Iezzi et al. "CD40-CD40L cross-talk integrates strong antigenic signals and microbial stimuli to induce development of IL-17-producing CD4+ T cells." Proceedings of the National Academy of Sciences of the U.S.A, Jan. 2009, vol. 106, No. 3, pp. 876-881, XP007915728.

Klepfer et al. "Characterization of rabies glycoprotein expressed in yeast," Archives of Virology, 1993, vol. 128, pp. 269-286.

Korn et al. "IL-17 and Th17 Cells," Annual Review of Immunology, 2009, vol. 27, pp. 485-517.

LAM et al. "A model vaccine exploiting fungal mannosylation to increase antigen immunogenicity," Journal of Immunology, Dec. 2005, vol. 175, No. 11, pp. 7496-7503, XP002481100.

Leibundgut-Landmann et al. "Syk-and CARD9-dependent coupling of innate immunity to the induction of T helper cells that produce interleukin 17," Nature Immunology, Jun. 2007, vol. 8, No. 6, pp. 630-638, XP007915737.

Levitz "Th17 Cells Bounce off the Fungal Wall," Cell Host & Mircrobe, Apr. 2009, vol. 5, pp. 311-313.

Lu, et al., "Mutation-Selective Tumor Remission with Ras-Targeted, Whole Yeast-Based Immunotherapy," Cancer Research, 2004, vol. 64, pp. 5084-5088.

Lyakh et al. "Regulation of interleukin-12/interleukin-23 production and the T-helper 17 response in humans," Immunological Reviews, Dec. 2008, vol. 226, pp. 112-131, XP007915672.

Miossec et al. "Interleukin-17 and Type 17 Helper T Cells," The New England Journal of Medicine, Aug. 2009, vol. 361, No. 9, pp. 888-898.

Moore et al., "Novel yeast-based vaccine 1-40, against HIV-SF2 gp160 promotes a cytotoxic 43-62 cell response.", FASEB Journal (online), vol. 10. No. 6. 1996, p. A1473, ZP002186594, Joint Meeting of the American Society for Biochemistry and Molecular Biology, the American Society for Investigative Pathology and the American Association of Immunologists; New Orleans, LA, USA; Jun. 2-6, 1996.

Munson et al. "Coupling innate and adaptive immunity with yeast-based cancer immunotherapy," Cancer Vaccines and Tumor Immunity, Chapter 9, Mar. 2008, pp. 131-149, XP007915738.

Osorio et al. "DC activated via dectin-1 convert Treg into IL-17 producers." European Journal of Immunology, Dec. 2008, vol. 38, No. 12, pp. 3274-3281, XP007915724.

Parrish-Novak et al. "Interleukin-21 and the IL-21 receptor: novel effectors of NK and T cell responses," Journal of Leukocyte Biology, Nov. 2002, vol. 72, pp. 856-863.

Plantinga et al. "Early Stop Polymorphism in Human Dectin-1 Is Associated with Increased *Candida* Colonization in Hematopoietic Stem Cell Transplant Recipients," Clinical Infections Diseases, Sep. 2009, vol. 49, pp. 724-732.

Re et al. "Heterogeneity of TLR-induced responses in dendritic cells: from innate to adaptive immunity," Immunobiology, Aug. 2004, vol. 209, pp. 191-198.

Romani "Immunity to Fungal Infections," Nature Reviews Immunology, Jan. 2004, vol. 4, pp. 1-13.

Schreuder et al. "Yeast expressing hepatitis B virus surface antigen determinants on its surface: implications for a possible oral vaccine," Vaccine, Apr. 1996, vol. 14, No. 5, pp. 383-388.

Sinai et al. "Enhancement of Resistance to Infectious Diseases by Oral Administration of Brewer's Yeast," Infection and Immunity, May 1974, vol. 9, No. 5, pp. 781-787.

Steinman "Mixed results with modulation of TH-17 cells in human autoimmune diseases," Nature Immunology, Jan. 2010, vol. 11, No. 1, pp. 41-44.

Strom et al. "Recently Discovered T Cell Subsets Cannot Keep Their Commitments," Journal of the American Society of Nephrology, Jul. 2009, vol. 20, No. 7, pp. 1577-1680.

Stubbs et al., "Whole Recombinant Yeast Vaccine Activates Dendritic Cells and Elicits Protective Cell-Mediated Immunity," National Medicine, May 2001, vol. 7, No. 5, pp. 1-5.

Taylor et al. "Dectin-1 is required for b-glucan recognition and control of fungal infection," Nature Immunology, Jan. 2007, vol. 8, No. 1, pp. 31-38.

Valenzuela et al. "Antigen engineering in yeast: Synthesis and assembly of hybrid hepatitis B surface antigen-Herpes simplex 1 gD particles", Bio/Technology, Apr. 1985, vol. 3, 323-326.

Van De Veerdonk et al. "The Macrophage Mannose Receptor Induces IL-17 in Response to *Candida albicans,*" Cell Host & Microbe, Apr. 2009, vol. 5, pp. 329-340.

Yang et al. "TH17 lineage differentiation is programmed by orphan nuclear receptors RORa and RORy," Immunity, Jan. 2008, vol. 28, No. 1, pp. 29-39.

Ye et al. "Requirement of Interleukin 17 Receptor Signaling for Lung CXC Chemokine and Granulocyte Colony-stimulating Factor Expression, Neutrophil Recruitment, and Host Defense," The Journal of Experimental Medicine, Aug. 20, 2001, vol. 194, No. 4, pp. 519-527.

Young et al. "A Comparison of the Pulmonary Inflammatory Potential of Different Components of Yeast Cell Wall," Journal of Toxicology and Environmental Health, Part A, Jan. 2007, vol. 70, No. 13, pp. 1116-1124.

International Search Report for International (PCT) Patent Application No. PCT/US2010/048699, mailed Nov. 29, 2010 6 pages.

(56) References Cited

OTHER PUBLICATIONS

Written Opinion for International (PCT) Patent Application No. PCT/US2010/048699, mailed Nov. 29, 2010 10 pages.

International Preliminary Report on Patentability for International (PCT) Patent Application No. PCT/US2010/048699, mailed Mar. 29, 2012 10 pages.

Examination Report for European Patent Application No. 10755290.3, dated Jul. 12, 2013 4 pages.

Official Action for Eurpean Patent Application No. 10755290.3, dated Feb. 6, 2014 4 pages.

Official Action for Japan Patent Application No. 2012-529823, dated Sep. 2, 2014.

* cited by examiner yeast+ova
0.11 ova+aCD40
1.27 yeast+ova+aCD40
5.82 pam3cys+ova+aCD40
15.8
CD44
WT
Ovalbumin$_{267-264}$ H-2Kb naive
0.25 yeast
7.5 pam3cys
18.7
WT
CD44 naive
0.009 yeast
1.71 pam3cys
16.1
IL12Rβ2-/-
CD44 naive
0.2 yeast
2.26 pam3cys
14.0
tbet-/-
CD44
ovalbumin$_{257-264}$ H-2Kb

MODULATION OF YEAST-BASED IMMUNOTHERAPY PRODUCTS AND RESPONSES

CROSS-REFERENCE TO RELATED APPLICATIONS

This application is a national stage application under 35 U.S.C. 371 of PCT Application No. PCT/US2010/048699 having an international filing date of Sep. 14, 2010, which designated the United States, which PCT application claims the benefit of priority under 35 U.S.C. §119(e) from each of U.S. Provisional Application No. 61/242,353, filed Sep. 14, 2009, U.S. Provisional Application No. 61/242,355, filed Sep. 14, 2009, and U.S. Provisional Application No. 61/288,568, filed Dec. 21, 2009. Each of PCT Application No. PCT/US2010/048699, U.S. Provisional Application No. 61/242,353, U.S. Provisional Application No. 61/242,355, and U.S. Provisional Application No. 61/288,568 is incorporated herein by reference in its entirety

GOVERNMENT SUPPORT

This invention was made with government support under grant number R01 CA136146, awarded by the National Institutes of Health. The government has certain rights in the invention.

REFERENCE TO A SEQUENCE LISTING

This application contains a Sequence Listing submitted electronically as a text file by EFS-Web. The text file, named "3923-27-PCT_ST25", has a size in bytes of 78 KB, and was recorded on 13 Sep. 2010. The information contained in the text file is incorporated herein by reference in its entirety pursuant to 37 CFR §1.52(e)(5).

FIELD OF THE INVENTION

The present invention generally relates to methods to modulate yeast-based immunotherapy products and the immune responses, prophylactic responses, and/or therapeutic responses elicited by such products, as well as to modified yeast-based immunotherapy products and compositions.

BACKGROUND OF THE INVENTION

Prior to 2005, a major focus of T cell immunology dogma was directed to what is called a "TH1/TH2 paradigm", which refers to the generally accepted roles of two T helper (TH) cell subsets. TH cells are lymphocytes that typically express the surface protein, CD4, and influence the establishment and capabilities of the immune system. Disease outcome has been routinely associated with a skewing toward one or the other of these T cell subsets. The rationale was based on the observation that the way in which antigen is introduced to antigen presenting cells (APCs), such as dendritic cells (DCs), determined which TH subset was preferentially activated, thus influencing how the immune system responded. For example, in the endogenous pathway triggered by direct infection of the DC with, e.g., a virus, the activated DCs produced interleukin-12 (IL-12) and this led to the specific stimulation of TH1 T cells. TH1 activation led to the production of interleukin-2 (IL-2) needed to drive IL-2-dependent $CD8^+$ T cell immunity, which in turn led to direct lysis of infected cells. On the other hand, when antigen was presented to the DC via the exogenous pathway, such as by phagocytosis, the DC produced interleukin-10 (IL-10) leading to TH2 activation, the subsequent secretion of interleukin-4 (IL-4), and help for B cell production of antibody. Most disease pathology came to be associated with either cellular or humoral skewing of the immune response by the endogenous or exogenous presentation of antigen to the immune system. Where antibody was involved, TH2 were implicated, and when direct cytolytic activity was observed, for example in cell-mediated destruction of islets in Type I diabetes, it was assumed to be due to TH1 activity.

An additional player in the TH1/TH2 paradigm was the regulatory T cell (Treg). Treg function, which is generally directed to the modulation and deactivation of the immune response, was found to be dependent in the periphery (but not the thymus) on TGFβ and high IL-2 receptor expression. Treg, like TH2, produce IL-4, and Treg function in control of TH1 cells was thought to involve competition between TH1 and Treg for IL-2.

The exclusive trinity of TH1, TH2 and Treg changed in 2005 when investigators demonstrated, while knocking out the IL-12 gene, that immunity to fungal infections diminished. Careful study of the molecular rationale used to generate the IL-12 knockout mouse demonstrated that IL-12 shared a p40 common chain with another cytokine, interleukin-23 (IL-23). When the non-p40 chain unique to IL-23 was knocked out, TH1 function remained while fungal immunity continued to be thwarted (Cua et al, 2003; Murphy et al, 2003). It was soon discovered that the dominant cytokine responsible for fungal immunity was interleukin-17 (IL-17) and this was produced by what became known as TH17 T cells (Harrington et al, 2005) that are driven by DC-induced IL-23. IL-17 is not a growth factor for TH17 cells (Harrington et al, 2005; Langrish et al, 2005; Park et al, 2005), but instead recruits neutrophils and promotes granulopoiesis that leads to pathogen clearance.

TGFβ and interleukin-6 (IL-6) are two cytokines associated with TH17 development (Betteli et al, 2006; Mangen et al, 2006; Veldhoen et al, 2006). Under certain circumstances, TGFβ can be a growth factor for TH17 (Veldhoen et al, 2006), most prominently in the absence of Th1 or Th2 (Das et al, 2009), while in their presence may also function to suppress Th1 and Th2 development (Li et al, 2007). TGFβ is also a growth factor for regulatory T cells (Treg) (Korn et al, 2009). Competition between TH17 and Treg (Bettelli et al, 2006), to the detriment of the latter, is considered to be a mechanism whereby TH17 have been implicated in the induction of autoimmune disorders such as multiple sclerosis (Matusevicius et al, 1999; Lock et al, 2002), rheumatoid arthritis (Murphy et al, 2003; Kirkmam et al, 2006), type I diabetes (Vukkadapu et al, 2005; Bradshaw et al, 2009), psoriasis (Wilson et al, 2007; Krueger et al, 2007), uveitis (Luger et al, 2008), inflammatory bowel disease (Fujino et al, 2003; Duerr et al, 2006) and Crohn's disease (Schmidt et al, 2005; Fuss et al, 2006). The TH17-associated cytokine, IL-6, directly suppresses Treg differentiation as well (DeLuca et al, 2007; Korn et al, 2008). Accordingly, targeting TH17 or their inductive factors has been described as a potential means to treat autoimmune diseases (DeBenedetti, 2009; Pernis, 2009).

The molecular signatures of TH1, TH2, TH17 and Treg are controlled by the subset-specific transcription factors, T-bet, GATA-3, ROR (retinoic acid orphan receptor) and FoxP3, respectively. FoxP3 inhibits IL-2 transcription, thus giving Treg an avaricious appetite for exogenous sources of IL-2. ROR expression has been reported to be anti-proliferative.

TH17 T cells are induced in response to certain bacterial or fungal extracellular pathogens including *Klebsiella pneumoniae, Bordatella pertussis, Streptococcus pneumoniae* and

*Candida albicans* (Ye, et al, 2001; Huang et al., J. Infect. Dis. 190:624-631 (2004), Happel et al, 2005; Higgens et al, 2006; DeLuca et al, 2007; Lu et al, 2008; Zhang et al, 2009). In general, these pathogens primarily colonize exposed surfaces such as airways, skin and the intestinal lumen (Peck and Mellins, 2009). This immune response has been reported to be elicited by interactions of microbial components with various pattern recognition receptors (PRRs) on the surface of APCs, including dectin-1 and Toll-like receptors (TLRs), which lead to activation of TH17 cells and other proinflammatory events (see, e.g., LeibundGut-Landmann et al., Nat. Immunol. 8(6)630-638 (2007); Acosta-Rodriguez, Nat. Immunol. 8(6):639-646 (2007); Taylor et al., Nat Immunol. 8(1): 31-38 (2007)). Activation of dectin-1 and various TLR pathways has been shown to result in reciprocal regulation of IL-23 and IL-12 pathways (see, e.g., Gerosa et al., *J. Exp. Med.* 205(6)1447-1461 (2008) and Dennehy et al., *Eur J Immunol.* 39(5):1379-1386 (2009)). TH17 clear microbial infections via the cytokine-mediated recruitment of neutrophils. There is also evidence for a role for TH17 against certain intracellular pathogens such as *Listeria monocytogenes, Salmonella enteriditis, Toxoplasma gondii, Clamydia trachomatis* and *Mycobacterium tuberculosis* (Harty and Bevan, 1995; Dalrymple et al, 1995; Cooper et al, 2002; Kelly et al, 2005; Khader et al, 2005; Schulz et al, 2008; Zhang et al, 2008) among others.

In the 1990's, yeast-based immunotherapy compositions were introduced as novel compositions for inducing immune responses through both the MHC class I-restricted and the MHC class II-restricted pathways of antigen-presenting cells (see U.S. Pat. No. 5,830,463). Although these compositions are initially exposed to the immune system as an exogenous antigen(s), yeast-based immunotherapy compositions are uniquely able to trigger the induction of both a CD8+ cytotoxic T cell response through cross-presentation of antigens by the MHC class I-restricted pathway, as well as a CD4+ T cell response through presentation of antigens by the MHC class II-restricted pathway (See, e.g., U.S. Pat. Nos. 5,830,463 and 7,083,787, Stubbs et al., Nat. Med. 7:625-629 (2001) and Lu et al., Cancer Research 64:5084-5088 (2004)). Yeast-based immunotherapy compositions stimulate pattern recognition receptors (PRR); upregulate adhesion molecules, costimulatory molecules, and MHC class I and class II molecules on antigen presenting cells including DCs; and induce the production of proinflammatory cytokines by antigen presenting cells (e.g., TNF-α and IL-12) (see, e.g., Stubbs et al., supra; Brown et al., *J Exp. Med.* 197:1119-1124 (2003)).

In the context of yeast-based immunotherapeutic compositions, which may be engineered to express one or more antigens, the complexities of the mechanism of action of yeast-based immunotherapeutics with respect to the immune system and therapeutic efficacy have not yet been fully identified. It is desirable to better understand how different individuals respond to immunization with yeast-based immunotherapy compositions, and thereby be able to manipulate and personalize immunotherapeutic strategies to more effectively elicit a desired immune response that is most appropriate for a given disease or condition in an individual.

SUMMARY OF THE INVENTION

Various embodiments of the invention are described below. However, the invention is not limited to embodiments described in this summary, as inventions described in the description that follows are also expressly encompassed.

One embodiment of the invention relates to a method to enhance the immunotherapeutic properties of a yeast-based immunotherapy composition. The method includes a step of administering to a subject: (a) a yeast-based immunotherapy composition; and (b) an agent that modulates the production or survival of CD4+ TH17 cells. The agent is administered prior to, in conjunction with, and/or following administration of the dose of yeast-based immunotherapy composition, in order to enhance the immunotherapeutic properties of the yeast-based immunotherapy in the subject.

Another embodiment of the invention relates to the use of a composition in the preparation of a medicament to enhance the immunotherapeutic properties of a yeast-based immunotherapy composition in a subject. The composition comprises: (a) a yeast-based immunotherapy composition; and (b) an agent that modulates the production or survival of CD4+ TH17 cells.

In one aspect of any embodiment of the invention described herein, the subject is a non-responder or partial responder to yeast-based immunotherapy with respect to one or more symptoms associated with a disease.

Yet another embodiment of the invention relates to a method to improve the efficacy of yeast-based immunotherapy in a subject who is a non-responder or partial responder to yeast-based immunotherapy, with respect to one or more symptoms associated with a disease. The method includes the step of administering to the subject an agent that modulates the production or survival of TH17 cells, the administration being prior to, in conjunction with, or following administration of a dose of yeast-based immunotherapy composition, to improve the efficacy of the yeast-based immunotherapy in the subject.

In one aspect of any embodiment of the invention described above, the disease is a viral disease. In one aspect, in the absence of the agent, the subject fails to produce a sufficient therapeutic immune response against the virus, fails to reduce viral load to a level sufficient to achieve a therapeutic response, and/or fails to reduce the frequency or severity of at least one symptom of the viral infection in response to administration of the yeast-based immunotherapy. Such a viral disease can include, but is not limited to, a hepatitis virus infection (e.g., hepatitis C virus infection or hepatitis B virus infection).

In one aspect of any embodiment of the invention described above, the disease is a cancer. In one aspect, in the absence of the agent, the subject fails to produce a sufficient therapeutic immune response against the cancer, fails to reduce tumor burden, fails to inhibit tumor growth, and/or fails to increase survival in response to yeast-based immunotherapy.

In one aspect of any embodiment of the invention described above, the disease is an infection by an intracellular pathogen. In one aspect, in the absence of the agent, the subject fails to produce a sufficient therapeutic immune response against the pathogen, fails to reduce pathogen load to a level sufficient to achieve a therapeutic response, and/or fails to reduce the frequency or severity at least one symptom of the pathogen infection in response to administration of the yeast-based immunotherapy.

One embodiment of the invention relates to a method to upregulate TH1-mediated immune responses to yeast-based immunotherapy. The method includes the steps of: (a) administering to a subject a yeast-based immunotherapy composition; and (b) administering to the subject an agent that downregulates the production or survival of TH17 CD4+ T cells.

Another embodiment of the invention relates to a method to treat cancer or ameliorate one or more symptoms thereof, including the steps of: (a) administering to a subject a yeast-based immunotherapy composition; and (b) administering to the subject an agent that downregulates the production or survival of TH17 CD4+ T cells.

Yet another embodiment of the invention relates to a method to treat a viral infection, or to ameliorate one or more symptoms thereof, the method including the steps of: (a) administering to a subject a yeast-based immunotherapy composition; and (b) administering to the subject an agent that downregulates the production or survival of TH17 CD4+ T cells. In one aspect, the viral infection is a hepatitis virus infection, which can include, but is not limited to, hepatitis B virus and hepatitis C virus.

In any of the embodiments of the invention described above, in one aspect that is not mutually exclusive of other aspects, the subject produces a strong TH17 response as a result of administration of the yeast-based immunotherapy composition in the absence of the agent. In one aspect that is not mutually exclusive of other aspects, T cells isolated from the subject do not proliferate or proliferate weakly in response to contact with a yeast-based immunotherapy composition. In one aspect that is not mutually exclusive of other aspects, T cells isolated from the subject have greater than normal RORγt expression and/or have greater than normal levels of IL-17 production. In one aspect that is not mutually exclusive of other aspects, the subject is non-responsive or partially responsive to type I interferon therapy.

In one aspect of any of the above-described embodiments, the method or use further comprises an agent that upregulates the production or survival of TH1 cells and/or downregulates the production and/or survival of Tregs.

In one aspect of any of the embodiments described herein, administration of the agent and the yeast-based immunotherapy enhances CD8+ T cell responses, as compared to administration of the yeast-based immunotherapy composition alone.

In one aspect of any embodiment of the invention described herein, the disease is a fungal disease. In one aspect of this embodiment, the subject produces a weak TH17 response as a result of administration of the yeast-based immunotherapy composition in the absence of the agent. In one aspect, T cells isolated from the subject proliferate in response to contact with a yeast-based immunotherapy composition. In one aspect, T cells isolated from the subject have normal or less than normal RORγt expression and/or have normal or less than normal levels of IL-17 production.

In one aspect of any of the embodiments described herein, when downregulation of the production and/or survival of TH17 cells, upregulation of the production and/or survival of TH1 cells, and/or downregulation of the production and/or survival of Tregs is desired, the agent inhibits the expression or activity of IL-1, IL-6, IL-17, IL-21, IL-22, IL-23, or a receptor thereof, or is IL-25 or IL-27 or an agonist thereof. In one aspect, the agent downregulates the expression or activity of interleukin-1 (IL-1) or a receptor of IL-1. In one aspect, the agent downregulates the expression or activity of interleukin-6 (IL-6) or a receptor of IL-6. In one aspect, the agent downregulates the expression or activity of interleukin-17 (IL-17) or a receptor of IL-17. In one aspect, the agent downregulates the expression or activity of IL-21 or a receptor of IL-21. In one aspect, the agent downregulates the expression or activity of interleukin-22 (IL-22) or a receptor of IL-22. In one aspect, the agent downregulates the expression or activity of interleukin-23 (IL-23) or a receptor of IL-23. In one aspect, the agent is IL-25 or an agonist of IL-25 or its receptor. In one aspect, the agent is IL-27 or an agonist of IL-27 or its receptor.

In one aspect of any of the embodiments described herein, when downregulation of the production and/or survival of TH17 cells, upregulation of the production and/or survival of TH1 cells, and/or downregulation of the production and/or survival of Tregs is desired, the agent is selected from: Toll-Like Receptor (TLR) agonists or combinations thereof, type I interferons, type II interferons, type III interferons, IL-12, anti-IL-12R, anti-CD40, CD40L or agonists thereof, LAG3, IMP321, C-type lectin receptors including soluble receptors, anti-inflammatory agents, immunomodulators, and/or immunotherapeutic vaccines.

In one aspect of any of the embodiments described herein, when downregulation of the production and/or survival of TH17 cells, upregulation of the production and/or survival of TH1 cells, and/or downregulation of the production and/or survival of Tregs is desired, the agent is selected from: an anti-fungal agent, an antibiotic, an anti-inflammatory agent, an immunomodulatory agent, and/or a vitamin.

In one aspect of any embodiments described herein, when upregulation of the production and/or survival of TH17 cells, downregulation or delay of the production and/or survival of TH1 cells is desired, the agent is, or elicits or increases the expression or activity of, IL-1, IL-6, IL-17, IL-21, IL-22, IL-23, or a receptor thereof, or inhibits the expression or activity of IL-25 or IL-27 or a receptor thereof.

In any of the embodiments described herein, in one aspect, the agent is targeted to an antigen presenting cell. In one aspect, the agent is targeted to a T cell.

In any of the embodiments described herein, in one aspect, the agent is selected from the group consisting of: an antibody or an antigen-binding portion thereof; siRNA; a protein or peptide; a small molecule; and an aptamer. In one aspect, the agent is an antibody or antigen-binding portion thereof.

In any of the embodiments described herein, in one aspect, the agent is administered concurrently with the yeast-based immunotherapy composition, before administration of the yeast-based immunotherapy composition, after administration of the yeast-based immunotherapy composition, and/or intermittently with the yeast-based immunotherapy composition.

In any of the embodiments described herein, in one aspect, the yeast-based immunotherapy composition is administered in one or more doses over a period of time prior to commencing the administration of the agent.

In yet another aspect, the yeast-based immunotherapy composition is administered in one or more doses over a period of time prior to commencing the administration of the agent. In another aspect, the agent is administered in one or more doses over a period of time prior to commencing the administration of the yeast-based immunotherapy composition.

In any of the embodiments described herein, in one aspect, the agent is administered for a defined period of time (e.g., a predefined or defined number of doses and/or a predefined or defined number of weeks or months) sufficient to modulate an initial immune response in the subject receiving the yeast-based immunotherapy, followed by a period of time wherein the yeast-based immunotherapy composition is administered in the absence of the agent.

In any of the embodiments described herein, in one aspect, the yeast used to produce the yeast-based immunotherapy composition have been engineered to carry or express the agent.

Another embodiment of the invention relates to a method to enhance the immunotherapeutic properties of a yeast-based immunotherapy composition, comprising administering to a subject a yeast-based immunotherapy composition, wherein the yeast used to produce the yeast-based immunotherapy composition have been genetically modified and/or have been produced under conditions that modify the ability of the yeast to induce a CD4+ TH17 immune response in the subject. Yet another embodiment relates to the use of a yeast-based immunotherapy composition to enhance immunotherapy in a subject, wherein the yeast used to produce the yeast-based immunotherapy composition have been genetically modified or have been produced under conditions that modify the ability of the yeast to induce a CD4+ TH17 immune response in the subject.

Another embodiment of the invention relates to a method to enhance TH1-mediated immune responses to yeast-based immunotherapy, the method including the step of administering to a subject a yeast-based immunotherapy composition, wherein the yeast used to produce the yeast-based immunotherapy composition have been genetically modified and/or have been produced under conditions that reduce the ability of the yeast to induce a TH17 immune response in the subject. In one aspect of this embodiment, the subject has cancer. In one aspect, the subject has a viral infection.

In one aspect of this embodiment, the yeast used to produce the yeast-based immunotherapy composition have been produced under conditions that modify the yeast cell wall so that signaling through a C-type lectin receptor (e.g., a dectin), a mannose receptor, and/or a DC-SIGN receptor of an antigen presenting cell contacted with the yeast-based immunotherapy composition is increased. In one aspect, the yeast used to produce the yeast-based immunotherapy composition have been produced under conditions that modify the yeast cell wall so that signaling through a dectin receptor (e.g., Dectin-1, Dectin-2), a mannose receptor, and/or a DC-SIGN receptor of an antigen presenting cell contacted with the yeast-based immunotherapy composition is decreased. In one aspect, the yeast used to produce the yeast-based immunotherapy composition have been produced under conditions that reduce or eliminate the exposure of β-glucans on the cell wall surface of the yeast. In one aspect, the yeast used to produce the yeast-based immunotherapy composition have been produced under conditions that increase the exposure of β-glucans on the cell wall surface of the yeast. In one aspect, the yeast used to produce the yeast-based immunotherapy composition have been produced under conditions that reduce or eliminate the exposure of mannose on the cell wall surface of the yeast. In one aspect, the yeast used to produce the yeast-based immunotherapy composition have been produced under conditions that increase the exposure of mannose on the cell wall surface of the yeast. In one aspect, the yeast-based immunotherapy composition have been produced under conditions that reduce the ability of the yeast to induce a TH17-mediated immune response. In another aspect, the yeast used to produce the yeast-based immunotherapy composition have been produced under conditions that increase the ability of the yeast to induce a TH17-mediated immune response.

Yet another embodiment of the invention relates to a method to screen subjects for predicted immune responsiveness to yeast-based immunotherapy. The method includes the steps of: (a) contacting T cells from a subject in vitro with antigen presenting cells (APCs) that have been contacted with a yeast-based immunotherapy composition; (b) detecting a phenotype of the T cells selected from the group consisting of: T cell proliferation in response to contact with the APCs, IL-17 production by the T cells in response to contact with the APCs, and expression of retinoid-related orphan receptor (RORγt) by T cells in response to contact with the APCs. Subjects, whose T cells proliferate in response to contact with the APCs, or have normal production of IL-17 or normal expression of RORγt, are predicted to be good candidates for administration of a yeast-based immunotherapy composition. Subjects whose T cells fail to proliferate or proliferate poorly in response to contact with the APCs, or whose T cells produce greater than normal amounts of IL-17 or have greater than normal expression of RORγt, are predicted to be candidates for administration of a yeast-based immunotherapy composition in conjunction with an agent that inhibits the production or survival of TH17 cells. Subjects whose T cells produce lesser than normal amounts of IL-17 or have lesser than normal expression of RORγt, are predicted to be candidates for administration of a yeast-based immunotherapy composition in conjunction with an agent that increases the production or survival of TH17 cells.

Another embodiment of the invention relates to a composition comprising: (a) a yeast-based immunotherapy composition; and (b) an agent that modulates the production and/or survival of TH17 cells. In one aspect, the agent elicits or downregulates the production and/or survival of TH17 cells. In one aspect, the agent upregulates the production and/or survival of TH17 cells. Such agents have been described in detail in other embodiments above and elsewhere herein. In one aspect, the agent down-regulates the expression or activity of a cytokine selected from the group consisting of: interleukin-1 (IL-1), IL-6, IL-17, IL-21, IL-22 and IL-23, or a receptor thereof. In one aspect, the agent comprises interleukin-25 (IL-25), IL-27, or an agonist thereof. In one aspect, the agent comprises an agent that elicits or enhances the production or survival of TH17 cells. In one aspect, the agent comprises interleukin-1 (IL-1), IL-6, IL-17, IL-21, IL-22 and IL-23, or an agonist thereof. In one aspect, the agent down-regulates the expression or activity of interleukin-25 (IL-25), IL-27, or a receptor thereof.

Yet another embodiment of the invention relates to a kit comprising any of the compositions, including any of the yeast-based immunotherapy compositions and/or any of the agents described herein.

Another embodiment of the invention relates to a method to modulate the proliferative response of T cells in a subject to yeast-based immunotherapy. The method includes administering to the subject an agent that modulates the production or survival of TH17 cells, the administration being prior to, in conjunction with, or following administration of a dose of yeast-based immunotherapy composition, to modulate the proliferative response of T cells to yeast-based immunotherapy in the subject. Agents useful in this embodiment include any of the agents described above or elsewhere herein for modulation of a TH17 immune response.

Yet another embodiment of the invention relates to a method to produce a yeast-based immunotherapy composition that enhances TH1-mediated immune responses. The method includes genetically engineering the yeast used to produce the yeast-based immunotherapy composition in a manner effective to reduce a TH17-mediated response in a subject to whom the yeast-based immunotherapy composition is administered.

Yet another embodiment of the invention relates to a method to produce a yeast-based immunotherapy composition that enhances TH1-mediated immune responses, the method including producing the yeast used to produce the yeast-based immunotherapy composition under conditions effective to reduce a TH17-mediated response in a subject to whom the yeast-based immunotherapy composition is administered.

Another embodiment of the invention relates to a composition comprising: (a) a yeast-based immunotherapy composition; and (b) an agent that downregulates the expression or activity of a cytokine selected from the group consisting of: interleukin-1 (IL-1), IL-6, IL-17, IL-21, IL-22 and IL-23, or a receptor thereof.

Yet another embodiment of the invention relates to a composition comprising: (a) a yeast-based immunotherapy composition; and (b) interleukin-25 (IL-25), IL-27, or an agonist thereof.

Another embodiment of the invention relates to a composition comprising: (a) a yeast-based immunotherapy composition; and (b) an agent that elicits or enhances the production or survival of TH17 cells.

Yet another embodiment of the invention relates to a composition comprising: (a) a yeast-based immunotherapy composition; and (b) a cytokine selected from the group consisting of: interleukin-1 (IL-1), IL-6, IL-17, IL-21, IL-22 and IL-23, or an agonist thereof.

Another embodiment of the invention relates to a composition comprising: (a) a yeast-based immunotherapy composition; and (b) an agent that downregulates the expression or activity of interleukin-25 (IL-25), IL-27, or a receptor thereof.

Another embodiment of the invention relates to a kit comprising: (a) a yeast-based immunotherapy composition; and (b) an agent that downregulates TH17 cells.

Yet another embodiment of the invention relates to a kit comprising: (a) a yeast-based immunotherapy composition; and (b) an agent that downregulates the expression or activity of a cytokine selected from: interleukin-1 (IL-1), IL-6, IL-17, IL-21, IL-22 and/or IL-23, and/or a receptor thereof.

Another embodiment of the invention relates to a kit comprising: (a) a yeast-based immunotherapy composition; and (b) interleukin-25 (IL-25), IL-27, or an agonist thereof.

Another embodiment of the invention relates to a kit comprising: (a) a yeast-based immunotherapy composition; and (b) an agent that upregulates the production or survival of TH17 cells.

Yet another embodiment of the invention relates to a kit comprising: (a) a yeast-based immunotherapy composition; and (b) a cytokine selected from the group consisting of: interleukin-1 (IL-1), IL-6, IL-17, IL-21, IL-22 and IL-23, or an agonist thereof.

Another embodiment of the invention relates to a kit comprising: (a) a yeast-based immunotherapy composition; and (b) an agent that downregulates the expression or activity of interleukin-25 (IL-25), IL-27, or a receptor thereof.

Another embodiment of the invention relates to a kit comprising: (a) a yeast-based immunotherapy composition; and (b) reagents for detecting TH17 cells.

Another embodiment of the invention relates to a method to measure antigen-specific, CD8+ T cell responses to a yeast-based immunotherapy composition, the method including the steps of: (a) immunizing a non-human animal with a yeast-based immunotherapy composition, wherein TH17 responses are inhibited or blocked in the non-human animal; (b) injecting the immunized non-human animal with a mixture of equal numbers of labeled target cells and labeled non-target cells, wherein the target cells express or display an antigen against which the yeast-based immunotherapy composition elicits a T cell response, wherein the non-target cells do not express or display the antigen, and wherein the target cells are labeled differently than the non-target cells; (c) collecting a population of cells from the non-human animal that contain the labeled target cells and labeled non-target cells; and (d) measuring antigen-specific CD8+ T cells in the non-human animal by detecting a difference in the ratio of target cells to non-target cells, wherein the reduction of target cells as compared to non-target cells indicates the level of antigen-specific, CD8+ T cell response in the non-human animal. In one aspect, the target cells are spleen cells that have been pulsed the peptides of the target antigen. In one aspect, the population of cells in (c) is from spleen. In one aspect, the target cells are tumor cells that express the target antigen. In one aspect, the population of cells in (c) is from liver. In one aspect, step (d) is performed using flow cytometry.

Another embodiment of the invention relates to a method to measure antigen-specific, CD8+ T cell responses to a yeast-based immunotherapy composition, the method including the steps of: (a) immunizing a non-human animal with a yeast-based immunotherapy composition, wherein TH17 responses are inhibited or blocked in the non-human animal; (b) collecting a population of cells from the non-human animal of (a) that contain CD8+ T cells; and (c) measuring antigen-specific CD8+ T cell responses in the non-human animal by detecting the ability of CD8+ T cells in the population of (c) to detect antigen-MHC complexes. In one aspect, the population of cells in (c) is a population containing peripheral blood mononuclear cells. In one aspect, the antigen-MHC complexes are tetramers.

In either of the above-described methods to measure antigen-specific CD8+ T cell responses, in one aspect, the non-human animal is a mouse. In one aspect, the expression or activity of a cytokine selected from: IL-1, IL-6, IL-17, IL-21, IL-22, and/or IL-23, is blocked or inhibited in the non-human animal. In one aspect, the non-human animal is an IL-6 homozygous knock-out mouse.

In any of the methods, uses, compositions or kits described above or elsewhere herein, in one aspect, the yeast-based immunotherapeutic composition comprises a yeast vehicle and an antigen, wherein the antigen is expressed by, attached to, or mixed with the yeast vehicle. In one aspect, the antigen is expressed by the yeast vehicle. In one aspect, the antigen is mixed with the yeast vehicle. In one aspect, the antigen is attached to the yeast vehicle. In one aspect, the yeast vehicle is selected from: a whole yeast, a yeast spheroplast, a yeast cytoplast, a yeast ghost, and/or a subcellular yeast membrane extract or fraction thereof. In one aspect, the yeast vehicle is selected from: a whole yeast and/or a yeast spheroplast. In one aspect, the yeast vehicle is a whole yeast. In one aspect, the yeast vehicle is a heat-inactivated whole yeast. In one aspect, the yeast vehicle is from *Saccharomyces*. In one aspect, the yeast vehicle is from *Saccharomyces cerevisiae*.

BRIEF DESCRIPTION OF THE DRAWINGS

FIG. 1B=YVEC+ ovalbumin; FIG. 1C=YVEC; FIG. 1D=naïve).

DETAILED DESCRIPTION OF THE INVENTION

Figures 1A, 1B, 1C, 1D:
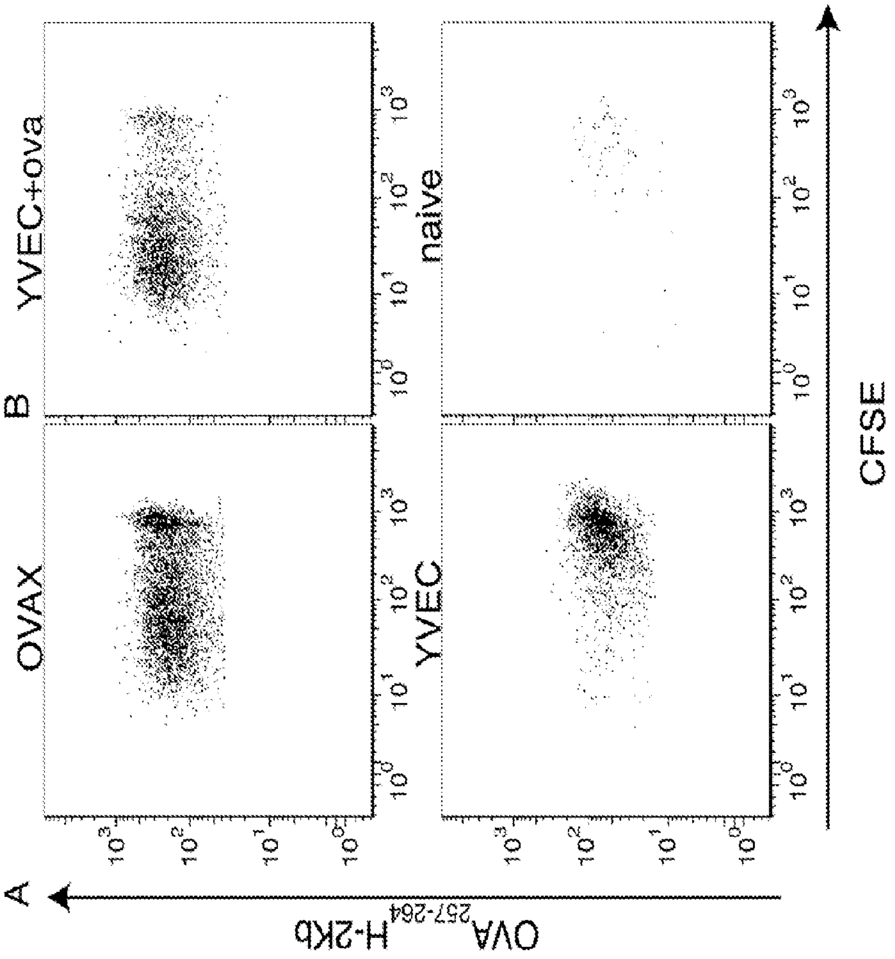
FIGS. 1A-1D are flow cytometry graphs showing the generation of primary, antigen-specific CD8+ cell-mediated immunity resulting from immunization with a yeast-based immunotherapy product (FIG. 1A=OVAX.

The present invention generally relates to the inventors' discovery of mechanisms by which yeast-based immunotherapeutic compositions interact with the immune system, and to the utilization of this discovery to provide new methods for producing or formulating compositions containing yeast-based immunotherapy compositions, and to methods and compositions for using yeast-based immunotherapy to specifically modulate the immune response and improve the efficacy of yeast-based immunotherapy for various disease states in an individual. The invention also includes methods and kits for measuring immune responses elicited by yeast-based immunotherapy compositions, and methods for screening subjects for immune responses elicited by yeast-based immunotherapy compositions.

A major goal of immunotherapy has been to generate and expand antigen specific CD8+ effector T cells. This process can be facilitated by type I interferons that enhance the cross presentation of viral or tumor antigens to the Class I MHC pathway utilized by CD8 T cells, and type I interferons upregulate interferon response genes that have other effects, such as direct inhibition of viral replication. Unfortunately, interferon-mediated therapies are not uniformly successful; therefore, engaging type I interferon-independent pathways is of value.

The present invention provides evidence that yeast-based immunotherapy invokes an interferon-independent, CD4-dependent generation of CD8 T cells, and further demonstrates that yeast-based immune responses can be regulated to "personalize" or selectively modify the type of immune response desired in a particular individual and for a specific disease or condition. More particularly, it is demonstrated herein that administration of a yeast-based immunotherapeutic induces TH17 T cells, that the induction of this TH phenotype occurs concomitantly with the type I interferon-independent generation of TH1 $CD4^+$ and antigen-specific $CD8^+$ T cell-mediated immunity that is dependent on IL-12. It is further demonstrated herein that the persistence of $CD8^+$ T cells following repeated immunization with a yeast-based immunotherapeutic is associated with the generation of countermeasures by the yeast-based immunotherapeutic that reduce the frequency of Treg. Therefore, TH17 induction by the yeast can favor persistent $CD8^+$ T cell generation by allowing an interferon-independent, CD4-dependent CD8+ T cell response to occur and by interfering with the regulatory T cells that otherwise control the $CD8^+$ cells. Other immunostimulatory approaches that engage TLRs without activation of TH17 may lack this immunoregulatory component that interferes with the function of Tregs, illustrating a benefit of yeast-based immunotherapy. Moreover, other immunostimulatory approaches that engage TLRs, such as TLR agonist approaches, may be dependent upon type I interferon; the ability of yeast-based immunotherapy to elicit a type I interferon-independent, cell-mediated immune response allows individuals who lack or have an impaired ability to respond to type I interferon an avenue for immune responsiveness.

Taken as a whole, these data reveal an intricate balance between TH1 and TH17 in the generation of persistent and immunotherapeutically productive, cell-mediated immunity generated by yeast-based immunotherapy, and indicate that modulation of these pathways is a way to tailor the immune response for a given individual and/or disease state.

For example, the present inventors demonstrate herein that yeast-based immunotherapy-mediated generation of antigen specific CD8+ T cells can be potently influenced by modulating the TH17 T helper cell pathway. Indeed, evidence is provided herein that the balance point of yeast-based immunotherapy rests with the generation of TH17 CD4+ T cells that can control CD8+ T cell generation. In the Examples, the inventors show that by depletion of IL-6, a cytokine that drives an immune response toward the TH17 pathway, CD8+ antigen-specific T cell responses to yeast-based immunotherapy can be significantly increased, e.g., from approximately 1-5% to approximately 25-33% of the total CD8+ response, or more. There is an apparent conundrum that the pro-inflammatory IL-6 generated as a result of administration of a yeast-based composition has a negative impact on TH1-mediated responses, while yeast-based immunotherapy compositions are known to be potent inducers of TH1-mediated CD8+ T cell responses. However, given the discoveries described herein, and without being bound by theory, the present inventors believe that yeast-based immunotherapeutics, acting in part as fungi, induce the TH17 pathway, and that this heavily influences the development of CD8+ T cells through the initial generation of TH17 rather than TH1 inflammation. More particularly, the inventors believe that in most individuals, yeast-based immunotherapy has an initial pro-inflammatory effect leading to TH17 response which, as inflammation resolves, shifts to a TH1-mediated response that assist CD8+ T cell expansion. The inventors propose that an agent that blocks or inhibits this TH17 pathway, including but not limited to an agent that inhibits IL-6, will promote CD8+ T cell development by refocusing an initial TH17 response toward the IL-12-dependent, TH1 pathway, or by reducing an “over-commitment” to a TH17 pathway that may experienced by some individuals. While such agents are particularly useful in subjects that have a partial or non-response to yeast-based immunotherapy when a CD8 response is desired (e.g., in cancer or viral infection), such agents are anticipated to enhance the CD8 response generated by yeast-based immunotherapy in most individuals and as such, can be used to general enhance TH1-mediated immune responses to yeast-based immunotherapy. Similarly, the reverse approach can be used to enhance TH17 responses in subjects who have weaker TH17 responses in situations when a stronger TH17 response may be beneficial (e.g., fungal infection or extracellular pathogen infection).

Without being bound by theory, the inventors believe that individuals have different TH17 set points and that they can be broadly classified as either “weaker” or “stronger” TH17 producers. Weaker TH17 activity correlates with responsiveness to type I interferon and CD4-independent CD8 T cell responses, and stronger TH17 activity is associated with the eventual preferential generation of a CD4 TH1-mediated generation of CD8 T cells. In general terms, weaker TH17 activity equates to CD4 T cell-independence and type I interferon-dependence, whereas stronger TH17 activity equates to CD4 T cell-dependence and type I interferon-independence. Accordingly, yeast-based immunotherapy provides a therapy that can be modified by regulating TH17 activity in an individual, and also provides an alternative or additional pathway for immune responsiveness to type I interferon-based therapy, which may be particularly useful in certain patient populations and/or in certain diseases or conditions. It is appreciated that the invention is directed to “modulation” of an immune response to yeast-based immunotherapy in a manner that “skews” an immune response in one direction or another. In other words, in most circumstances, it would not necessarily be desirable to completely block or over-activate a TH17 pathway versus a TH1 pathway versus a Treg pathway; rather, it is desirable to modulate the response based on what disease is to be treated, what type of immune response(s) will be most beneficial at what time, and how the individual responds to yeast-based immunotherapy, in order to maximize the therapeutic effect of the immunotherapy.

Since one way to address TH17 to TH1 access resulting from yeast-based immunotherapy is to restrict the TH17 initiation, which is heavily dependent on IL-6, the inventors chose to test the yeast-based immunotherapy technology in an IL-6 knockout mouse. The inventors discovered that upon administration of a yeast-based immunotherapeutic composition, this mouse readily moved the immune response away from TH17 and directly to TH1. More particularly, while wild type mice reproducibly generated 1-5% antigen-specific CD8+ cells following one dose of appropriately administered TARMOGEN® immunotherapy (a yeast-based immunotherapy, GlobeImmune, Inc., Louisville, Colo.), this frequency was increased routinely to 30% or more in an IL-6 knockout mouse (e.g., see FIG. 2C and FIG. 6B. Therefore, IL-6 in the wild-type mice was at least delaying the TH1 to CD8+ T cell transition, and without being bound by theory, the inventors believe this was via promulgation of the TH17 pathway. Interestingly, the generation of antigen specific $CD8^+$ T cells via the TLR2 pathway (via Pam3cys) was unaffected by the elimination of IL-6.

These results showed that a mechanism of yeast-based immunotherapy includes a role for IL-6 and TH17 T cells (and accordingly for cytokines in the TH17 pathway, such as IL-17 or IL-23), in addition to TH1 T cells. The inventors have further demonstrated herein that both TH17 and TH1 T cells are elicited after administration of yeast-based immunotherapy by parallel experiments using wild-type and T-bet knockout mice (i.e. mice in which the TH1-dependent transcription factor, T-bet, is deleted). Both TH1 and TH17 T cells were induced by yeast-based immunotherapy, but not by a TLR2 agonist. Therefore, the whole yeast-based immunotherapy can generate CD8 T cells via a TH1-dependent process influenced/controlled by TH17 that are in turn induced by an IL-6 dependent process.

Interestingly, whereas the yeast-dependent CD8 T cell response was reduced to background levels when TH1-dependent CD4 T cells were eliminated (see Example 2), when all CD4 T cell populations were eliminated (i.e., TH1, TH17, etc.), yeast-based immunotherapy induced CD8 responses that were improved relative to the corresponding CD8 responses in wild-type mice. Taken together, these results indicate that CD4 T cells regulate the CD8 response to yeast in ways that are distinct from the immune response to TLR-specific stimuli. While yeast can provoke a CD4-independent CD8 T cell response comparable to that observed with the CD4-independent TLR agonist pam3cys, with the caveat that this occurred in an environment devoid of CD4 T cells, they can also provoke a TH1 CD4-dependent/IL-12-dependent CD8 T cell response that is influenced by yet another CD4 subset, TH17, confirming a role for yeast-generated CD4 T cells in both inducing and regulating the response to yeast immunization.

The inventors also show that engagement of dectin-1, a C-type lectin receptor on dendritic cells, is not the only mechanism by which yeast-based immunotherapeutics induce IL-6 production and TH17 responses. Without being bound by theory, the inventors believe that IL-6 can be produced as a result of engagement of receptors other than the dectin-1 receptor, which may include, but are not limited to, dectin-2 receptor, mannose receptor, DC-SIGN receptor, and/or other C-type lectin receptors.

The inventors have also demonstrated that the induction of TH17 T cells resulting from yeast-based immunotherapy is associated with a reduction in regulatory T cell (Treg) frequencies (see Example 5). TH17 induction has been associated negatively with Tregs, and there is evidence that not only are TH17 cells on an axis with TH1 cells, but they can also convert Treg to a TH17 phenotype. In fact, autoimmunity is thought to be associated with the persistence of IL-6-driven TH17 that compete for limiting TGFβ and starve the Treg development pathway. Although one explanation for the observation that yeast-based immunotherapy reduces Tregs is that in the TH17-inducing environment, IL-6 directly targets regulatory T cell development via IL-6 mediated interference with FoxP3 function, without being bound by theory, the inventors believe that other explanations are supported by the data presented herein. For example, it is possible that the production of markedly enhanced antigen-specific $CD8^+$ T cell responses by yeast-based immunotherapy in an IL-6 knockout mouse is a result of a paucity of TH17 T cell induction, skewing what formerly was a coordinate TH1-TH17 immune response to one highly skewed to TH1. Another alternate explanation is supported by the data provided herein. TH17, like Treg, depend on TGFβ for survival, and the difference between whether the T cells become a TH17 or Treg in the presence of TGFβ is the presence of IL-6 and the increased sensitivity of TH17 to TGFβ, i.e., TH17 requires less TGFβ than Treg. TH17 T cells, because of their requirement for lower amounts of TGFβ, "outcompete" Treg for this essential growth factor. TH17 could also be produced via an IL-6 independent pathway, such as through an IL-21-dependent pathway. Independent evidence for this pathway comes from the studies of repetitive immunization described herein. If one assumes that the absence of IL-6 ultimately favors the induction of uncontrolled Treg then antigen-specific $CD8^+$ T cell responses would be expected to deteriorate with the frequency of immunization. However, as shown in the Examples, administration of yeast-based immunotherapy leads to persisting immune responses over time, even in the IL-6 knockout mouse background. Accordingly, yeast-based immunotherapeutics additionally offer the opportunity to modulate the persistence of Treg in an individual.

Based on the discoveries described herein, the invention contemplates that yeast-based immunotherapy has at least six modes of action, which are not mutually exclusive, with value for a variety of types of immunotherapy, including without limitation, anti-fungal, anti-viral and anti-tumor immunotherapy. First, yeast-based immunotherapeutic compositions generate antigen-specific $CD8^+$ positive T cells that directly lyse the tumor. These $CD8^+$ T cells can be generated in at least two ways, representing two of the six modes of action referenced above: 1) the cross presentation of exogenously phagocytized yeast leading to the direct activation of antigen specific $CD8^+$ T cells; and 2) the generation of TH1 cells via IL-12-dependent, type I interferon-independent mechanisms that produce cytokines such as IL-2 that are essential for the sustained function of $CD8^+$ T cells. A third mode of action is the yeast-based generation of cells producing IL-21. IL-21 can function to enhance the survival of CD8 T cells and thus promotes a more durable immune response. A fourth mode of action of yeast-based immunotherapy is the generation of TH17 cells that convert to conditions that favor the generation of TH1 as the yeast-immunotherapy induced inflammation is ameliorated and recruited neutrophils that have not phagocytosed yeast die and in turn, are phagocytized themselves. These first four mechanisms all benefit from a skewing of the immune response from TH17 to TH1, which is described in more detail below. Fifth, TH17 T cells produce IL-17 with either direct tumoricidal activity or indirect tumoricidal activity due to the recruitment of neutrophils, and therefore, both the TH17 and the TH1 response are beneficial to cancer. This mode of action indicates that a more directed temporal modulation of these pathways can improve anti-cancer efficacy. Sixth, TH17 compete with Treg for TGFβ and thus modulate immunosuppressive Treg activity (i.e., reduce Treg activity). This is another benefit to the TH17 response induced by yeast-based immunotherapy, which can be leveraged to enhance the efficacy of immunotherapy in a subject. Accordingly, yeast-based immunotherapy provides a multi-pathway approach to addressing an infection or disease with immunotherapy, and this pathway can be further modified to skew a response in one direction or another based on the desired therapeutic approach and the individual to be treated.

Accordingly, the invention provides methods for modulating the immune response using yeast-based immunotherapy, depending on the target and the disease indication, as well as the general propensity of the individual to respond more vigorously via one TH cell pathway or the other after administration of yeast-based immunotherapy composition. The TH1 pathway is associated prominently with the generation of antigen-specific cell-mediated immunity and the TH17 pathway is associated with the generation of anti-fungal properties, anti-tumor properties, and neutralization of Treg. The roles of IL-6 and Type I interferon, as well as engagement of CD40 (or activation of dendritic cells), are also important in this process. By understanding the interplay among these immunomodulatory agents in the generation of yeast-based immunotherapy-mediated TH1 and TH17 responses, the inventors propose that these pathways can be modulated to more precisely design specific therapeutic outcomes, and thus enhance the power of the yeast-based immunotherapy platform. In addition, individuals can also be screened to determine how best to be treated using yeast-based immunotherapy (e.g., depending on the disease to be treated, the type of immune response that is desired, and the propensity of the individual to mount an immune response that is skewed toward or away from TH17 responses), and such immunotherapy can be customized accordingly. In short, yeast-based immunotherapy represents a mechanism for therapeutic immunomodulation using a single product that activates two CD4 pathways, and given the discoveries described herein, one can now take advantage of this knowledge to further modulate immune responses.

Given the inventors' demonstration herein that yeast-based immunotherapeutics (e.g., TARMOGEN® products) provoke a TH17 phenotype, which includes expression of retinoid-related orphan receptor (ROR), and particularly, RORγt, expression by TH17 T cells, without being bound by theory, the inventors believe that one explanation for the observation that approximately 25% of patients are unable to mount T cell proliferative responses to yeast-based immunotherapeutics in vitro, even after priming, may reflect a persistence of the TH17 subset, suggesting that these patients exhibit an "over-commitment" to the anti-proliferative TH17 response. A persistent TH17 response could prevent or inhibit such patients from effectively "converting" to or mounting TH1 responses and antigen-specific immunity, including $CD8^+$ T cell responses. In some of these individuals, the deficiency may be a deficiency in the ability to generate type I interferon-dependent T cell responses as a result of a skewing toward a TH17 phenotype and for these individuals, yeast-based immunotherapy is expected to be an advantage and a means by which such individuals can now mount an efficacious CD8 response.

In others of such individuals, a skewing toward a stronger TH17 response may actually compromise their ability to produce effective CD8+ responses to yeast-based immunotherapy (i.e., the response may be so skewed toward a TH17 response that conversion back to a TH1 response is limited), and such patients may require additional therapeutic approaches to downregulate or temper the yeast-induced TH17 response as described herein. As noted, it is typically not desirable to block or shut down a TH17 response altogether, as the multi-pathway response elicited by yeast-based immunotherapy is believed to be therapeutically beneficial. Alternatively, a persistent TH17 response may actually enhance the clinical efficacy of such patients' immune response or simply represent an immune response that is different from the TH1 response, but that is also clinically efficacious, at least under certain conditions. Indeed, there should be value in generating concomitantly a TH17 and TH1 response wherein the TH17 may ultimately improve TH1 responses by targeting Treg, as well as produce cytokines such as IL-21 that promote durable memory $CD8^+$ responses. In addition, in the case of fungal disease, a TH17-dominant immune response would be preferred, and additional durable CD8+ memory responses are desirable. In any event, the present invention can be used to effectively modulate an individual's immune response toward one or the other type of response in order to improve or enhance efficacy of a yeast-based immunotherapeutic composition depending on what type or types of immune response will be more effective for a given target or disease. Indeed, the invention provides the opportunity to modulate the immune response to provide a TH17 and then a TH1 response in a controlled temporal manner, for disease states where both types of immune responses can play a beneficial role.

A Phase 1, open-label, dose escalation safety trial for a yeast-based immunotherapy (TARMOGEN® therapy, GlobeImmune, Inc., Louisville, Colo.) known as GI-4000-01 in colorectal and pancreas cancer subjects had five long term survivors. All five long term survivors were responders to yeast-based immunotherapy in vitro, as measured by T cell proliferation, for example, which is consistent with the ability of such patients to effectively convert from a TH17 response to a TH1 response. Regardless, and without being bound by theory, the present inventors believe that the proliferative response to such immunotherapy in vitro is a useful determinant of who might benefit most from such therapy and in what disease conditions, and/or can be used to identify those patients for whom additional treatments may be required or advised in order to benefit the most from yeast-based immunotherapy.

Given that TH17 cells and IL-17 have been associated with anti-tumor activity, yeast-based immunotherapy is expected to be intrinsically tumoricidal through the ability of such compositions as fungi to induce TH17. While the TH17-mediated tumoricidal mechanism is presently not generally understood, one possibility is that IL-17 has direct tumoricidal activity. IL-17 may also indirectly have anti-tumor activity by recruiting neutrophils or interfering with Treg development. Regardless, these mechanisms might be considered to occur independently of the antigen presented by the yeast-based immunotherapy. However, as mentioned previously, the inflammation induced by the yeast-based immunotherapy, once ameliorated, would swing the balance from TH17 to TH1 and thus cause the promulgation of CD8+ T cells. Therefore, certain disease states, such as cancer, may benefit from both TH17-mediated anti-tumor activity and Treg dysfunction, as well as the generation of antigen-specific CD8+ T cells.

Accordingly, the compositions and methods of the invention can be applied to different disease states and individuals in different ways. For example, in a subject that has cancer, in one aspect, an individual may benefit from the TH17-inducing activity of a yeast-based immunotherapeutic as well as the eventual TH1-mediated immune response induced by yeast. Therefore, in one aspect, the yeast-based immunotherapeutic is administered initially without further modification, or alternatively, the yeast-based immunotherapeutic is administered and at a later timepoint, after the TH17-mediated anti-tumor effects are induced, a TH1 response is upregulated by administration of an agent that enhances the shift from a TH17 to a TH1 response (e.g., an agent that down-regulates TH17 and/or upregulates TH1). Alternatively, since anti-tumor effects of TH1 and CD8+ immune responses are believed to be an important part of tumor ablation or control, in some aspects of the invention, the yeast-based immunotherapeutic is administered concurrently with a TH17-downregulating and/or TH1-upregulating agent, so as to enhance the shift to a TH1 response more rapidly or more definitively than in the absence of such an agent. In addition, in individuals who are generally non-responsive or only partially responsive to yeast-based immunotherapy in a given disease (defined below), administration of an agent that modulates TH17 response and/or modulates TH1 responses concurrently with our after initiation of yeast-based immunotherapy may allow such individuals to generate a more beneficial immune response with yeast-based immunotherapy, particularly in such individuals who are predisposed to "overcommit" to the TH17 pathway, or perhaps those who are "weaker" TH17 responders, at least in certain diseases or conditions. Yeast may also be genetically engineered and/or manufactured in a manner that achieves the goal of a modified TH17 or TH1 response, for example.

Indeed, the invention is generally useful for an individual who is a non-responder or a partial responder to yeast-based immunotherapy (with respect to a given disease or condition), in that by administering an agent that downregulates TH17 responses and/or upregulates TH1 responses in the individual who, for example, is unable or less able than the normal population to shift from a TH17 to a TH1 response, or who is unable or less able than the normal population to mount an interferon-independent immune response, the utility of yeast-based immunotherapy can be realized in that individual, particularly in individuals suffering from cancer or a viral infection or disease. The invention allows for the "personalization" of yeast-based immunotherapy to treat a specific person and/or a specific disease state in a manner that is expected to be more efficacious. Similarly, administration of an agent that upregulates TH17 responses in an individual, particularly in an individual who has a weaker than normal TH17 response or is a "non-responder" or "partial responder" to immunotherapy for fungal infections, may enhance the immune response by that individual to fungal infections, assisting the subject in reducing a symptom of the fungal infection.

According to the present invention, a "non-responder" to yeast-based therapy is defined with respect to the particular disease or condition to be treated using yeast-based immunotherapy, and refers to a subject who does not produce an immune response to a yeast-based immunotherapy that is sufficiently efficacious to reduce or ameliorate at least one symptom of that disease against which the immunotherapy is targeted. A "partial non-responder" may have some response to yeast-based immunotherapy that results in a partial therapeutic result in a given disease or condition, but the response may be sub-optimal or could be improved to gain a better therapeutic response. Similarly, a "non-responder" may have a response to yeast-based immunotherapy (e.g., a strong TH17 response), but is unable to produce a TH1-mediated CD8+ response that is effective against a viral infection or cancer, for example. Such individuals may also have other deficiencies, such as an inability to produce an interferon-dependent immune response, thus limiting the ability of their immune system to handle many types of infections or diseases. In other words, while most subjects are expected to produce an immune response to immunization with a yeast-based immunotherapy composition, the type of immune response elicited in the subject may vary as described herein, and the particular response elicited in a subject may or may not be effective to reduce or ameliorate a symptom of the disease or condition targeted by the immunotherapy. The present invention proposes that the TH17 cell population regulates the responsiveness of the individual to different diseases in the context of yeast-based immunotherapy. For example, as mentioned above, a subject may have a strong TH17 immune response to immunization with a yeast-based immunotherapy composition, but may not be able to readily convert such response to an effective TH1 response. Such a subject may therefore be a "responder" with respect to yeast-based immunotherapy for a fungal disease, but a non-responder or a partial non-responder with respect to yeast-based immunotherapy for a viral disease, such as hepatitis, which is believed to require a TH1-mediated CD8+ response for efficacy. Therefore, the term "responder" or "non-responder" are used with respect to the disease to be treated, rather than whether or not any immune response is elicited in a subject in response to administration of yeast-based immunotherapy.

Accordingly, another manner of characterizing individuals is with respect to the TH17 immune response that the individual produces in response to immunotherapy. Certain individuals may be "stronger" TH17 responders, meaning that they produce a vigorous or stronger TH17-type response to yeast-based immunotherapy as compared to the majority of the population or as compared to a person who has a normal or expected TH17 response (e.g., this may be a normal or healthy control person in the case of a subject who has a given disease or condition). Typically, a TH17 response is determined by measuring the amount of IL-17 produced in vitro by CD4+ T cells isolated from a subject or by measuring the levels/numbers of IL-17-producing CD4+ T cells (TH17 cells) isolated from a subject relative to the levels/numbers of all CD4+ T cells from the same source (e.g., peripheral blood, lung, spleen, lymph node, etc.) in the subject. In some cases, the level of expression of retinoid-related orphan receptor (ROR), and specifically RORγt, a marker for TH17 cells, is evaluated in the population of CD4+ T cells isolated from the subject as an indicator of the level of TH17 cells in the subject. The isolated cells can be evaluated before and after contact with yeast-based immunotherapy composition, where the contact with yeast-based immunotherapy typically occurs in vitro (but may occur in vivo, in some circumstances), and/or in comparison to a number of positive and negative controls (e.g., a TLR agonist, cytokines, buffers alone, samples from populations of individuals or other individuals with defined immune responses to yeast-based immunotherapy, etc.). T cell proliferation assays, cytokine assays and other biomarker assays are well known in the art. Proliferation is typically measured in vitro, by obtaining T cells from the subject and exposing them to antigen presenting cells that have been contacted with the yeast-based immunotherapeutic composition, and measuring proliferation of the T cells, such as by using a radioisotope or colorimetric detection method. Cytokine assays include, but are not limited to, enzyme-linked immunosorbant assay (ELISA), radioimmunoassay (RIA), immunohistochemical analysis, immunoblotting, fluorescence activated cell sorting (FACS), and flow cytometry. mRNA expression levels can be detected using a variety of assays known in the art, including, but not limited to, PCR, reverse transcriptase-PCR (RT-PCR), in situ PCR, in situ hybridization, and Northern blot. Strong TH17 responders produce statistically significantly ($p>0.05$) more IL-17 and/or have more IL-17-producing CD4+ T cells (TH17 cells) than the average level of IL-17 production or average level/number of TH17 cells in CD4+ T cells isolated from the same source (e.g., peripheral blood) from a population of individuals who are generally healthy or "normal" (i.e., as a group, are not experiencing a particular disease or condition), in response to yeast-based immunotherapy. IL-17 levels can be measured by a variety of in vitro assays known in the art, and can be measured by evaluating IL-17 protein or mRNA amounts. Similarly, RORγt levels can be measured using techniques known in the art for measuring this transcription factor.

Certain individuals may be "weaker" TH17 responders, meaning that they produce a modest or weaker TH17-type response to immunotherapy as compared to the majority of the population. It is anticipated that individuals will fall across a spectrum of TH17 responses, and so the ability to modify the immune response to yeast-based immunotherapy will be beneficial in personalizing therapy. Weak TH17 responses can be measured as described above, except that a "weak" TH17 responder will produce statistically significantly ($p>0.05$) less IL-17 or have fewer IL-17-producing CD4+ T cells (TH17 cells) than the average levels of IL-17 production or average levels of TH17 cells in CD4+ T cells isolated from the same source (e.g., peripheral blood) from a population of individuals who are generally healthy or "normal" (i.e., as a group, are not experiencing a particular disease or condition).

In an individual who has a viral infection or viral disease (e.g., a viral-associated disease), it is generally desirable to achieve the benefits of a TH1 and CD8+ immune response, particularly in individuals who are resistant to interferon-driven therapy, and so with this type of infection or disease (which is expected to be applicable to other intracellular pathogens), the yeast-based immunotherapeutic is administered concurrently or sequentially with an agent that enhances the shift from a TH17 to a TH1 response (e.g., an agent that downregulates TH17 and/or upregulates TH1), or alternatively, the yeast are modified by genetic engineering or manufacturing processes to enhance the ability of the yeast to induce a TH1-mediated immune response.

In an individual who has a fungal infection or a disease associated with an extracellular pathogen and some intracellular pathogens, it is generally desirable to achieve the benefits of a TH17 immune response to control the infection or disease, and so in these embodiments, the yeast-based immunotherapeutic is administered concurrently or sequentially with an agent that enhances a TH17 response or alternatively, the yeast are modified by genetic engineering or manufacturing processes to increase the ability of the yeast to enhance a TH17-mediated immune response. Even in fungal disease, however, there is a benefit to ultimately producing a durable CD8+ T cell response and to allowing a proinflammtory response to diminish and so, in this embodiment, it is not desirable to completely block the formation of a TH1 response. In one aspect, when it is desirable to allow the immune response to proceed to a TH1-mediated response, the agent may be omitted or halted from the therapeutic protocol, a TH1-inducing agent can be administered, and/or if the yeast had been genetically modified or manufactured to enhance TH17 responses, yeast that are not treated in such a manner can be utilized for boosters. As in other embodiments, the extent to which the TH17 response should be enhanced for the treatment of fungal disease will depend in part on the ability of the individual to mount a TH17 response when administered yeast-based immunotherapy. If the individual has a weaker TH17 response than the general population, the use of TH17-enhancing agents may be particularly useful.

Methods of the Invention

The invention includes a variety of methods to modulate an immune response using yeast-based immunotherapy. One embodiment of the invention relates to a method to enhance the immunotherapeutic properties of a yeast-based immunotherapy composition, by (a) administering to a subject a yeast-based immunotherapy composition; and (b) administering to the subject at least one agent that modulates the production and/or survival of TH17 CD4+ T cells. In one aspect of the invention, the subject is a non-responder or partial responder to yeast-based immunotherapy with respect to one or more symptoms associated with a disease. Indeed, it is these subjects who are likely to benefit the most from modified yeast-based immunotherapy as described herein.

One embodiment of the invention relates to a method to enhance TH1-mediated immune responses to yeast-based immunotherapy. The method includes the steps of (a) administering to a subject a yeast-based immunotherapy composition; and (b) administering to the subject at least one agent that downregulates the production and/or survival of TH17 CD4+ T cells. Another embodiment of the invention relates to a method to treat cancer or ameliorate one or more symptoms thereof, the method including (a) administering to a subject a yeast-based immunotherapy composition; and (b) administering to the subject at least one agent that downregulates the production and/or survival of TH17 CD4+ T cells. Yet another embodiment of the invention relates to a method to treat a viral infection, or to ameliorate one or more symptoms thereof, the method including (a) administering to a subject a yeast-based immunotherapy composition; and (b) administering to the subject at least one agent that downregulates the production and/or survival of TH17 CD4+ T cells. In one aspect of this embodiment, the viral infection is a hepatitis virus infection, including, but not limited to, hepatitis B virus or hepatitis C virus. Another embodiment of the invention relates to a method to enhance $CD8^+$ T cell responses to yeast-based immunotherapy, as compared to administration of the yeast-based immunotherapy composition alone. The method includes the steps of (a) administering to a subject a yeast-based immunotherapy composition; and (b) administering to the subject at least one agent that downregulates the production and/or survival of TH17 CD4+ T cells. Agents suitable for use in these embodiments of the invention are described in detail below.

According to the invention, TH17 T cells are defined as a subset of T helper CD4+ T cells that produce interleukin-17 (IL-17) as well as IL-21 and IL-22. TH17 T cells are considered to be distinct from the other known T helper subsets Th1, Th2 and Treg T cells. The production and/or survival of TH17 cells are associated with various cytokines/growth factors, including, but not limited to, transforming growth factor beta (TGFβ), interleukin-1β (IL-1β), interleukin 6 (IL-6), interleukin 21 (IL-21), interleukin-22 (IL-22) and interleukin 23 (IL-23). In addition, transcription factors participating in the differentiation of TH17 are the retinoic-acid-receptor-related orphan receptors alpha (RORα) and RORγt, and STAT3. TH17 are believed to become activated and differentiate in the presence of TGFβ, IL-6, and perhaps IL-1β, while IL-21 may represent an IL-6 independent activator of TH17 cells. Activation of ROR-γt also causes expression of the receptor for IL-23, and IL-23 is believed to be required for the differentiation and more particularly, for the expansion and survival of TH17 cells (i.e., T cells that are already committed to the TH17 lineage). IL-17, which is produced by TH17, is involved in the recruitment, activation and migration of neutrophils. IL-17 is also a proinflammatory cytokine that enhances T cell priming and stimulates the production of proinflammatory molecules. Interferon-γ (IFN-γ) is a negative regulator of TH17 differentiation. TH17 cells also produce IL-17F, IL-21 and IL-22.

Another embodiment of the invention relates to a method to treat a disease or condition that benefits from a TH17-mediated immune response, including but not limited to a fungal infection, other infectious diseases, and in some embodiments, cancer. Such a method includes (a) administering to a subject a yeast-based immunotherapy composition; and (b) administering to the subject at least one agent that upregulates the production and/or survival of TH17 cells. Agents suitable for use in these embodiments of the invention are described in detail below.

The invention includes the use of agents that can modulate the production and/or survival of TH17 T cells. According to the present invention, the term "modulate" can be used interchangeably with "regulate" and refers generally to upregulation or downregulation of a particular activity. As used herein, the term "upregulate" can be used generally to describe any of: elicitation, initiation, increasing, augmenting, boosting, improving, enhancing, amplifying, promoting, or providing, with respect to a particular activity. Similarly, the term "downregulate" can be used generally to describe any of: decreasing, reducing, inhibiting, ameliorating, diminishing, lessening, blocking, or preventing, with respect to a particular activity. Accordingly, and by way of example, agents useful for modulating the production and/or survival of TH17 cells can include any agent that downregulates the production and/or survival of TH17 cells in some embodiments, or any agent that upregulates the production and/or survival of TH17 cells in other embodiments. Similarly, also by way of example, agents useful for modulating TH1 responses, can include any agent that downregulates a TH1 response in some embodiments, or any agent that upregulates a TH1 response in other embodiments, or any agent that by modulating Treg and/or TH17 responses, modulates TH1 responses. Agents useful for the various embodiments of the invention are described in detail below.

Various methods of the invention treat a disease or condition by administering compositions of the invention. As used herein, the phrase "treat a disease", or any permutation thereof (e.g., "treated for a disease", etc.) can generally refer to preventing a disease, preventing at least one symptom of the disease, delaying onset of a disease, reducing one or more symptoms of the disease, reducing the occurrence of the disease, and/or reducing the severity of the disease. For example, with respect to cancer, the methods of the invention can result in one or more of: prevention of tumor growth, delay of the onset of disease, reduction of tumor burden and/or tumor mass, reduction of tumor growth, increased survival, improved organ function, and/or improved general health of the individual. With respect to infectious disease and other diseases, the methods of the invention can result in one or more of: prevention of the disease or condition, prevention of infection, delay of the onset of disease or symptoms caused by the infection, increased survival, reduction of pathogen burden (e.g., reduction of viral titer), reduction in at least one symptom resulting from the infection in the individual, reduction of organ or physiological system damage resulting from the infection or disease, improvement in organ or system function, and/or improved general health of the individual.

Yet another embodiment of the invention relates to a method to improve the efficacy of yeast-based immunotherapy in a subject who is a non-responder or partial responder to yeast-based immunotherapy, with respect to one or more symptoms associated with a disease. The method includes administering to the subject at least one agent that modulates the production and/or survival of TH17 cells. The step of administration can occur prior to, in conjunction with, or following administration of a dose of yeast-based immunotherapy composition, to improve the efficacy of the yeast-based immunotherapy in the subject. In one aspect, the disease is a viral disease. In one aspect, the disease is a cancer. In one aspect, the agent downregulates the production and/or survival of TH17 cells. In another aspect of this embodiment, the disease is a fungal disease. In another aspect, the agent upregulates the production and/or survival of TH17 cells. Agents suitable for use in these embodiments of the invention are described in detail below.

Another embodiment of the invention relates to a method to modulate the proliferative response of T cells in a subject to yeast-based immunotherapy, including administering to the subject an agent that modulates the production and/or survival of TH17 cells, the administration being prior to, in conjunction with, or following administration of a dose of yeast-based immunotherapy composition, to modulate the proliferative response of T cells to yeast-based immunotherapy in the subject. In one aspect, the method initiates or increases the proliferative response of T cells in the subject. In another aspect, the method decreases the proliferative response of T cells in the subject. Agents suitable for use in these embodiments of the invention are described in detail below.

Without being bound by theory, the inventors believe that proliferation of a subject's T cells in response to yeast-based immunotherapy is indicative of the subject's ability to mount a TH1 response to yeast-based immunotherapy, where T cell proliferation indicates the presence of TH1 T cells, whereas lower proliferation or lack of proliferation in response to yeast-based immunotherapy is indicative of the subject's commitment or perhaps an overcommitment to TH17 responsiveness and in some instances, a decreased ability to mount a TH1 response to yeast-based immunotherapy. Proliferation is typically measured in vitro, by obtaining T cells from the subject and exposing them to antigen presenting cells that have been contacted with the yeast-based immunotherapeutic composition, and measuring proliferation of the T cells, such as by using a radioisotope or colorimetric detection method. T cell proliferation assays are well known in the art. Proliferation in response to yeast-based immunotherapy does not necessarily indicate whether or not a subject will respond to yeast-based immunotherapy; rather, it is believed to indicate what type of immune response a subject has to yeast-based immunotherapy (e.g., it provides information regarding where the subject lies on the scale of TH17 responsiveness, thus indicating whether additional agents may be indicated to improve the efficacy of the yeast-based immunotherapy depending on the disease or condition to be treated and/or the type of immune response that it is desired to elicit in the subject).

Yet another embodiment of the invention relates to a method to enhance the immunotherapeutic properties of a yeast-based immunotherapeutic composition. Such a method includes the steps of (a) administering to a subject a yeast-based immunotherapy composition; and (b) administering to the subject a second immunotherapy composition, wherein the second immunotherapy composition upregulates the production and/or survival of TH17 cells and/or upregulates the production and/or survival of TH1 cells and/or downregulates the production and/or survival of Tregs. This embodiment of the invention contemplates that various therapeutic compositions and compounds, including immunotherapeutic compositions and compounds, may mimic, complement, enhance, add to, or synergize with the natural immunomodulatory effects of a yeast-based immunotherapeutic compositions described herein. In this embodiment, the method enhances the natural effects of administration of a yeast-based immunotherapeutic through combination with another composition having similar or complementary properties, particularly with respect to immune system activation and/or immune function.

In any of the above-described embodiments of the invention, in one aspect, the agent of may be targeted to an antigen presenting cell or targeted to a T cell.

Other embodiments of the invention include methods to modulate cell-mediated immune responses or modulate the immune responses to yeast-based immunotherapy by manipulating the yeast used in the yeast-based immunotherapy composition, such as by genetic engineering or manufacturing/production methods, in order to change or modulate the type of immune response elicited by the yeast-based immunotherapy compositions. Various methods for producing yeast vehicles useful in the invention are described below, including methods to genetically modify the yeast, any of which may be used to achieve the results described herein. In one aspect, such a method is directed to the upregulation of TH1 immune responses and/or the downregulation of TH17 immune responses. In one aspect, the method is directed to the upregulation of TH17 immune responses and the downregulation of TH1 immune responses. In another aspect, both TH17 and TH1 immune responses are upregulated.

For example, in these embodiments, yeast may be genetically modified to express an agent that is useful for modulating TH17 and/or TH1 responses as described herein. In one aspect, such agents may be secreted by the yeast vehicle that is used to produce the yeast-based immunotherapeutic (or by another yeast vehicle). In one aspect, such agents may be expressed on the yeast surface. In one aspect, the yeast cell wall may be modified by genetic engineering to express agents that interact with cell surface molecules on antigen presenting cells and thereby modulate the way in which the antigen presenting cell is activated and/or modulate the type of innate immune response generated by the antigen presenting cell. In another aspect, the yeast vehicle used to produce the yeast-based therapeutic (or another yeast vehicle) is genetically modified to carry and deliver an agent, such as an siRNA. In one aspect, yeast may be grown under conditions that modify the composition and/or fluidity of the yeast cell wall, thereby exposing, hiding, removing or altering cell wall components (e.g., polysaccharides, glycoproteins, etc.) that influence the type of innate immune response generated by antigen presenting cells that are activated by the yeast.

In one embodiment, the invention includes a method to upregulate TH1-mediated immune responses, including administering to a subject a yeast-based immunotherapy composition, wherein the yeast used to produce the yeast-based immunotherapy composition have been genetically modified or have been produced under conditions that downregulate the ability of the yeast to induce a TH17 immune response in the subject and/or that upregulate the ability of the yeast to induce a TH1 immune response in a subject. Such a method may be useful when the subject has cancer or a viral infection, for example.

In one embodiment, the invention includes a method to downregulate TH1-mediated immune responses or to upregulate TH17 immune responses, including administering to a subject a yeast-based immunotherapy composition, wherein the yeast used to produce the yeast-based immunotherapy composition have been genetically modified or have been produced under conditions that upregulate the ability of the yeast to induce a TH17 immune response in the subject and/or that decrease the ability of the yeast to induce a TH1 immune response in a subject. Such a method may be useful when the subject has a fungal infection or in some cases, cancer, for example.

Another embodiment relates to a method to modulate the immune response produced by a yeast-based immunotherapy composition, including administering to a subject a yeast-based immunotherapy composition, wherein the yeast used to produce the yeast-based immunotherapy composition have been produced under conditions that modify the yeast cell wall so that signaling through a dectin receptor of an antigen presenting cell contacted with the yeast-based immunotherapy composition is increased.

Alternatively, another embodiment relates to a method to modulate the immune response produced by a yeast-based immunotherapy composition, comprising administering to a subject a yeast-based immunotherapy composition, wherein the yeast used to produce the yeast-based immunotherapy composition have been produced under conditions that modify the yeast cell wall so that signaling through a dectin receptor of an antigen presenting cell contacted with the yeast-based immunotherapy composition is decreased.

In these two embodiments of the invention, the dectin receptor can include the dectin-1 receptor or the dectin-2 receptor. In one embodiment, signaling through the dectin-1 receptor is reduced. In another embodiment, signaling through both the dectin-1 and dectin-2 receptor is reduced.

Another embodiment relates to a method to modulate the immune response produced by a yeast-based immunotherapy composition, including administering to a subject a yeast-based immunotherapy composition, wherein the yeast used to produce the yeast-based immunotherapy composition have been produced under conditions that modify the yeast cell wall so that signaling through a mannose receptor of an antigen presenting cell contacted with the yeast-based immunotherapy composition is increased.

Alternatively, another embodiment relates to a method to modulate the immune response produced by a yeast-based immunotherapy composition, comprising administering to a subject a yeast-based immunotherapy composition, wherein the yeast used to produce the yeast-based immunotherapy composition have been produced under conditions that modify the yeast cell wall so that signaling through a mannose receptor of an antigen presenting cell contacted with the yeast-based immunotherapy composition is decreased.

Another embodiment relates to a method to modulate the immune response produced by a yeast-based immunotherapy composition, including administering to a subject a yeast-based immunotherapy composition, wherein the yeast used to produce the yeast-based immunotherapy composition have been produced under conditions that modify the yeast cell wall so that signaling through a DC-SIGN receptor of an antigen presenting cell contacted with the yeast-based immunotherapy composition is increased.

Alternatively, another embodiment relates to a method to modulate the immune response produced by a yeast-based immunotherapy composition, comprising administering to a subject a yeast-based immunotherapy composition, wherein the yeast used to produce the yeast-based immunotherapy composition have been produced under conditions that modify the yeast cell wall so that signaling through a DC-SIGN receptor of an antigen presenting cell contacted with the yeast-based immunotherapy composition is decreased.

Another embodiment of the invention relates to a method to modulate the immune response produced by a yeast-based immunotherapy composition, comprising administering to a subject a yeast-based immunotherapy composition, wherein the yeast used to produce the yeast-based immunotherapy composition have been produced under conditions that reduce or eliminate the exposure of β-glucans on the cell wall surface of the yeast.

Alternatively, another embodiment of the invention relates to a method to modulate the immune response produced by a yeast-based immunotherapy composition, comprising administering to a subject a yeast-based immunotherapy composition, wherein the yeast used to produce the yeast-based immunotherapy composition have been produced under conditions that increase the exposure of β-glucans on the cell wall surface of the yeast.

Another embodiment of the invention relates to a method to modulate the immune response produced by a yeast-based immunotherapy composition, comprising administering to a subject a yeast-based immunotherapy composition, wherein the yeast used to produce the yeast-based immunotherapy composition have been produced under conditions that reduce or eliminate the exposure of mannose or derivatives thereof on the cell wall surface of the yeast.

Another embodiment of the invention relates to a method to modulate the immune response produced by a yeast-based immunotherapy composition, comprising administering to a subject a yeast-based immunotherapy composition, wherein the yeast used to produce the yeast-based immunotherapy composition have been produced under conditions that reduce or eliminate the exposure of mannose or derivatives thereof on the cell wall surface of the yeast.

Yet another embodiment of the invention relates to a method to modulate the immune response produced by a yeast-based immunotherapy composition, comprising administering to a subject a yeast-based immunotherapy composition, wherein the yeast used to produce the yeast-based immunotherapy composition have been produced (e.g., grown or manufactured) under conditions that downregulate the ability of the yeast to induce a TH17-mediated immune response.

Alternatively, the invention also includes a method to modulate the immune response produced by a yeast-based immunotherapy composition, comprising administering to a subject a yeast-based immunotherapy composition, wherein the yeast used to produce the yeast-based immunotherapy composition have been produced under conditions that upregulates the ability of the yeast to induce a TH17-mediated immune response.

The invention also includes a method to produce a yeast-based immunotherapy composition that enhances TH1-mediated immune responses, comprising genetically engineering the yeast used to produce the yeast-based immunotherapy composition in a manner effective to downregulate a TH17-mediated response in a subject to whom the yeast-based immunotherapy composition is administered. Various methods for genetically modifying yeast are known in the art and described herein. For example, methods that result in the expression by the yeast of one or more agents described herein (e.g., recombinant expression) are contemplated.

Another embodiment of the invention includes a method to produce a yeast-based immunotherapy composition that enhances TH1-mediated immune responses, comprising growing or manufacturing (producing) the yeast used in the yeast-based immunotherapy composition under conditions effective to downregulate a TH17-mediated response in a subject to whom the yeast-based immunotherapy composition is administered. For example, methods of growing the yeast to modify the fluidity and/or composition of the outer surface of the yeast cell wall, such as by growing the yeast at a neutral pH, are encompassed by this embodiment of the invention.

Agents Useful in the Methods of the Invention

Various agents are contemplated herein for use in the methods of the invention. The agents are combined with yeast-based immunotherapeutics for use in the methods of the invention, either in a single composition, in a separate composition(s) to be administered together with or concurrently with a yeast-based immunotherapeutic, or in a composition(s) to be administered prior to, after, or in an alternating or other specialized schedule with, a yeast-based immunotherapeutic. Such agents include any moiety (chemical or biologic) that can be administered in conjunction with a yeast-based immunotherapy composition as described herein and have the desired modulatory effect. For example, an agent can include, but is not limited to, a protein, a peptide, an antibody or antigen-binding portion thereof, a small molecule (e.g., a drug or chemical compound); polynucleotides and nucleic acid binding agents (e.g., probes, siRNA, anti-sense molecules, ribozymes), a biological agonist or antagonist of a soluble ligand or its receptor, a biological agonist or antagonist of a cell surface molecule/receptor; lipids and derivatives thereof, polysaccharides and derivatives thereof, or aptamers, as well as homologues or derivatives of such agents and combinations of such agents. In one embodiment, the yeast used to produce the yeast-based immunotherapy composition has been engineered to carry or express the agent. The agents include, but are not limited to, agents that modulate the production and/or survival of TH17 cells and/or modulate the production and/or survival of TH1 cells and/or modulate the production and/or survival of Treg. For example, such agents include, but are not limited to, any of the agents described in more detail below, including without limitation, cytokines, chemokines, antibodies and antigen-binding fragments thereof (including but not limited to anti-cytokine antibodies, anti-cytokine receptor antibodies, anti-chemokine antibodies), receptors, ligands, polysaccharides, immunomodulators, anti-inflammatory agents, pro-inflammatory agents, vitamins, nucleic acid binding agents, fusion proteins, homologues or derivatives of any of such agents or other vaccines or immunotherapeutic compounds, agents or compositions, and other biological response modifiers.

In one aspect of the invention, an agent useful in a method of the invention together with a yeast-based immunotherapeutic is capable of downregulating the production and/or survival of TH17 cells. One type of agent useful for downregulating the production or survival of TH17 cells includes, but is not limited to, an agent that downregulates the expression and/or activity of a cytokine or its receptor, that is associated with the development, activation, differentiation and/or survival of a TH17 T cell. Such cytokine includes, but is not limited to, IL-1 (including IL-1β), IL-6, IL-17, IL-21, IL-22 and/or IL-23. Another type of agent useful for downregulating the production or survival of TH17 cells includes an agent that upregulates the expression or activity of a cytokine or its receptor that is associated with inhibition of TH17 cell development, activation, differentiation and/or survival, such as IL-25 or IL-27. Other suitable agents useful for downregulating the production and/or survival of TH17 cells include, but are not limited to, small molecules including immunomodulators, anti-fungal agents, antibiotics, anti-inflammatory agents, and vitamins, including without limitation, Vitamin A or Vitamin D.

In another aspect of the invention, an agent useful in a method of the invention is capable of upregulating TH1 development, activation, differentiation and/or survival. Such agents can include, but are not limited to, type I interferons (e.g., IFN-α), type II interferons (e.g., IFN-γ), IL-12, anti-inflammatory agents, CD40L, anti-CD40, lymphocyte-activation gene 3 (LAG3) protein and/or IMP321 (T-cell immunostimulatory factor derived from the soluble form of LAG3). These agents may be used alone or in combination with other agents described herein, such as with agents that upregulate or downregulate TH17 production or survival and in some embodiments, such agents may be one in the same.

In another aspect of the invention, an agent useful in a method of the invention is capable of upregulating the production and/or survival of TH17 cells. One type of agent useful for upregulating the production or survival of TH17 cells includes an agent that upregulates (which may include initiating or sustaining in addition to increasing) the expression and/or activity of a cytokine or its receptor that is associated with the development, activation, differentiation and/or survival of a TH17 T cell, such cytokine including, but not limited to, IL-1, IL-6, IL-17, IL-21, IL-22 and/or IL-23. Another type of agent useful for upregulating the production or survival of TH17 cells includes an agent that downregulates the expression or activity of a cytokine or its receptor that is associated with inhibition of TH17 cell development, activation, differentiation and/or survival, such as, but not limited to, IL-25 OR IL-27. Other suitable agents for upregulating the production and/or survival of TH17 cells include, but are not limited to, fungal products and pro-inflammatory agents.

In another aspect of the invention, an agent useful in a method of the invention is capable of downregulating TH1 development, activation, differentiation and/or survival. Such agents can include, but are not limited to, agents that downregulate the expression or activity of type I interferons (e.g., IFN-α), type II interferons (e.g., IFN-γ), or IL-12. These agents may be used alone or in combination with other agents described herein, such as agents that upregulate or downregulate TH17 production or survival and in some embodiments, such agents may be one in the same.

In another aspect of the invention, an agent useful in a method of the invention is any agent that can mimic, complement, enhance, add to, synergize with, or in some aspects, inhibit or block, one or more natural immunomodulatory effects of yeast-based immunotherapeutics, particularly with respect to any one or more of the TH17, TH1 and Treg modulating abilities of yeast-based immunotherapeutics. Such agents include agents or combinations thereof that: (a) generate $CD8^+$ T cells by inducing cross-presentation of antigens and/or inducing cytokines that support the development and/or activation of $CD8^+$ T cells, (b) support or enhance the production and/or survival of TH17 cells which produce IL-17 (c) support or enhance the production and survival of TH1, and/or (d) inhibit Treg activity.

Such agents may include, but are not limited to, cytokines (such as those described previously herein for use in modulating TH17 and/or TH1 immune responses), chemokines, hormones, lipidic derivatives, peptides, proteins, polysaccharides, small molecule drugs, antibodies and antigen binding fragments thereof (including, but not limited to, anti-cytokine antibodies, anti-cytokine receptor antibodies, anti-chemokine antibodies), vitamins, polynucleotides, nucleic acid binding moieties, aptamers, and growth modulators. Such agents include without limitation agents that modulate a TH17 response, a TH1 response, and/or a Treg response. Some suitable agents include, but are not limited to, IL-1 or agonists of IL-1 or of IL-1R, anti-IL-1 or other IL-1 antagonists; IL-6 or agonists of IL-6 or of IL-6R, anti-IL-6 or other IL-6 antagonists; IL-12 or agonists of IL-12 or of IL-12R, anti-IL-12 or other IL-12 antagonists; IL-17 or agonists of IL-17 or of IL-17R, anti-IL-17 or other IL-17 antagonists; IL-21 or agonists of IL-21 or of IL-21R, anti-IL-21 or other IL-21 antagonists; IL-22 or agonists of IL-22 or of IL-22R, anti-IL-22 or other IL-22 antagonists; IL-23 or agonists of IL-23 or of IL-23R, anti-IL-23 or other IL-23 antagonists; IL-25 or agonists of IL-25 or of IL-25R, anti-IL-25 or other IL-25 antagonists; IL-27 or agonists of IL-27 or of IL-27R, anti-IL-27 or other IL-27 antagonists; type I interferon (including IFN-α) or agonists or antagonists of type I interferon or a receptor thereof; type II interferon (including IFN-γ) or agonists or antagonists of type II interferon or a receptor thereof; anti-CD40, CD40L, lymphocyte-activation gene 3 (LAG3) protein and/or IMP321 (T-cell immunostimulatory factor derived from the soluble form of LAG3), anti-CTLA-4 antibody (e.g., to release anergic T cells); T cell co-stimulators (e.g., anti-CD137, anti-CD28, anti-CD40); alemtuzumab (e.g., CamPath®), denileukin diftitox (e.g., ONTAK®); anti-CD4; anti-CD25; anti-PD-1, anti-PD-L1, anti-PD-L2; agents that block FOXP3 (e.g., to abrogate the activity/kill CD4+/CD25+ T regulatory cells); Flt3 ligand, imiquimod (Aldara™), granulocyte-macrophage colony stimulating factor (GM-CSF); granulocyte-colony stimulating factor (G-CSF), sargramostim (Leukine®); hormones including without limitation prolactin and growth hormone; Toll-like receptor (TLR) agonists, including but not limited to TLR-2 agonists, TLR-4 agonists, TLR-7 agonists, and TLR-9 agonists; TLR antagonists, including but not limited to TLR-2 antagonists, TLR-4 antagonists, TLR-7 antagonists, and TLR-9 antagonists; anti-inflammatory agents and immunomodulators, including but not limited to, COX-2 inhibitors (e.g., Celecoxib, NSAIDS), glucocorticoids, statins, and thalidomide and analogues thereof including IMiD™s (which are structural and functional analogues of thalidomide (e.g., REVLIMID® (lenalidomide), ACTIMID® (pomalidomide)); proinflammatory agents, such as fungal or bacterial components or any proinflammatory cytokine or chemokine; immunotherapeutic vaccines including, but not limited to, virus-based vaccines, bacteria-based vaccines, or antibody-based vaccines; and any other immunomodulators, immunopotentiators, anti-inflammatory agents, pro-inflammatory agents, and any agents that modulate the number of, modulate the activation state of, and/or modulate the survival of antigen-presenting cells or of TH17, TH1, and/or Treg cells. Any combination of such agents is contemplated by the invention, and any of such agents combined with or administered in a protocol with (e.g., concurrently, sequentially, or in other formats with) a yeast-based immunotherapeutic is a composition encompassed by the invention. Such agents are well known in the art. These agents may be used alone or in combination with other agents described herein, such as agents that upregulate or downregulate TH17 or TH1 production or survival and in some embodiments, such agents may be one in the same.

The invention expressly includes, but is not limited to, any of the following specified combinations: a yeast-based immunotherapeutic and IL-1 or an agonist of IL-1 or of IL-1R; a yeast-based immunotherapeutic and anti-IL-1 or other IL-1 antagonists; a yeast-based immunotherapeutic and IL-6 or agonists of IL-6 or of IL-6R; a yeast-based immunotherapeutic and anti-IL-6 or other IL-6 antagonists; a yeast-based immunotherapeutic and IL-12 or agonists of IL-12 or of IL-12R; a yeast-based immunotherapeutic and anti-IL-12 or other IL-12 antagonists; a yeast-based immunotherapeutic and IL-17 or agonists of IL-17 or of IL-17R; a yeast-based immunotherapeutic and anti-IL-17 or other IL-17 antagonists; a yeast-based immunotherapeutic and IL-21 or agonists of IL-21 or of IL-21R; a yeast-based immunotherapeutic and anti-IL-21 or other IL-21 antagonists; a yeast-based immunotherapeutic and IL-22 or agonists of IL-22 or of IL-22R; a yeast-based immunotherapeutic and anti-IL-22 or other IL-22 antagonists; a yeast-based immunotherapeutic and IL-23 or agonists of IL-23 or of IL-23R; a yeast-based immunotherapeutic and anti-IL-23 or other IL-23 antagonists; a yeast-based immunotherapeutic and IL-25 or agonists of IL-25 or of IL-25R; a yeast-based immunotherapeutic and anti-IL-25 or other IL-25 antagonists; a yeast-based immunotherapeutic and IL-27 or agonists of IL-27 or of IL-27R; a yeast-based immunotherapeutic and anti-IL-27 or other IL-27 antagonists; a yeast-based immunotherapeutic and type I interferon (including IFN-α) or agonists or antagonists of type I interferon or a receptor thereof; a yeast-based immunotherapeutic and type II interferon (including IFN-γ) or agonists or antagonists of type II interferon or a receptor thereof; a yeast-based immunotherapeutic and type III interferon (including IFN-λ1, IFN-λ2, IFN-λ3) or agonists or antagonists of type III interferon or a receptor thereof; a yeast-based immunotherapeutic and anti-CD40; a yeast-based immunotherapeutic and CD40L; a yeast-based immunotherapeutic and LAG3 or IMP321; a yeast-based immunotherapeutic and anti-CTLA-4; a yeast-based immunotherapeutic and anti-CD137; a yeast-based immunotherapeutic and anti-CD28; a yeast-based immunotherapeutic and alemtuzumab (e.g., CamPath®); a yeast-based immunotherapeutic and denileukin diftitox (e.g., ONTAK®); a yeast-based immunotherapeutic and anti-CD4; a yeast-based immunotherapeutic and anti-CD25; a yeast-based immunotherapeutic and anti-PD-1; a yeast-based immunotherapeutic and anti-PD-L1; a yeast-based immunotherapeutic and anti-PD-L2; a yeast-based immunotherapeutic and one or more agents that block FOXP3; a yeast-based immunotherapeutic and Flt3 ligand; a yeast-based immunotherapeutic and Vitamin A; a yeast-based immunotherapeutic and Vitamin D; a yeast-based immunotherapeutic and imiquimod (Aldara™); a yeast-based immunotherapeutic and granulocyte-macrophage colony stimulating factor (GM-CSF); a yeast-based immunotherapeutic and granulocyte-colony stimulating factor (G-CSF); a yeast-based immunotherapeutic and sargramostim (Leukine®); a yeast-based immunotherapeutic and prolactin; a yeast-based immunotherapeutic and growth hormone; a yeast-based immunotherapeutic and one or more TLR-2 agonists; a yeast-based immunotherapeutic and one or more TLR-4 agonists; a yeast-based immunotherapeutic and one or more TLR-7 agonists; and a yeast-based immunotherapeutic and one or more TLR-9 agonists; a yeast-based immunotherapeutic and one or more TLR-2 antagonists; a yeast-based immunotherapeutic and one or more TLR-4 antagonists; a yeast-based immunotherapeutic and one or more TLR-7 antagonists; and a yeast-based immunotherapeutic and one or more TLR-9 antagonists; a yeast-based immunotherapeutic and Celecoxib; a yeast-based immunotherapeutic and one or more NSAIDS; a yeast-based immunotherapeutic and one or more glucocorticoids; a yeast-based immunotherapeutic and one or more statins; a yeast-based immunotherapeutic and thalidomide; a yeast-based immunotherapeutic and REVLIMID® (lenalidomide); a yeast-based immunotherapeutic and ACTIMID® (pomalidomide)); a yeast-based immunotherapeutic and one or more fungal components; a yeast-based immunotherapeutic and one or more bacterial components; a yeast-based immunotherapeutic and one or more virus-based vaccines; a yeast-based immunotherapeutic and one or more bacteria-based vaccines; or a yeast-based immunotherapeutic and one or more antibody-based vaccines.

In one embodiment of the present invention, a composition can include biological response modifier compounds, or the ability to produce such modifiers (i.e., by transfection of the yeast vehicle with nucleic acid molecules encoding such modifiers), and in one aspect, such biological response modifiers may be the same as an agent useful in the present invention for modulating TH17, TH1, and/or Treg immune responses. For example, a yeast vehicle can be transfected with or loaded with at least one antigen and at least one biological response modifier compound, or a composition of the invention can be administered in conjunction with at least one biological response modifier. Biological response modifiers include adjuvants and other compounds that can modulate immune responses, which may be referred to as immunomodulatory compounds, as well as compounds that modify the biological activity of another compound or agent, such as a yeast-based immunotherapeutic, such biological activity not being limited to immune system effects. Certain immunomodulatory compounds can stimulate a protective immune response whereas others can suppress a harmful immune response, and whether an immunomodulatory is useful in combination with a given yeast-based immunotherapeutic may depend, at least in part, on the disease state or condition to be treated or prevented, and/or on the individual who is to be treated. Certain biological response modifiers preferentially enhance a cell-mediated immune response whereas others preferentially enhance a humoral immune response (i.e., can stimulate an immune response in which there is an increased level of cell-mediated compared to humoral immunity, or vice versa). Certain biological response modifiers have one or more properties in common with the biological properties of yeast-based immunotherapeutics or enhance or complement the biological properties of yeast-based immunotherapeutics, such as with respect to the effect of yeast-based immunotherapeutics on TH17, TH1, and/or Treg. There are a number of techniques known to those skilled in the art to measure stimulation or suppression of immune responses, as well as to differentiate cell-mediated immune responses from humoral immune responses.

Interleukin-17 (IL-17, also called IL-17A) and a related family member, IL-17F, are produced by the TH subset known as TH17, as well as by natural killer (NK) cells, natural killer T (NKT) cells, γδ T cells, neutrophils, and eosinophils. IL-17 family cytokines are proinflammatory cytokines associated with the immune response to extracellular pathogens and some intracellular pathogens, induces matrix destruction, enhances T cell priming, stimulates the production of proinflammatory molecules, and induces cells to express various cytokines including, TNF-α, IL-10, IL-6, GM-CSF and G-CSF, as well as various chemokines IL-17 and IL-17F are also involved in the recruitment, activation and migration of neutrophils.

Agents useful in the methods of the invention include, in some aspects, agents that downregulate the expression or activity of IL-17 or its receptor(s), including IL-17 and IL-17R antagonists, and in other aspects, agents that upregulate the expression or activity of IL-17 or its receptor(s), including IL-17 and IL-17R agonists. Such agents can be produced and/or selected given the knowledge of the structure and function of IL-17 and IL17 receptors, and a variety of IL-17 agonists and antagonists are known in the art. The nucleic acid sequence and amino acid sequence for IL-17A and IL-17F are known in the art, the human sequences of which are represented herein by SEQ ID NO:2 and SEQ ID NO:3, respectively (human IL-17A) and SEQ ID NO:4 and SEQ ID NO:5, respectively (human IL-17F). In addition, antibodies against IL-17A have been produced, for example, anti-human IL-17A (eBioscience, Inc.); and various antagonists of IL-17A and IL-17F have been described which include antibodies and soluble receptors (see, e.g., WO/2009/136286, WO/2007/038703; WO/2007/147019; WO/2009/082624; WO/2008/134659; or WO/2008/118930). The cognate receptor for IL-17, which is also bound by IL-17F, is IL-17RA (Moseley et al., 2003, Cytokine Growth Factor Rev. 14:155-74).

Interleukin-6 (IL-6) is a proinflammatory cytokine and is secreted by cells of the innate immune system (e.g., macrophages, dendritic cells, monocytes, mast cells, B cells) in response to specific microbial molecules, referred to as pathogen associated molecular patterns (PAMPs), which bind to pattern recognition receptors (PRRs) of the innate immune system. IL-6 binds to its receptor which consists of the IL-6Rα ligand binding chain and the signal-transducing gp130 component, and the receptor complex initiates signal transduction cascade through various transcription factors, Janus kinases and STATs. (See, e.g., Heinrich et al., (2003) Biochem. J. 374: 1-20; or Heinrich et al., (1998) Biochem. J. 334: 297-314).

Agents useful in the methods of the invention include, in some aspects, agents that downregulate the expression or activity of IL-6 or its receptor(s), including IL-6 or IL-6R antagonists, and in other aspects, agents that upregulate the expression or activity of IL-6 or its receptor(s), including IL-6 or IL-6R agonists. Such agents can be produced and/or selected given the knowledge of the structure and function of IL-6 and IL-6 receptor(s), and a variety of IL-6 agonists and antagonists are known in the art. The nucleic acid sequence and amino acid sequence for IL-6 are known in the art, the human sequences of which are represented herein by SEQ ID NO:6 and SEQ ID NO:7, respectively. In addition, antibodies against IL-6 and its receptor have been produced, for example, OPR-003, a fully human anti-interleukin-6 (Vaccinex); humanized anti-human IL-6 receptor (IL-6R) antibody, MRA (Mihara et al., 2001, Clinical Immunol. 98(3): 319-326); anti-human IL-6 (eBioscience, Inc.); CNTO 328 (cCLB8), a human-mouse chimeric MAb to IL-6 (Zaki et al., International Journal of Cancer, 111(4):592-595, 2004); WO/2009/140348; WO/2008/019061. Agonists and antagonists of IL-6 have also been described (see, e.g., WO/2009/095489, WO/2009/060282, WO/2008/071685)

IL-21 is a proinflammatory cytokine that is produced by activated T cells, including TH17 cells, and NKT cells, and can regulate the activity of natural killer (NK) cells and cytotoxic T cells, as well as plays a role in the expansion of activated B cells and isotype class switching. See, e.g., Brandt et al., (2007) Cytokine Growth Factor Rev. 18 (3-4): 223-32, or Leonard and Spolski R. 2005, Nat. Rev. Immunol. 5:688-98, or Korn et al., Annu Rev. Immuno., 2009, 27:485-517. IL-21, together with TGFβ, has been shown to induce the differentiation of TH17 cells, as an alternate pathway to the combination of IL-6 and TGFβ, and therefore may provide positive feed-back in TH17 differentiation, as well as help maintain and amplify TH17 precursors when IL-6 is limiting. IL-21 also induces the expression of ROR γt. The IL-21 receptor is a type I cytokine receptor and shares the common gamma chain with the IL-2 and IL-15 receptors.

Agents useful in the methods of the invention include, in some aspects, agents that downregulate the expression or activity of IL-21 or its receptor(s), including IL-21 or IL-21R antagonists, and in other aspects, agents that upregulate the expression or activity of IL-21 or its receptor(s), including IL-21 or IL-21R agonists. Such agents can be produced and/or selected given the knowledge of the structure and function of IL-21 and IL-21 receptor(s), and a variety of IL-21 agonists and antagonists are known in the art. The nucleic acid sequence and amino acid sequence for IL-21 is known in the art, the human sequences of which are represented herein by SEQ ID NO:8 and SEQ ID NO:9, respectively. In addition, antibodies against IL-21 have been produced, including fully-human anti-IL-21 monoclonal antibody (IL-21 mAb) (see, e.g., anti-human IL-21 by eBioscience, Inc.; WO/2007/111714; WO/2009/047360); and antagonists of IL-21 and the IL-21 receptor have been described (see, e.g., WO/2007/114861; WO/2009/143526; WO/2009/132821; WO/2009/100035; WO/2008/074863; WO/2008/049920).

IL-22 is a proinflammatory cytokine that is secreted by terminally differentiated TH17 cells and plays a role in host defense, inducing epithelial-cell proliferation and the production of anti-microbial proteins. IL-22 signals through the interferon receptor-related proteins CRF2-4 and IL22R. See, e.g., Xie et al., (2000) Journal of Biological Chemistry, Volume 275, page 31335-31339.

Agents useful in the methods of the invention include, in some aspects, agents that downregulate the expression or activity of IL-22 or its receptor(s), including IL-22 or IL-22R antagonists, and in other aspects, agents that upregulate the expression or activity of IL-22 or its receptor(s), including IL-22 or IL-22R agonists. Such agents can be produced and/or selected given the knowledge of the structure and function of IL-22 and IL-22 receptor(s), and a variety of IL-22 agonists and antagonists are known in the art. The nucleic acid sequence and amino acid sequence for IL-22 is known in the art, the human sequences of which are represented herein by SEQ ID NO:10 and SEQ ID NO:11, respectively. In addition, antibodies against IL-22 have been produced (see, e.g., anti-human IL-22 by eBioscience, Inc.; or WO/2007/098170); and antagonists of IL-22 and the IL-22 receptor have been described (see, e.g., WO/2007/126439).

IL-23 is a heterodimeric cytokine consisting of a p40 subunit (shared with IL-12) and a p19 subunit (the IL-23 alpha subunit). IL-23 promotes upregulation of the matrix metalloprotease MMP9, increases angiogenesis and reduces CD8+ T-cell infiltration, and is required for the full and sustained differentiation of TH17 cells. IL-23 may contribute to the stabilization and survival of TH17 cells, and may also promote proinflammatory cytokine expression. IL-23 binds to the IL23 receptor, which is formed by the beta 1 subunit of IL12 (IL12RB1) and an IL23 specific subunit, IL23R. See, e.g., Langowski et al., (2006) Nature 442 (7101): 461-5; Kikly et al., (2006) Curr. Opin. Immunol. 18 (6): 670-5; Oppmann et al., (2000) Immunity 13 (5): 715-25.

Agents useful in the methods of the invention include, in some aspects, agents that downregulate the expression or activity of IL-23 or its receptor(s), including IL-23 or IL-23R antagonists, and in other aspects, agents that upregulate the expression or activity of IL-23 or its receptor(s), including IL-23 or IL-23R agonists. Such agents can be produced and/or selected given the knowledge of the structure and function of IL-23 and IL-23 receptor(s), and a variety of IL-23 agonists and antagonists are known in the art. The nucleic acid sequence and amino acid sequence for the IL-23 p19 and p40 subunits are known in the art, the human sequences of which are represented herein by SEQ ID NO:12 and SEQ ID NO:13, respectively (p19) and SEQ ID NO:14 and SEQ ID NO:15, respectively (p40 subunit). Agonists and antagonists of IL-23 and the IL-23 receptor have been described, which include antibodies (see, e.g., anti-human IL-23 by eBioscience, Inc.; WO/2009/100035; WO/2007/147019; WO/2009/082624; WO/2008/134659).

IL-25 is a cytokine that belongs to the IL-17 family of cytokines (also known as IL-17E) and induces TH2-related cytokines and limits chronic inflammation. IL-25 inhibits TH17 cell functions. See, e.g., Kleinschek et al., J Exp Med 2007; 204: 161-170; Owyang et al., J Exp Med 2006; 203: 843-849.

Agents useful in the methods of the invention include, in some aspects, agents that downregulate the expression or activity of IL-25 or its receptor(s), including IL-25 or IL-25R antagonists, and in other aspects, agents that upregulate the expression or activity of IL-25 or its receptor(s), including IL-25 or IL-25R agonists. Such agents can be produced and/or selected given the knowledge of the structure and function of IL-25 and IL-25 receptor(s), and a variety of IL-25 agonists and antagonists are known in the art. The nucleic acid sequence and amino acid sequence for IL-25 are known in the art, the human sequences of transcript variant 1 of which are represented herein by SEQ ID NO:16 and SEQ ID NO:17, respectively. In addition, antibodies against IL-25 have been described, which include antibodies (see, e.g., WO/2008/129263).

IL-27 is a cytokine that is a member of the IL-12 family and is produced by cells of the innate immune system. IL-27 has been shown to enhance TH1 responses and has anti-inflammatory properties. IL-27 has been shown to be capable of inhibiting TH17 responses independently of its ability to enhance TH1 responses (see, e.g., Batten et al., 2006, Nat. Immunol. 7:929-36; Stumhofer et al., 2006, Nat. Immunol. 7:937-45).

Agents useful in the methods of the invention include, in some aspects, agents that downregulate the expression or activity of IL-27 or its receptor(s), including IL-27 or IL-27R antagonists, and in other aspects, agents that upregulate the expression or activity of IL-27 or its receptor(s), including IL-27 or IL-27R agonists. Such agents can be produced and/or selected given the knowledge of the structure and function of IL-27 and IL-27 receptor(s), and a variety of IL-27 agonists and antagonists are known in the art. The nucleic acid sequence and amino acid sequence for IL-27 is known in the art, the human sequences of which are represented herein by SEQ ID NO:18 and SEQ ID NO:19, respectively. Agonists and antagonists of IL-27 and the IL-27 receptor have been described, which include antibodies (see, e.g., WO/2008/070097; WO/2008/025032; WO/2008/025033).

IL-1β is a proinflammatory cytokine involved in immune defense against infection. IL-1β is produced by macrophages, monocytes and dendritic cells. See, e.g., Dinarello (1994) Faseb J. 8 (15): 1314-25.

Agents useful in the methods of the invention include, in some aspects, agents that downregulate the expression or activity of IL-1β or its receptor(s), including IL-1β or IL-1βR antagonists, and in other aspects, agents that upregulate the expression or activity of IL-1β or its receptor(s), including IL-1β or IL-1βR agonists. Such agents can be produced and/or selected given the knowledge of the structure and function of IL-1β and IL-1β receptor(s), and a variety of IL-1β agonists and antagonists are known in the art. The nucleic acid sequence and amino acid sequence for IL-1β is known in the art, the human sequences of which are represented herein by SEQ ID NO:20 and SEQ ID NO:21, respectively. Agonists and antagonists of IL-1β and the IL-1β receptor have been described, which include antibodies (see, e.g., WO/2007/050607).

IL-12 is a cytokine that plays a role in the differentiation of TH1 cells, and is produced by activated APCs, including DCs. IL-12 is formed from two subunits, denoted p35 and p40. p40 is also a subunit forming the cytokine IL-23, when combined with p19 (see above).

Agents useful in the methods of the invention include, in some aspects, agents that downregulate the expression or activity of IL-12 or its receptor(s), including IL-12 or IL-12R antagonists, and in other aspects, agents that upregulate the expression or activity of IL-12 or its receptor(s), including IL-12 or IL-12R agonists. Such agents can be produced and/or selected given the knowledge of the structure and function of IL-12 and IL-12 receptor(s), and a variety of IL-12 agonists and antagonists are known in the art. The nucleic acid sequence and amino acid sequence for IL-12 is known in the art, the human sequences for the p35 subunit of which are represented herein by SEQ ID NO:22 and SEQ ID NO:23, respectively (the nucleic acid and amino acid sequences for the p40 subunit are described above and are represented herein by SEQ ID NO:14 and SEQ ID NO:15). Agonists and antagonists of IL-12 and the IL-12 receptor have been described, which include antibodies (see, e.g., WO/2008/079359; WO/2006/124662; WO/2005/086835).

TGFβ is a cytokine existing in at least three isoforms that controls the proliferation, cellular differentiation, and other functions in a large variety of cells. TGFβ directs the activation and differentiation of both TH17 and Treg cells. With respect to TH17 activation and differentiation, it does so in conjunction with IL-6 and alternatively, IL-21, and possibly other cytokines TGF-β is required both for the initial induction of IL-17 in naive CD4+ T cells and for the induction of IL-23R, further promoting the maturation of TH17.

Agents useful in the methods of the invention include, in some aspects, agents that downregulate the expression or activity of TGFβ or its receptor(s), including TGFβ or TGFβR antagonists, and in other aspects, agents that upregulate the expression or activity of TGFβ or its receptor(s), including TGFβ or TGFβR agonists. Such agents can be produced and/or selected given the knowledge of the structure and function of TGFβ and TGFβ receptor(s), and a variety of TGFβ agonists and antagonists are known in the art. The nucleic acid sequence and amino acid sequence for TGFβ (isoform 1) is known in the art, the human sequences of which are represented herein by SEQ ID NO:24 and SEQ ID NO:25, respectively. Agonists and antagonists of TGFβ and the TGFβ receptor have been described, which include antibodies (see, e.g., WO/2005/113811).

As used herein, the term "interferon" refers to a cytokine that is typically produced by cells of the immune system and by a wide variety of cells. Interferons assist the immune response by inhibiting viral replication within host cells, activating natural killer cells and macrophages, increasing antigen presentation to lymphocytes, and inducing the resistance of host cells to viral infection. Type I interferons include without limitation interferon-α. Type II interferons include without limitation interferon-γ. Interferons useful in certain of the methods of the present invention include any type I interferon, such as interferon-α, which may include interferon-α2, any type II interferon, which may include interferon-γ, or any type III interferon, which may include interferon-λ1, interferon-λ2, or interferon-λ3, and in one aspect, longer lasting forms of any interferon are contemplated, including, but not limited to, pegylated interferons, interferon fusion proteins (interferon fused to albumin), and controlled-release formulations comprising interferon (e.g., interferon in microspheres or interferon with polyaminoacid nanoparticles).

As discussed above, an agent useful in the invention can include any moiety (chemical or biologic) that can be administered in conjunction with a yeast-based immunotherapy composition as described herein and have the desired modulatory effect on TH17 cells. For example, an agent can include, but is not limited to, a protein, a peptide, an antibody or antigen-binding portion thereof, a small molecule (e.g., a drug or chemical compound); siRNA, anti-sense molecules, ribozymes, a biological agonist or antagonist of a cytokine or its receptor, or an aptamer. In one embodiment, the yeast used to produce the yeast-based immunotherapy composition has been engineered to carry or express the agent. Agents can include agonists and antagonists of a given protein or peptide or domain thereof. As used herein, an "agonist" is any compound or agent, including without limitation small molecules, proteins, peptides, antibodies, nucleic acid binding agents, etc., that binds to a receptor or ligand and produces or triggers a response, which may include agents that mimic the action of a naturally occurring substance that binds to the receptor or ligand. An "antagonist" is any compound or agent, including without limitation small molecules, proteins, peptides, antibodies, nucleic acid binding agents, etc., that blocks or inhibits or reduces the action of an agonist.

Proteins and peptides useful as agents according to the invention can include any protein or peptide that has the desired function, e.g., upregulation or downregulation of the production and/or survival of TH17, TH1 and/or Treg. For example, useful proteins or peptides can include, but are not limited to, cytokines and cytokine receptors, portions thereof, or agonists or antagonists thereof, antibodies or portions thereof, or blocking peptides. Proteins and peptides can include soluble inactive forms cytokines and/or their receptors.

Antibodies are characterized in that they comprise immunoglobulin domains and as such, they are members of the immunoglobulin superfamily of proteins. An antibody useful in the invention includes polyclonal and monoclonal antibodies, divalent and monovalent antibodies, bi- or multi-specific antibodies, serum containing such antibodies, antibodies that have been purified to varying degrees, and any functional equivalents of whole antibodies. Antibodies can include humanized antibodies, chimeric antibodies, and fully human antibodies, or functional portions or equivalents thereof. Isolated antibodies can include serum containing such antibodies, or antibodies that have been purified to varying degrees. Whole antibodies of the present invention can be polyclonal or monoclonal. Alternatively, functional equivalents of whole antibodies, such as antigen binding fragments (antigen binding portions) in which one or more antibody domains are truncated or absent (e.g., Fv, Fab, Fab', or $F(ab)_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention.

Genetically engineered antibodies of the invention include those produced by standard recombinant DNA techniques involving the manipulation and re-expression of DNA encoding antibody variable and/or constant regions. Particular examples include, chimeric antibodies, where the VH and/or VL domains of the antibody come from a different source to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Construction of chimeric and CDR-grafted antibodies are described, for example, in European Patent Applications: EP-A 0194276, EP-A 0239400, EP-A 0451216 and EP-A 0460617.

Humanized antibodies can be produced using a variety of methods known in the art, including but not limited to, use of recombinant DNA technology to create fully humanized or partially human (chimeric) antibodies (e.g., Norderhaug et al., 1997, J Immunol Methods 204 (1):77-87), which may include creation of a chimeric antibody (e.g., human-mouse) followed by selective mutagenesis to a more fully human sequence; insertion of human CDR regions into a human antibody scaffold (e.g., Kashmiri et al., 2005, Methods 36 (1): 25-34; or Hou et al., 2008, J Biochem 144 (1): 115-20); or phage display methods. Human antibodies may also be produced, for example, via the immunization of humans with a target protein or peptide or by collecting serum from patients having a particular disease or infection, and developing antibodies, including monoclonal antibodies from serum produced by the humans (e.g., Stacy et al., 2003, J Immunol Methods 283 (1-2): 247-59).

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (Nature 256:495-497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

The invention also extends to non-antibody polypeptides, sometimes referred to as binding partners, that have been designed to bind specifically to, and either activate or inhibit as appropriate, a given cytokine or receptor thereof, or other protein or molecule that can modulate TH17 cells. Examples of the design of such polypeptides, which possess prescribed ligand specificity are given in Beste et al. (Proc. Natl. Acad. Sci. 96:1898-1903, 1999), incorporated herein by reference in its entirety.

Antisense RNA and DNA molecules are based on nucleic acid sequences of the moiety to be inhibited, such as RNA or DNA encoding a cytokine Techniques for chemically synthesizing polynucleotides are well known in the art such as solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Antisense cDNA constructs that synthesize antisense RNA constitutively or inducibly, depending on the promoter used, can be introduced stably into host cells.

Aptamers are short strands of synthetic nucleic acids (usually RNA but also DNA) selected from randomized combinatorial nucleic acid libraries by virtue of their ability to bind to a predetermined specific target molecule with high affinity and specificity. Aptamers may also be peptides, which are designed to interfere with other protein interactions and consist of a variable peptide loop attached at both ends to a protein scaffold. Aptamers assume a defined three-dimensional structure and are capable of discriminating between compounds with very small differences in structure.

RNA interference (RNAi) is an approach for gene inactivation via gene silencing, termed "RNA interference" (RNAi). See, for example, Fire et al., Nature 391: 806-811 (1998) and U.S. Pat. No. 6,506,559. RNA interference refers to an event which occurs when an RNA polynucleotide acts through endogenous cellular processes to specifically suppress the expression of a gene whose sequence corresponds to that of the RNA. The silencing of the target gene occurs upon the degradation of mRNA by double strand (ds) RNA by the host animal, sometimes through RNAase III Endonuclease digestion. The digestion results in molecules that are about 21 to 23 nucleotides (or bases) in length (or size) although molecular size may be as large as 30 bases. These short RNA species (short interfering RNA or siRNA) mediate the degradation of corresponding RNA messages and transcripts, possibly via an RNAi nuclease complex, called the RNA-induced silencing complex (RISC), which helps the small dsRNAs recognize complementary mRNAs through base-pairing interactions. Following the siRNA interaction with its substrate, the mRNA is targeted for degradation, perhaps by enzymes that are present in the RISC. This type of mechanism appears to be useful to the organisms in inhibiting viral infections, transposon jumping, and similar phenomena, and to regulate the expression of endogenous genes. RNAi activity has been so far documented in plants, insects, nematodes and vertebrates among other organisms. For general background information, see, for example, Schutz et al., Virology 344(1): 151-7 (2006); Leonard et al., Gene Ther. 13(6):532-40 (2006); Colbere-Garapin et al., Microbes Infect. 7(4):767-75 (2005); Wall, Theriogenology 57(1):189-201 (2002); El-Bashir, et al., Nature 411: 494-498 (2001); Fire, A., et al. Science 391: 806-811 (1998); Gitlin et al., Nature 418: 430-434 (2002); Gitlin, et al., J. Virol. 79:1027-1035 (2005); Kahana, et al., J. Gen. Virol. 85, 3213-3217 (2004); Kronke et al., J. Virol. 78: 3436-3446 (2004); Leonard et al., J. Virol. 79:1645-1654 (2005); and Yokota, et al., EMBO Rep. 4: 602-608 (2003). By way of example, a yeast vehicle or yeast-based immunotherapeutic may be engineered to carry an siRNA that will inhibit the expression of a cytokine in an antigen presenting cell when such cell phagocytoses the yeast, thereby modulating an immune response associated with the activation of the antigen presenting cell by the yeast vehicle or yeast-based immunotherapeutic.

A ribozyme is an RNA segment that is able to perform biological catalysis (e.g., by breaking or forming covalent bonds). More specifically, ribozymes are antisense RNA molecules that function by binding to the target RNA moiety and inactivate it by cleaving the phosphodiester backbone at a specific cutting site. Such nucleic acid-based agents can be introduced into host cells or tissues and used to inhibit the expression and/or function of various proteins.

The invention also includes small molecule compounds (e.g., products of drug discovery and/or development) such as conformational antagonists or activators various receptors or mimics or modified forms cytokines or other molecules that are capable of interacting with biological proteins and receptors. Such an agent can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the same building blocks) or by rational drug design. See for example, Maulik et al., 1997, Molecular Biotechnology: Therapeutic Applications and Strategies, Wiley-Liss, Inc., which is incorporated herein by reference in its entirety.

The "expression" of a given protein (e.g., a cytokine or receptor) refers to transcription of a gene and/or translation of a protein encoded by the gene. The "activity" of a given protein refers generally to a biological activity, which is defined herein as any detectable activity that has an effect on the metabolic or other processes of a cell or organism, as measured or observed in vivo (i.e., in a natural physiological environment) or in vitro (i.e., under laboratory conditions).

Yeast-Based Immunotherapy Compositions

The present invention includes the use of at least one "yeast-based immunotherapeutic composition" (which phrase may be used interchangeably with "yeast-based immunotherapy product", "yeast-based composition", "yeast-based immunotherapeutic" or "yeast-based vaccine"). As used herein, the phrase "yeast-based immunotherapy composition" refers to a composition that includes a yeast vehicle component and that elicits an immune response sufficient to achieve at least one therapeutic benefit in a subject. More particularly, a yeast-based immunotherapeutic composition is a composition that includes a yeast vehicle component and can elicit or induce an immune response, such as a cellular immune response, including without limitation a T cell-mediated cellular immune response. In one aspect, an immunotherapy composition useful in the invention is capable of inducing a CD8+ and/or a CD4+ T cell-mediated immune response and in one aspect, a CD8+ and a CD4+ T cell-mediated immune response. Optionally, a yeast-based immunotherapy composition is capable of eliciting a humoral immune response. A yeast-based immunotherapy composition useful in the present invention can, for example, elicit an immune response in an individual such that the individual is treated for the disease or condition, or from symptoms resulting from the disease or condition.

Yeast-based immunotherapy compositions of the invention may be either "prophylactic" or "therapeutic". When provided prophylactically, the immunotherapy compositions of the present invention are provided in advance of any symptom of a disease or condition. The prophylactic administration of the immunotherapy compositions serves to prevent or ameliorate or delay time to onset of any subsequent disease. When provided therapeutically, the immunotherapy compositions are provided at or after the onset of a symptom of disease. The term, "disease" refers to any deviation from the normal health of an animal and includes a state when disease symptoms are present, as well as conditions in which a deviation (e.g., tumor growth, infection, etc.) has occurred, but symptoms are not yet manifested.

Typically, a yeast-based immunotherapy composition includes a yeast vehicle and at least one antigen or immunogenic domain thereof expressed by, attached to, or mixed with the yeast vehicle. In some embodiments, the antigen or immunogenic domain thereof is provided as a fusion protein. In one aspect of the invention, fusion protein can include two or more antigens. In one aspect, the fusion protein can include two or more immunogenic domains of one or more antigens, or two or more epitopes of one or more antigens. A TARMOGEN® is one non-limiting example of a yeast-based immunotherapy composition that is useful in the present invention. A TARMOGEN® (TARgeted MOlecular immunoGEN, GlobeImmune, Inc., Louisville, Colo.) generally refers to a yeast vehicle expressing one or more heterologous antigens extracellularly (on its surface), intracellularly (internally or cytosolically) or both extracellularly and intracellularly. Tarmogens have been generally described in the art. See, e.g., U.S. Pat. No. 5,830,463.

Yeast-based immunotherapy compositions, and methods of making and generally using the same, are described in detail, for example, in U.S. Pat. Nos. 5,830,463, 7,083,787, 7,465,454, U.S. Patent Publication 2007-0224208, U.S. Patent Publication No. US 2008-0003239, and in Stubbs et al., Nat. Med. 7:625-629 (2001), Lu et al., Cancer Research 64:5084-5088 (2004), and in Bernstein et al., Vaccine 2008 Jan. 24; 26(4):509-21, each of which is incorporated herein by reference in its entirety. These yeast-based immunotherapeutic products have been shown to elicit immune responses, including cellular and humoral immune responses. Yeast-based immunotherapeutic products are capable of killing target cells expressing a variety of antigens in vivo, in a variety of animal species, and to do so via antigen-specific, CD4+ and CD8+ mediated immune responses. Additional studies have shown that yeast are avidly phagocytosed by and directly activate dendritic cells which then present yeast-associated proteins to CD4+ and CD8+ T cells in a highly efficient manner. See, e.g., Stubbs et al. Nature Med. 5:625-629 (2001) and U.S. Pat. No. 7,083,787.

In any of the yeast-based immunotherapy compositions used in the present invention, the following aspects related to the yeast vehicle are included in the invention. According to the present invention, a yeast vehicle is any yeast cell (e.g., a whole or intact cell) or a derivative thereof (see below) that can be used in conjunction with one or more antigens, immunogenic domains thereof or epitopes thereof in a therapeutic composition of the invention, or in one aspect, the yeast vehicle can be used alone or as an adjuvant. In one aspect, the yeast are further used in conjunction with one or more agents useful for modulating TH17 and/or TH1 immune responses as described herein. The yeast vehicle can therefore include, but is not limited to, a live intact yeast microorganism (i.e., a yeast cell having all its components including a cell wall), a killed (dead) or inactivated intact yeast microorganism, or derivatives thereof including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation.

Yeast spheroplasts are typically produced by enzymatic digestion of the yeast cell wall. Such a method is described, for example, in Franzusoff et al., 1991, Meth. Enzymol. 194, 662-674, incorporated herein by reference in its entirety.

Yeast cytoplasts are typically produced by enucleation of yeast cells. Such a method is described, for example, in Coon, 1978, Natl. Cancer Inst. Monogr. 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, J. Biol.

Chem. 258, 3608-3614 and Bussey et al., 1979, Biochim. Biophys. Acta 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, Meth. Enzymol. 194, 662-674. One may also use fractions of yeast membrane particles that contain yeast membrane portions and, when the antigen or other protein was expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest (e.g., an agent for modulation of TH17 and/or TH1 immune responses as described herein) on the surface of the membrane or at least partially embedded within the membrane.

An example of a yeast cell wall preparation is isolated yeast cell walls carrying an antigen on its surface or at least partially embedded within the cell wall such that the yeast cell wall preparation, when administered to an animal, stimulates a desired immune response against a disease target. Alternatively or additionally, the yeast cell walls can carry an agent useful for the modulation of TH17 and/or TH1 immune responses as described herein.

Any yeast strain can be used to produce a yeast vehicle of the present invention. Yeast are unicellular microorganisms that belong to one of three classes: Ascomycetes, Basidiomycetes and Fungi Imperfecti. One consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain minimizes any adverse effects to the individual to whom the yeast vehicle is administered. However, pathogenic yeast may be used if the pathogenicity of the yeast can be negated by any means known to one of skill in the art (e.g., mutant strains). In accordance with one aspect of the present invention, non-pathogenic yeast strains are used.

Genera of yeast strains that may be used in the invention include but are not limited to *Saccharomyces, Candida* (which can be pathogenic), *Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in one aspect, *Saccharomyces* is used. Species of yeast strains that may be used in the invention include but are not limited to *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are intended to be included within the aforementioned species. In one aspect, yeast species used in the invention include *S. cerevisiae, C. albicans, H. polymorpha, P. pastoris* and *S. pombe. S. cerevisiae* is useful due to it being relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain. The *S. cerevisiae* strain is one such strain that is capable of supporting expression vectors that allow one or more target antigen(s) and/or antigen fusion protein(s) and/or other proteins to be expressed at high levels. In addition, any mutant yeast strains can be used in the present invention, including those that exhibit reduced post-translational modifications of expressed target antigens or other proteins, such as mutations in the enzymes that extend N-linked glycosylation.

In one embodiment, a yeast vehicle of the present invention is capable of fusing with the cell type to which the yeast vehicle and antigen/agent is being delivered, such as a dendritic cell or macrophage, thereby effecting particularly efficient delivery of the yeast vehicle, and in many embodiments, the antigen(s) or other agent, to the cell type. As used herein, fusion of a yeast vehicle with a targeted cell type refers to the ability of the yeast cell membrane, or particle thereof, to fuse with the membrane of the targeted cell type (e.g., dendritic cell or macrophage), leading to syncytia formation. As used herein, a syncytium is a multinucleate mass of protoplasm produced by the merging of cells. A number of viral surface proteins (including those of immunodeficiency viruses such as HIV, influenza virus, poliovirus and adenovirus) and other fusogens (such as those involved in fusions between eggs and sperm) have been shown to be able to effect fusion between two membranes (i.e., between viral and mammalian cell membranes or between mammalian cell membranes). For example, a yeast vehicle that produces an HIV gp120/gp41 heterologous antigen on its surface is capable of fusing with a CD4+ T-lymphocyte. It is noted, however, that incorporation of a targeting moiety into the yeast vehicle, while it may be desirable under some circumstances, is not necessary. In the case of yeast vehicles that express antigens extracellularly, this can be a further advantage of the yeast vehicles of the present invention. In general, yeast vehicles useful in the present invention are readily taken up by dendritic cells (as well as other cells, such as macrophages).

As discussed above, in some embodiments of the invention, a yeast vehicle and/or a yeast-based immunotherapy composition includes an agent that is useful for modulating a TH17 and/or a TH1 immune response, such agents having been described elsewhere herein. In most embodiments of the invention, the yeast-based immunotherapy composition includes at least one antigen, immunogenic domain thereof, or epitope thereof. The antigens contemplated for use in this invention include any antigen against which it is desired to elicit an immune response. In one aspect, yeast-based immunotherapeutic compositions, where the yeast carries (e.g., expresses, is loaded with, is connected to, etc.) or is admixed with an antigen or immunogenic domain thereof, may also carry or be admixed with an agent useful for modulation of TH17 and/or TH1 responses according to the invention. Alternatively, or in addition, yeast vehicles carrying an agent useful for modulation of TH17 and/or TH1 responses according to the invention can be mixed together with yeast-based immunotherapeutics, or administered concurrently with, sequentially with or in alternating manner with, yeast-based immunotherapeutics. Various combinations and permutations of yeast-based compositions can be constructed and used according to the present invention.

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to a microorganism or cells (whole microorganism, lysate or disrupted cells) or to a carbohydrate, or other molecule, or a portion thereof. An antigen may, in some embodiments, elicit an antigen-specific immune response (e.g., a humoral and/or a cell-mediated immune response) against the same or similar antigens that are encountered by an element of the immune system (e.g., T cells, antibodies). The term "cancer antigen" can be used interchangeably herein with the terms "tumor-specific antigen", "tumor-associated antigen", "cancer-associated target" or "tumor-associated target".

An antigen can be as small as a single epitope, or larger, and can include multiple epitopes. As such, the size of an antigen can be as small as about 5-12 amino acids (e.g., a small peptide) and as large as: a domain of a protein, a partial protein (peptide or polypeptide), a full length protein, including a multimer and fusion protein, chimeric protein, or agonist protein or peptide. In addition, antigens can include carbohydrates.

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual in the appropriate context (e.g., as part of a yeast-based immunotherapy composition) elicits or induces an antigen-specific immune response against the same or similar antigens that are encountered by the immune system of the individual.

An "immunogenic domain" of a given antigen can be any portion, fragment or epitope of an antigen (e.g., a peptide fragment or subunit or an antibody epitope or other conformational epitope) that contains at least one epitope that acts as an immunogen when administered to an animal. For example, a single protein can contain multiple different immunogenic domains. Immunogenic domains need not be linear sequences within a protein, such as in the case of a humoral immune response.

An epitope is defined herein as a single immunogenic site within a given antigen that is sufficient to elicit an immune response. Those of skill in the art will recognize that T cell epitopes are different in size and composition from B cell epitopes, and that epitopes presented through the Class I MHC pathway differ from epitopes presented through the Class II MHC pathway. Epitopes can be linear sequence or conformational epitopes (conserved binding regions).

The antigens contemplated for use in this invention include any antigen against which it is desired to elicit an immune response, and in particular, include any antigen for which a therapeutic immune response against such antigen would be beneficial to an individual. For example, the antigens can include, but are not limited to, any antigens associated with a pathogen, including viral antigens, fungal antigens, bacterial antigens, helminth antigens, parasitic antigens, ectoparasite antigens, protozoan antigens, or antigens from any other infectious agent. Antigens can also include any antigens associated with a particular disease or condition, whether from pathogenic or cellular sources, including, but not limited to, cancer antigens, antigens associated with an autoimmune disease (e.g., diabetes antigens), allergy antigens (allergens), mammalian cell molecules harboring one or more mutated amino acids, proteins normally expressed pre- or neo-natally by mammalian cells, proteins whose expression is induced by insertion of an epidemiologic agent (e.g. virus), proteins whose expression is induced by gene translocation, and proteins whose expression is induced by mutation of regulatory sequences. These antigens can be native antigens or genetically engineered antigens which have been modified in some manner (e.g., sequence change or generation of a fusion protein). It will be appreciated that in some embodiments (i.e., when the antigen is expressed by the yeast vehicle from a recombinant nucleic acid molecule), the antigen can be a protein or any epitope or immunogenic domain thereof, a fusion protein, or a chimeric protein, rather than an entire cell or microorganism.

Other antigens that are useful in yeast-based immunotherapy compositions of the present invention include antigens that may be relevant to suppressing an undesired, or harmful, immune response, such as is caused, for example, by allergens, autoimmune antigens, inflammatory agents, antigens involved in GVHD, certain cancers, septic shock antigens, and antigens involved in transplantation rejection.

In one aspect of the invention, antigens useful in one or more immunotherapy compositions of the invention include any cancer or tumor-associated antigen. In one aspect, the antigen includes an antigen associated with a preneoplastic or hyperplastic state. The antigen may also be associated with, or causative of cancer. Such an antigen may be tumor-specific antigen, tumor-associated antigen (TAA) or tissue-specific antigen, epitope thereof, and epitope agonist thereof. Cancer antigens include, but are not limited to, antigens from any tumor or cancer, including, but not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, leukemias, lymphomas, primary hepatic cancers, lung cancers, pancreatic cancers, gastrointestinal cancers (including colorectal cancers), renal cell carcinomas, hematopoietic neoplasias and metastatic cancers thereof.

Suitable cancer antigens include but are not limited to carcinoembryonic antigen (CEA) and epitopes thereof such as CAP-1, CAP-1-6D (GenBank Accession No. M29540), MART-1 (Kawakami et al, J. Exp. Med. 180:347-352, 1994), MAGE-1 (U.S. Pat. No. 5,750,395), MAGE-3, GAGE (U.S. Pat. No. 5,648,226), GP-100 (Kawakami et al Proc. Nat'l Acad. Sci. USA 91:6458-6462, 1992), MUC-1, MUC-2, point mutated Ras oncoprotein, normal and point mutated p53 oncoproteins (Hollstein et al Nucleic Acids Res. 22:3551-3555, 1994), PSMA (Israeli et al Cancer Res. 53:227-230, 1993), tyrosinase (Kwon et al PNAS 84:7473-7477, 1987), TRP-1 (gp75) (Cohen et al Nucleic Acid Res. 18:2807-2808, 1990; U.S. Pat. No. 5,840,839), NY-ESO-1 (Chen et al PAS 94: 1914-1918, 1997), TRP-2 (Jackson et al EMBO J, 11:527-535, 1992), TAG72, KSA, CA-125, PSA, HER-2/neu/c-erb/B2, (U.S. Pat. No. 5,550,214), EGFR, hTERT, p73, B-RAF, adenomatous polyposis coli (APC), Myc, von Hippel-Lindau protein (VHL), Rb-1, Rb-2, androgen receptor (AR), Smad4, MDR1, Flt-3, BRCA-1, BRCA-2, Bcr-Abl, pax3-fkhr, ews-fli-1, Brachyury, HERV-H, HERV-K, TWIST, Mesothelin, NGEP, modifications of such antigens and tissue specific antigens, splice variants of such antigens, and/or epitope agonists of such antigens. Other cancer antigens are known in the art. Other cancer antigens may also be identified, isolated and cloned by methods known in the art such as those disclosed in U.S. Pat. No. 4,514,506. Cancer antigens may also include one or more growth factors and splice variants of each.

In one aspect of the invention, antigens useful in one or more immunotherapy compositions of the invention include any antigens associated with a pathogen or a disease or condition caused by or associated with a pathogen. Such antigens include, but are not limited to, any antigens associated with a pathogen, including viral antigens, fungal antigens, bacterial antigens, helminth antigens, parasitic antigens, ectoparasite antigens, protozoan antigens, or antigens from any other infectious agent.

In one aspect, the antigen is from virus, including, but not limited to, adenoviruses, arena viruses, bunyaviruses, coronaviruses, coxsackie viruses, cytomegaloviruses, Epstein-Barr viruses, flaviviruses, hepadnaviruses, hepatitis viruses, herpes viruses, influenza viruses, lentiviruses, measles viruses, mumps viruses, myxoviruses, orthomyxoviruses, papilloma viruses, papovaviruses, parainfluenza viruses, paramyxoviruses, parvoviruses, picornaviruses, pox viruses, rabies viruses, respiratory syncytial viruses, reoviruses, rhabdoviruses, rubella viruses, togaviruses, and varicella viruses. Other viruses include T-lymphotrophic viruses, such as human T-cell lymphotrophic viruses (HTLVs, such as HTLV-I and HTLV-II), bovine leukemia viruses (BLVS) and feline leukemia viruses (FLVs). The lentiviruses include, but are not limited to, human (HIV, including HIV-1 or HIV-2), simian (SIV), feline (FIV) and canine (CIV) immunodeficiency viruses. In one embodiment, viral antigens include those from non-oncogenic viruses.

In another aspect, the antigen is from an infectious agent from a genus selected from: *Aspergillus, Bordetella, Brugia, Candida, Chlamydia, Coccidia, Cryptococcus, Dirofilaria, Escherichia, Francisella, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma, Vibriocholerae*, and *Yersinia*. In one aspect, the infectious agent is selected from *Plasmodium falciparum* or *Plasmodium vivax.*

In one aspect, the antigen is from a bacterium from a family selected from: Enterobacteriaceae, Micrococcaceae, Vibrionaceae, Pasteurellaceae, Mycoplasmataceae, and Rickettsiaceae. In one aspect, the bacterium is of a genus selected from: *Pseudomonas, Bordetella, Mycobacterium, Vibrio, Bacillus, Salmonella, Francisella, Staphylococcus, Streptococcus, Escherichia, Enterococcus, Pasteurella*, and *Yersinia*. In one aspect, the bacterium is from a species selected from: *Pseudomonas aeruginosa, Pseudomonas mallei, Pseudomonas pseudomallei, Bordetella pertussis, Mycobacterium tuberculosis, Mycobacterium leprae, Francisella tularensis, Vibrio cholerae, Bacillus anthracis, Salmonella enteric, Yersinia pestis, Escherichia coli* and *Bordetella bronchiseptica.*

In one aspect, the antigen is from a fungus, such a fungus including, but not limited to, a fungus from *Saccharomyces* spp., *Aspergillus* spp., *Cryptococcus* spp., *Coccidioides* spp., *Neurospora* spp., *Histoplasma* spp., or *Blastomyces* spp. In one aspect, the fungus is from a species selected from: *Aspergillus fumigatus, A. flavus, A. niger, A. terreus, A. nidulans, Coccidioides immitis, Coccidioides posadasii* or *Cryptococcus neoformans*. The most common species of *Aspergillus* causing invasive disease include *A. fumigatus, A. flavus, A. niger, A. terreus* and *A. nidulans*, and may be found, for example, in patients who have immunosuppression or T-cell or phagocytic impairment. *A. fumigatus* has been implicated in asthma, aspergillomas and invasive aspergillosis. Coccidioidomycosis, also known as San Joaquin Valley Fever, is a fungal disease caused by *Coccidioides immitis*, and can lead to acute respiratory infections and chronic pulmonary conditions or dissemination to the meninges, bones, and joints. Cryptococcosis-associated conditions are also targeted by methods of the invention, for example, in a non-immunosuppressed or immunosuppressed subject, such as a subject who is infected with HIV.

In some embodiments, the antigen is a fusion protein. In one aspect of the invention, fusion protein can include two or more antigens. In one aspect, the fusion protein can include two or more immunogenic domains or two or more epitopes of one or more antigens. An immunotherapeutic composition containing such antigens may provide antigen-specific immunization in a broad range of patients. For example, a multiple domain fusion protein useful in the present invention may have multiple domains, wherein each domain consists of a peptide from a particular protein, the peptide consisting of at least 4 amino acid residues flanking either side of and including a mutated amino acid that is found in the protein, wherein the mutation is associated with a particular disease or condition.

In one embodiment, fusion proteins that are used as a component of the yeast-based immunotherapeutic composition useful in the invention are produced using constructs that are particularly useful for the expression of heterologous antigens in yeast. Typically, the desired antigenic protein(s) or peptide(s) are fused at their amino-terminal end to: (a) a specific synthetic peptide that stabilizes the expression of the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, wherein either fusion partner provides significantly enhanced stability of expression of the protein in the yeast and/or a prevents post-translational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein, described in more detail herein). In addition, the present invention includes the use of peptides that are fused to the C-terminus of the antigen-encoding construct, particularly for use in the selection and identification of the protein. Such peptides include, but are not limited to, any synthetic or natural peptide, such as a peptide tag (e.g., 6×His) or any other short epitope tag. Peptides attached to the C-terminus of an antigen according to the invention can be used with or without the addition of the N-terminal peptides discussed above.

In one embodiment, a synthetic peptide useful in a fusion protein is linked to the N-terminus of the antigen, the peptide consisting of at least two amino acid residues that are heterologous to the antigen, wherein the peptide stabilizes the expression of the fusion protein in the yeast vehicle or prevents posttranslational modification of the expressed fusion protein. The synthetic peptide and N-terminal portion of the antigen together form a fusion protein that has the following requirements: (1) the amino acid residue at position one of the fusion protein is a methionine (i.e., the first amino acid in the synthetic peptide is a methionine); (2) the amino acid residue at position two of the fusion protein is not a glycine or a proline (i.e., the second amino acid in the synthetic peptide is not a glycine or a proline); (3) none of the amino acid residues at positions 2-6 of the fusion protein is a methionine (i.e., the amino acids at positions 2-6, whether part of the synthetic peptide or the protein, if the synthetic peptide is shorter than 6 amino acids, do not include a methionine); and (4) none of the amino acids at positions 2-6 of the fusion protein is a lysine or an arginine (i.e., the amino acids at positions 2-6, whether part of the synthetic peptide or the protein, if the synthetic peptide is shorter than 5 amino acids, do not include a lysine or an arginine). The synthetic peptide can be as short as two amino acids, but in one aspect, is at least 2-6 amino acids (including 3, 4, 5 amino acids), and can be longer than 6 amino acids, in whole integers, up to about 200 amino acids, 300 amino acids, 400 amino acids, 500 amino acids, or more.

In one embodiment, a fusion protein comprises an amino acid sequence of M-X2-X3-X4-X5-X6, wherein M is methionine; wherein X2 is any amino acid except glycine, proline, lysine or arginine; wherein X3 is any amino acid except methionine, lysine or arginine; wherein X4 is any amino acid except methionine, lysine or arginine; wherein X5 is any amino acid except methionine, lysine or arginine; and wherein X6 is any amino acid except methionine, lysine or arginine. In one embodiment, the X6 residue is a proline. An exemplary synthetic sequence that enhances the stability of expression of an antigen in a yeast cell and/or prevents post-translational modification of the protein in the yeast includes the sequence M-A-D-E-A-P (SEQ ID NO:1). In addition to the enhanced stability of the expression product, this fusion partner does not appear to negatively impact the immune response against the vaccinating antigen in the construct. In addition, the synthetic fusion peptides can be designed to provide an epitope that can be recognized by a selection agent, such as an antibody.

In one aspect of the invention, the yeast vehicle is manipulated such that the antigen, or an agent useful for modulating TH17 and/or TH1 immune responses, is expressed or provided by delivery or translocation of an expressed protein product, partially or wholly, on the surface of the yeast vehicle (extracellular expression). One method for accomplishing this aspect of the invention is to use a spacer arm for positioning one or more protein(s) on the surface of the yeast vehicle. For example, one can use a spacer arm to create a fusion protein of the antigen(s) or other protein of interest with a protein that targets the antigen(s) or other protein of interest to the yeast cell wall. For example, one such protein that can be used to target other proteins is a yeast protein (e.g., cell wall protein 2 (cwp2), Aga2, Pir4 or Flo1 protein) that enables the antigen(s) or other protein to be targeted to the yeast cell wall such that the antigen or other protein is located on the surface of the yeast. Proteins other than yeast proteins may be used for the spacer arm; however, for any spacer arm protein, it is most desirable to have the immunogenic response be directed against the target antigen rather than the spacer arm protein. As such, if other proteins are used for the spacer arm, then the spacer arm protein that is used should not generate such a large immune response to the spacer arm protein itself such that the immune response to the target antigen(s) is overwhelmed. One of skill in the art should aim for a small immune response to the spacer arm protein relative to the immune response for the target antigen(s). Spacer arms can be constructed to have cleavage sites (e.g., protease cleavage sites) that allow the antigen to be readily removed or processed away from the yeast, if desired. Any known method of determining the magnitude of immune responses can be used (e.g., antibody production, lytic assays, etc.) and are readily known to one of skill in the art.

Another method for positioning the target antigen(s) or other proteins to be exposed on the yeast surface is to use signal sequences such as glycosylphosphatidyl inositol (GPI) to anchor the target to the yeast cell wall. Alternatively, positioning can be accomplished by appending signal sequences that target the antigen(s) or other proteins of interest into the secretory pathway via translocation into the endoplasmic reticulum (ER) such that the antigen binds to a protein which is bound to the cell wall (e.g., cwp).

In one aspect, the spacer arm protein is a yeast protein. The yeast protein can consist of between about two and about 800 amino acids of a yeast protein. In one embodiment, the yeast protein is about 10 to 700 amino acids. In another embodiment, the yeast protein is about 40 to 600 amino acids. Other embodiments of the invention include the yeast protein being at least 250 amino acids, at least 300 amino acids, at least 350 amino acids, at least 400 amino acids, at least 450 amino acids, at least 500 amino acids, at least 550 amino acids, at least 600 amino acids, or at least 650 amino acids. In one embodiment, the yeast protein is at least 450 amino acids in length.

Use of yeast proteins can stabilize the expression of fusion proteins in the yeast vehicle, prevents posttranslational modification of the expressed fusion protein, and/or targets the fusion protein to a particular compartment in the yeast (e.g., to be expressed on the yeast cell surface). For delivery into the yeast secretory pathway, exemplary yeast proteins to use include, but are not limited to: Aga (including, but not limited to, Aga1 and/or Aga2); SUC2 (yeast invertase); alpha factor signal leader sequence; CPY; Cwp2p for its localization and retention in the cell wall; BUD genes for localization at the yeast cell bud during the initial phase of daughter cell formation; Flo1p; Pir2p; and Pir4p.

Other sequences can be used to target, retain and/or stabilize the protein to other parts of the yeast vehicle, for example, in the cytosol or the mitochondria. Examples of suitable yeast protein that can be used for any of the embodiments above include, but are not limited to, SEC7; phosphoenolpyruvate carboxykinase PCK1, phosphoglycerokinase PGK and triose phosphate isomerase TPI gene products for their repressible expression in glucose and cytosolic localization; the heat shock proteins SSA1, SSA3, SSA4, SSC1, whose expression is induced and whose proteins are more thermostable upon exposure of cells to heat treatment; the mitochondrial protein CYC1 for import into mitochondria; ACT1.

Methods of producing yeast vehicles and expressing, combining and/or associating yeast vehicles with antigens and/or other proteins and/or agents of interest to produce yeast-based immunotherapy compositions are contemplated by the invention.

According to the present invention, the term "yeast vehicle-antigen complex" or "yeast-antigen complex" is used generically to describe any association of a yeast vehicle with an antigen, and can be used interchangeably with "yeast-based immunotherapy composition" when such composition is used to elicit an immune response as described above. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell used to prepare the yeast vehicle is transfected with a heterologous nucleic acid molecule encoding a protein (e.g., the antigen or agent) such that the protein is expressed by the yeast cell. Such a yeast is also referred to herein as a recombinant yeast or a recombinant yeast vehicle. The yeast cell can then be loaded into the dendritic cell as an intact cell, or the yeast cell can be killed, or it can be derivatized such as by formation of yeast spheroplasts, cytoplasts, ghosts, or subcellular particles, any of which is followed by loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen or other protein.

In one aspect, a yeast cell or yeast spheroplast used to prepare the yeast vehicle is transfected with a recombinant nucleic acid molecule encoding the antigen(s) or other protein such that the antigen or other protein is recombinantly expressed by the yeast cell or yeast spheroplast. In this aspect, the yeast cell or yeast spheroplast that recombinantly expresses the antigen(s) or other protein is used to produce a yeast vehicle comprising a yeast cytoplast, a yeast ghost, or a yeast membrane particle or yeast cell wall particle, or fraction thereof.

In general, the yeast vehicle and antigen(s) or other agent, including agents that modulate a TH17 and/or TH1 response according to the invention, can be associated by any technique described herein. In one aspect, the yeast vehicle was loaded intracellularly with the antigen(s) and/or agent(s). In another aspect, the antigen(s) and/or agent(s) was covalently or non-covalently attached to the yeast vehicle. In yet another aspect, the yeast vehicle and the antigen(s) and/or agent(s) were associated by mixing. In another aspect, and in one embodiment, the antigen(s) and/or agent(s) is expressed recombinantly by the yeast vehicle or by the yeast cell or yeast spheroplast from which the yeast vehicle was derived.

A number of antigens and/or other proteins to be produced by a yeast vehicle of the present invention is any number of antigens and/or other proteins that can be reasonably produced by a yeast vehicle, and typically ranges from at least one to at least about 6 or more, including from about 2 to about 6 heterologous antigens and or other proteins.

Expression of an antigen or other protein in a yeast vehicle of the present invention is accomplished using techniques known to those skilled in the art. Briefly, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art. Promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome c1 (CYC1), Sec7 protein (SEC7) and acid phosphatase (PHOS), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the α-factor, GAPDH, and CYC1 genes.

Transcription control sequences to express genes in methyltrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule administered into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins.

Effective conditions for the production of recombinant yeast vehicles and expression of the antigen and/or other protein (e.g., an agent as described herein) by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, Methods in Enzymology, vol. 194, Academic Press, San Diego).

In some aspects of the invention, the yeast are grown under neutral pH conditions, and particularly, in a media maintained at a pH level of at least 5.5, namely the pH of the culture media is not allowed to drop below pH 5.5. In other aspects, the yeast is grown at a pH level maintained at about 5.5. In other aspects, the yeast is grown at a pH level maintained at about 5.6, 5.7, 5.8 or 5.9. In another aspect, the yeast is grown at a pH level maintained at about 6. In another aspect, the yeast is grown at a pH level maintained at about 6.5. In other aspects, the yeast is grown at a pH level maintained at about 6, 6.1, 6.2, 6.3, 6.4, 6.5, 6.6, 6.7, 6.8, 6.9 or 7.0. In other aspects, the yeast is grown at a pH level maintained at about 7, 7.1, 7.2, 7.3, 7.4, 7.5, 7.6, 7.7, 7.8, 7.9, or 8.0. The pH level is important in the culturing of yeast. One of skill in the art will appreciate that the culturing process includes not only the start of the yeast culture but the maintenance of the culture as well. As yeast culturing is known to turn acidic (i.e., lowering the pH) over time, care must be taken to monitor the pH level during the culturing process. Yeast cell cultures whereby the pH level of the medium drops below 6 are still contemplated within the scope of the invention provided that the pH of the media is brought up to at least 5.5 at some point during the culturing process. As such, the longer time the yeast are grown in a medium that is at least pH 5.5 or above, the better the results will be in terms of obtaining yeast with desirable characteristics.

As used herein, the general use of the term "neutral pH" refers to a pH range between about pH 5.5 and about pH 8, and in one aspect, between about pH 6 and about 8. One of skill the art will appreciate that minor fluctuations (e.g., tenths or hundredths) can occur when measuring with a pH meter. As such, the use of neutral pH to grow yeast cells means that the yeast cells are grown in neutral pH for the majority of the time that they are in culture. The use of a neutral pH in culturing yeast promotes several biological effects that are desirable characteristics for using the yeast as vehicles for immunomodulation. In one aspect, culturing the yeast in neutral pH allows for good growth of the yeast without any negative effect on the cell generation time (e.g., slowing down the doubling time). The yeast can continue to grow to high densities without losing their cell wall pliability. In another aspect, the use of a neutral pH allows for the production of yeast with pliable cell walls and/or yeast that are sensitive to cell wall digesting enzymes (e.g., glucanase) at all harvest densities. This trait is desirable because yeast with flexible cell walls can induce unusual immune responses, such as by promoting the secretion of cytokines (e.g., interferon-γ (IFN-γ)) in the cells hosting the yeast. In addition, greater accessibility to the antigens located in the cell wall is afforded by such culture methods. In another aspect, the use of neutral pH for some antigens allows for release of the di-sulfide bonded antigen by treatment with dithiothreitol (DTT) that is not possible when such an antigen-expressing yeast is cultured in media at lower pH (e.g., pH 5). Finally, in another aspect, yeast cultured using the neutral pH methodologies, elicit increased production of at least TH1-type cytokines including, but not limited to, IFN-γ, interleukin-12 (IL-12), and IL-2, and may also elicit increased production of other cytokines, such as proinflammatory cytokines (e.g., IL-6).

In one embodiment, control of the amount of yeast glycosylation is used to control the expression of antigens by the yeast, particularly on the surface. The amount of yeast glycosylation can affect the immunogenicity and antigenicity of the antigen expressed on the surface, since sugar moieties tend to be bulky. As such, the existence of sugar moieties on the surface of yeast and its impact on the three-dimensional space around the target antigen(s) should be considered in the modulation of yeast according to the invention. Any method can be used to reduce the amount of glycosylation of the yeast (or increase it, if desired). For example, one could use a yeast mutant strain that has been selected to have low glycosylation (e.g. mnn1, och1 and mnn9 mutants), or one could eliminate by mutation the glycosylation acceptor sequences on the target antigen. Alternatively, one could use a yeast with abbreviated glycosylation patterns, e.g. *Pichia*. One can also treat the yeast using methods that reduce or alter the glycosylation.

In one embodiment of the present invention, as an alternative to expression of an antigen or other protein recombinantly in the yeast vehicle, a yeast vehicle is loaded intracellularly with the protein or peptide, or with carbohydrates or other molecules that serve as an antigen and/or are useful as immunomodulatory agents or biological response modifiers according to the invention. Subsequently, the yeast vehicle, which now contains the antigen and/or other proteins intracellularly, can be administered to the patient or loaded into a carrier such as a dendritic cell. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens and other agents after production. Alternatively, intact yeast can be loaded with the antigen and/or agent, and then spheroplasts, ghosts, cytoplasts, or subcellular particles can be prepared therefrom. Any number of antigens and/or other agents can be loaded into a yeast vehicle in this embodiment, from at least 1, 2, 3, 4 or any whole integer up to hundreds or thousands of antigens and/or other agents, such as would be provided by the loading of a microorganism, by the loading of a mammalian tumor cell, or portions thereof, for example.

In another embodiment of the present invention, an antigen and/or other agent is physically attached to the yeast vehicle. Physical attachment of the antigen and/or other agent to the yeast vehicle can be accomplished by any method suitable in the art, including covalent and non-covalent association methods which include, but are not limited to, chemically crosslinking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

When the antigen or other protein is expressed on or physically attached to the surface of the yeast, spacer arms may, in one aspect, be carefully selected to optimize antigen or other protein expression or content on the surface. The size of the spacer arm(s) can affect how much of the antigen or other protein is exposed for binding on the surface of the yeast. Thus, depending on which antigen(s) or other protein(s) are being used, one of skill in the art will select a spacer arm that effectuates appropriate spacing for the antigen or other protein on the yeast surface. In one embodiment, the spacer arm is a yeast protein of at least 450 amino acids. Spacer arms have been discussed in detail above.

Another consideration for optimizing antigen surface expression is whether the antigen and spacer arm combination should be expressed as a monomer or as dimer or as a trimer, or even more units connected together. This use of monomers, dimers, trimers, etc. allows for appropriate spacing or folding of the antigen such that some part, if not all, of the antigen is displayed on the surface of the yeast vehicle in a manner that makes it more immunogenic.

In yet another embodiment, the yeast vehicle and the antigen or other protein are associated with each other by a more passive, non-specific or non-covalent binding mechanism, such as by gently mixing the yeast vehicle and the antigen or other protein together in a buffer or other suitable formulation (e.g., admixture).

In one embodiment of the invention, the yeast vehicle and the antigen or other protein are both loaded intracellularly into a carrier such as a dendritic cell or macrophage to form the therapeutic composition or vaccine of the present invention. Alternatively, an antigen or other protein can be loaded into a dendritic cell in the absence of the yeast vehicle.

In one embodiment, intact yeast (with or without expression of heterologous antigens or other proteins) can be ground up or processed in a manner to produce yeast cell wall preparations, yeast membrane particles or yeast fragments (i.e., not intact) and the yeast fragments can, in some embodiments, be provided with or administered with other compositions that include antigens (e.g., DNA vaccines, protein subunit vaccines, killed or inactivated pathogens) to enhance immune response. For example, enzymatic treatment, chemical treatment or physical force (e.g., mechanical shearing or sonication) can be used to break up the yeast into parts that are used as an adjuvant.

In one embodiment of the invention, yeast vehicles useful in the invention include yeast vehicles that have been killed or inactivated. Killing or inactivating of yeast can be accomplished by any of a variety of suitable methods known in the art. For example, heat inactivation of yeast is a standard way of inactivating yeast, and one of skill in the art can monitor the structural changes of the target antigen, if desired, by standard methods known in the art. Alternatively, other methods of inactivating the yeast can be used, such as chemical, electrical, radioactive or UV methods. See, for example, the methodology disclosed in standard yeast culturing textbooks such as Methods of Enzymology, Vol. 194, Cold Spring Harbor Publishing (1990). Any of the inactivation strategies used should take the secondary, tertiary or quaternary structure of the target antigen into consideration and preserve such structure as to optimize its immunogenicity.

Yeast vehicles can be formulated into yeast-based immunotherapy compositions or products of the present invention, including preparations to be administered to a subject directly or first loaded into a carrier such as a dendritic cell, using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

In one embodiment of the present invention, a composition can include biological response modifier compounds, or the ability to produce such modifiers (i.e., by transfection of the yeast vehicle with nucleic acid molecules encoding such modifiers), and in one aspect, such biological response modifiers may be the same as an agent useful in the present invention for modulating TH17, TH1, and/or Treg immune responses. Biological response modifiers have been described above.

Compositions of the invention can further include any other compounds that are useful for protecting a subject from a particular disease or condition, including an infectious disease or cancer, or any compounds that treat or ameliorate any symptom of such an infection.

Accordingly, the invention also includes a variety of compositions that are useful in the methods of the invention, various aspects of which have been described in detail above. In one embodiment, a composition includes: (a) a yeast-based immunotherapy composition; and (b) an agent that downregulates the production and/or survival of TH17 cells. In another embodiment, a composition includes: (a) a yeast-based immunotherapy composition; and (b) an agent that downregulates the expression or activity of a cytokine selected from the group consisting of: interleukin-1 (IL-1), IL-6, IL-17, IL-21, IL-22 and/or IL-23, or a receptor thereof. In another embodiment, a composition includes (a) a yeast-based immunotherapy composition; and (b) interleukin-25 (IL-25) or interleukin-27 (IL-27) or an agonist thereof. In another embodiment, a composition includes (a) a yeast-based immunotherapy composition; and (b) an agent that upregulates the production and/or survival of TH17 cells. In another embodiment, a composition includes (a) a yeast-based immunotherapy composition; and (b) a cytokine selected from the group consisting of: interleukin-1 (IL-1), IL-6, IL-17, IL-21, IL-22 and/or IL-23, or an agonist thereof. In yet another embodiment, a composition includes (a) a yeast-based immunotherapy composition; and (b) an agent that downregulates the expression or activity of interleukin-25 (IL-25), interleukin-27 (IL-27) or a receptor thereof.

In another embodiment, a composition comprising a yeast-based immunotherapy composition, including any composition described above, can include an agent that upregulates the production and/or survival of TH1. In another embodiment, a composition comprising a yeast-based immunotherapy composition, including any composition described above, can include an agent that downregulates the production and/or survival of TH1.

In another embodiment, a composition comprising a yeast-based immunotherapy composition, including any composition described above, can include an agent that downregulates the production and/or survival of Tregs.

Other embodiments of the invention include a composition comprising (a) a yeast-based immunotherapy composition; and (b) any combination of agents useful for modulating a TH17 response, a TH1 response, and/or Treg responses in a manner consistent with the methods of the invention.

The invention also includes a kit comprising any of the compositions described herein, or any of the individual components of the compositions described herein. In one embodiment, a kit of the invention includes a yeast-based immunotherapy composition and one or more reagents for detecting TH17 cells, TH1 cells and/or Treg. Such reagents can include, but are not limited to, reagents for detecting T cell proliferation, cytokine expression or production, and/or expression of transcription factors or receptors associated with TH17 cells, TH1 and/or Treg. Reagents may be present in free form or immobilized to a substrate such as a plastic dish, microarray plate, a test tube, a test rod and so on. The kit can also include suitable reagents for the detection of the reagent and/or for the labeling of positive or negative controls, wash solutions, dilution buffers and the like. The kit can also include a set of written instructions for using the kit and interpreting the results. In one embodiment, the kit is formulated to be a high-throughput assay. Kits may be prepared and used for any clinical, research or diagnostic method of the invention.

Methods for Administration or Use of Compositions of the Invention

The present invention includes the delivery (administration, immunization) of a composition of the invention to a subject. The administration process can be performed ex vivo or in vivo, but is typically performed in vivo. Ex vivo administration refers to performing part of the regulatory step outside of the patient, such as administering a composition of the present invention to a population of cells (dendritic cells) removed from a patient under conditions such that a yeast vehicle, antigen(s) and any other agents or compositions are loaded into the cell, and returning the cells to the patient. The therapeutic composition of the present invention can be returned to a patient, or administered to a patient, by any suitable mode of administration.

Administration of a composition can be systemic, mucosal and/or proximal to the location of the target site (e.g., near a tumor). Suitable routes of administration will be apparent to those of skill in the art, depending on the type of condition to be prevented or treated, the antigen used, and/or the target cell population or tissue. Various acceptable methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., Proc. Natl. Acad. Sci. USA 189:11277-11281, 1992, which is incorporated herein by reference in its entirety). Other routes of administration that modulate mucosal immunity are useful in the treatment of viral infections. Such routes include bronchial, intradermal, intramuscular, intranasal, other inhalatory, rectal, subcutaneous, topical, transdermal, vaginal and urethral routes. In one aspect, an immunotherapeutic composition of the invention is administered subcutaneously.

With respect to the yeast-based immunotherapy compositions of the invention, in general, a suitable single dose is a dose that is capable of effectively providing a yeast vehicle and an antigen (if included) to a given cell type, tissue, or region of the patient body in an amount effective to elicit an antigen-specific immune response, when administered one or more times over a suitable time period. For example, in one embodiment, a single dose of a yeast vehicle of the present invention is from about $1\times10^5$ to about $5\times10^7$ yeast cell equivalents per kilogram body weight of the organism being administered the composition. In one aspect, a single dose of a yeast vehicle of the present invention is from about 0.1 Y.U. ($1\times10^6$ cells) to about 100 Y.U. ($1\times10^9$ cells) per dose (i.e., per organism), including any interim dose, in increments of $0.1\times10^6$ cells (i.e., $1.1\times10^6$, $1.2\times10^6$, $1.3\times10^6$ . . . ). In one embodiment, doses include doses between 1 Y.U and 40 Y.U. and in one aspect, between 10 Y.U. and 40 Y.U. In one embodiment, the doses are administered at different sites on the individual but during the same dosing period. For example, a 40 Y.U. dose may be administered via by injecting 10 Y.U. doses to four different sites on the individual during one dosing period.

"Boosters" or "boosts" of a therapeutic composition are administered, for example, when the immune response against the antigen has waned or as needed to provide an immune response or induce a memory response against a particular antigen or antigen(s). Boosters can be administered from about 1, 2, 3, 4, 5, 6, 7, or 8 weeks apart, to monthly, to bimonthly, to quarterly, to annually, to several years after the original administration. In one embodiment, an administration schedule is one in which from about $1\times10^5$ to about $5\times10^7$ yeast cell equivalents of a composition per kg body weight of the organism is administered at least 1, 2, 3, 4, 5, 6, 7, 8, 9, 10, or more times over a time period of from weeks, to months, to years.

Agents that regulate TH17 cells, TH1 cells, and/or Treg for administration in the present invention can be administered at a dosage and by a protocol that is readily known or determined by those of skill in the art for the particular agent type to be administered. With respect to agents useful in the invention, a protein or antibody is administered, in one aspect, in an amount that is between about 50 U/kg and about 15,000 U/kg body weight of the subject. In another embodiment, a protein or antibody is administered in an amount that is between about 0.01 μg and about 10 mg per kg body weight of the patient, and more preferably, between about 0.1 μg and about 100 μg per kg body weight of the patient. When the compound to be delivered is a nucleic acid molecule, an appropriate single dose results in at least about 1 pg of protein expressed per mg of total tissue protein per μg of nucleic acid delivered. Small molecules are delivered according to the preferred dosage specified for the given small molecule and can be determined by those of skill in the art.

In one aspect of the invention, the agent is administered concurrently with the yeast-based immunotherapy composition. In one aspect of the invention, the agent is administered sequentially with the yeast-based immunotherapy composition. In another embodiment, the agent is administered before the yeast-based immunotherapy composition is administered. In another embodiment, the agent is administered after the yeast-based immunotherapy composition is administered. In one embodiment, the agent is administered in alternating doses with the yeast-based immunotherapy composition, or in a protocol in which the yeast-based composition is administered at prescribed intervals in between or with one or more consecutive doses of the agent, or vice versa. In one embodiment, the yeast-based immunotherapy composition is administered in one or more doses over a period of time prior to commencing the administration of the agent. In other words, the yeast-based immunotherapeutic composition is administered as a monotherapy for a period of time, and then the agent administration is added, either concurrently with new doses of yeast-based immunotherapy, or in an alternating fashion with yeast-based immunotherapy. Alternatively, the agent may be administered for a period of time prior to beginning administration of the yeast-based immunotherapy composition. In one aspect, the yeast is engineered to express or carry the agent, or a different yeast is engineered or produced to express or carry the agent.

As used herein with respect to administration of a composition, the term "concurrently" means to administer each of the compositions (e.g., the yeast-based immunotherapeutic composition and the agent that modulates TH17 cells), and particularly, the first dose of such compositions, essentially at the same time or within the same dosing period, or within a time period during which the initial effects of priming of the immune system by the immunotherapy composition occurs (e.g., within 1-2 days or less). For clarity, concurrent administration does not require administration of all of the compositions at precisely the same moment, but rather, the administration of all compositions should occur within one scheduled dosing of the patient in order to prime the immune system and achieve the effect of the agent concurrently (e.g., one composition may be administered first, followed immediately or closely by the administration of the second composition, and so on). In some circumstances, such as when the compositions are administered to the same site, the compositions may be provided in admixture, although even when administered at the same site, sequential administration of each composition during the same dosing period may be used. In one aspect, the compositions are administered within the same 1-2 days, and in another aspect on the same day, and in another aspect within the same 12 hour period, and in another aspect within the same 8 hour period, and in another aspect within the same 4 hour period, and in another aspect within the same 1, 2 or 3 hour period, and in another aspect, within the same 1, 2, 3, 4, 6, 7, 8, 9, or 10 minutes.

In one embodiment of the invention, the yeast-based immunotherapy composition and the agent(s) are administered concurrently, but to different physical sites in the patient. For example, one composition or agent can be administered to one or more sites of the individual's body and the other composition or agent can be administered to one or more different sites of the individual's body, e.g., on different sides of the body or near different draining lymph nodes. In another embodiment, the immunotherapy composition and the agent are administered concurrently and to the same or substantially adjacent sites in the patient. A substantially adjacent site is a site that is not precisely the same injection site to which the first composition or agent is administered, but that is in close proximity (is next to) the first injection site. In one embodiment, the immunotherapy composition and agent are administered in admixture. Some embodiments may include combinations of administration approaches.

In the method of the present invention, compositions and therapeutic compositions can be administered to animal, including any vertebrate, and particularly to any member of the Vertebrate class, Mammalia, including, without limitation, primates, rodents, livestock and domestic pets. Livestock include mammals to be consumed or that produce useful products (e.g., sheep for wool production). Mammals to protect include humans, dogs, cats, mice, rats, goats, sheep, cattle, horses and pigs.

An "individual" is a vertebrate, such as a mammal, including without limitation a human. Mammals include, but are not limited to, farm animals, sport animals, pets, primates, mice and rats. The term "individual" can be used interchangeably with the term "animal", "subject" or "patient".

Screening, Research and Diagnostic Methods of the Invention

The invention also includes various screening methods and research or diagnostic methods related to the discovery of the dual TH1/TH17 immune response elicited by yeast-based immunotherapeutic compositions. In one embodiment, the invention includes a method to screen subjects for predicted TH1-mediated immune responsiveness to yeast-based immunotherapy. The method includes: (a) contacting T cells from a subject in vitro with antigen presenting cells (APCs) that have been contacted with a yeast-based immunotherapy composition; and (b) detecting a phenotype of the T cells selected from the group of: T cell proliferation in response to contact with the APCs, IL-17 production by the T cells in response to contact with the APCs, and expression of the transcription factor, retinoid-related orphan receptor (ROR), by T cells in response to contact with the APCs. Subjects whose T cells proliferate in response to contact with the APCs, or have normal production of IL-17 or normal expression of ROR, are predicted to be good candidates for administration of a yeast-based immunotherapeutic composition where a TH1-mediated response is desired. Subjects whose T cells fail to proliferate or proliferate poorly in response to contact with the APCs, or whose T cells produce greater than normal amounts of IL-17 or have greater than normal expression of ROR, are predicted to be candidates for administration of a yeast-based immunotherapeutic composition in conjunction with an agent that inhibits the production and/or survival of TH17 cells. Subjects whose T cells produce lesser than normal amounts of IL-17 or have lesser than normal expression of ROR, are predicted to be candidates for administration of a yeast-based immunotherapeutic composition in conjunction with an agent that increases the production or survival of TH17 cells. Agents that increase or decrease (upregulate or downregulate) the production, expression or survival of TH17 cells have been described herein.

According to this embodiment, a sample of T cells is obtained from the subject, typically in suspension, which have been collected from a tissue or organ (e.g., via a biopsy) or fluid (peripheral blood mononuclear cells) by any suitable method which results in the collection of a suitable number of T cells for evaluation by the method of the present invention.

T cell proliferation assays are well known in the art and are generally described previously herein. Detection of expression of cytokines and other proteins, such as RORγt, can be performed by detection of nucleic acids or proteins. Nucleic acid sequences can be detected by any suitable method or technique of measuring or detecting gene sequence or expression. Such methods include, but are not limited to, PCR, reverse transcriptase-PCR (RT-PCR), in situ PCR, in situ hybridization, Southern blot, Northern blot, sequence analysis, microarray analysis, detection of a reporter gene, or other DNA/RNA hybridization platforms. Proteins can be detected using antibodies, for example, in a format such as Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry.

Another embodiment of the invention includes a method to measure antigen-specific, CD8+ T cell responses to a yeast-based immunotherapy composition. The method includes: (a) immunizing a non-human animal with a yeast-based immunotherapy composition, wherein TH17 responses are inhibited or blocked in the non-human animal; (b) injecting the immunized non-human animal of (a) with a mixture of equal numbers of labeled target cells and labeled non-target cells, wherein the target cells express or display an antigen against which the yeast-based immunotherapy composition elicits a T cell response, wherein the non-target cells do not express or display the antigen, and wherein the target cells are labeled differently than the non-target cells; (c) collecting a population of cells from the non-human animal of (b) that contain the labeled target cells and labeled non-target cells; and (d) measuring antigen-specific CD8+ T cells in the non-human animal by detecting a difference in the ratio of target cells to non-target cells, wherein the reduction of target cells as compared to non-target cells indicates the level of antigen-specific, CD8+ T cell response in the non-human animal. In one aspect of this embodiment of the invention, the target cells are spleen cells that have been pulsed the peptides of the target antigen. In one aspect, the population of cells in (c) is from spleen. In one aspect, the target cells are tumor cells that express the target antigen. In one aspect, the population of cells in (c) is from liver. In one aspect, step (d) is performed using flow cytometry.

Another embodiment of the invention relates to a method to measure antigen-specific, CD8+ T cell responses to a yeast-based immunotherapy composition. The method includes: (a) immunizing a non-human animal with a yeast-based immunotherapy composition, wherein TH17 responses are inhibited or blocked in the non-human animal; (b) collecting a population of cells from the non-human animal of (a) that contain CD8+ T cells; and (c) measuring antigen-specific CD8+ T cell responses in the non-human animal by detecting the ability of CD8+ T cells in the population of (c) to detect antigen-MHC complexes. In one aspect, the population of cells in (c) is a population containing peripheral blood mononuclear cells. In one aspect, the antigen-MHC complexes are tetramers.

In either of the above-described methods to measure CD8+ T cell responses, the non-human animal can be any suitable non-human animal, and in one aspect is a rodent, such as a mouse. In one aspect, the expression or activity of a cytokine selected from: IL-1, IL-6, IL-17, IL-21, IL-22, or IL-23, is blocked or inhibited in the non-human animal. In one aspect, the non-human animal is an IL-6 homozygous knock-out mouse.

The conditions under which a cell, cell lysate, nucleic acid molecule or protein in any method described above is exposed to or contacted with another reagent or compound, such as by mixing, are any suitable culture or assay conditions.

General Techniques Useful in the Invention

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, Methods of Enzymology, Vol. 194, Guthrie et al., eds., Cold Spring Harbor Laboratory Press (1990); Biology and activities of yeasts, Skinner, et al., eds., Academic Press (1980); Methods in yeast genetics: a laboratory course manual, Rose et al., Cold Spring Harbor Laboratory Press (1990); The Yeast *Saccharomyces*: Cell Cycle and Cell Biology, Pringle et al., eds., Cold Spring Harbor Laboratory Press (1997); The Yeast *Saccharomyces*: Gene Expression, Jones et al., eds., Cold Spring Harbor Laboratory Press (1993); The Yeast *Saccharomyces*: Genome Dynamics, Protein Synthesis, and Energetics, Broach et al., eds., Cold Spring Harbor Laboratory Press (1992); Molecular Cloning: A Laboratory Manual, second edition (Sambrook et al., 1989) and Molecular Cloning: A Laboratory Manual, third edition (Sambrook and Russel, 2001), (jointly referred to herein as "Sambrook"); Current Protocols in Molecular Biology (F. M. Ausubel et al., eds., 1987, including supplements through 2001); PCR: The Polymerase Chain Reaction, (Mullis et al., eds., 1994); Harlow and Lane (1988) Antibodies, A Laboratory Manual, Cold Spring Harbor Publications, New York; Harlow and Lane (1999) Using Antibodies: A Laboratory Manual Cold Spring Harbor Laboratory Press, Cold Spring Harbor, N.Y. (jointly referred to herein as "Harlow and Lane"), Beaucage et al. eds., Current Protocols in Nucleic Acid Chemistry John Wiley & Sons, Inc., New York, 2000); Casarett and Doull's Toxicology The Basic Science of Poisons, C. Klaassen, ed., 6th edition (2001), and Vaccines, S. Plotkin and W. Orenstein, eds., 3rd edition (1999).

General Definitions

A "cell-mediated" immune response (which may be used interchangeably anywhere herein with the term "cellular" immune response) refers generally to the response to an antigen of immune cells including T lymphocytes (including cytotoxic T lymphocytes (CTL)), dendritic cells, macrophages, and natural killer cells, and to all of the processes that accompany such responses, including, but not limited to, activation and proliferation of these cells, CTL effector functions, cytokine production that influences the function of other cells involved in adaptive immune responses and innate immune responses, and memory T cell generation.

"Vaccination" or "immunization" refers to the elicitation (induction) of an immune response against an antigen or immunogenic portion thereof, as a result of administration of the antigen, alone or together with an adjuvant. Vaccination results in a protective or therapeutic effect, wherein subsequent exposure to the antigen (or a source of the antigen) elicits an immune response against the antigen (or source) that reduces or prevents a disease or condition in the animal. The concept of vaccination is well known in the art. The immune response that is elicited by administration of an immunotherapeutic composition (vaccine) can be any detectable change in any facet of the immune response (e.g., cell-mediated response, humoral response, cytokine production), as compared to in the absence of the administration of the composition.

According to the present invention, "heterologous amino acids" are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Therefore, at least two amino acid residues that are heterologous to the antigen are any two amino acid residues that are not naturally found flanking the antigen.

According to the present invention, reference to a "heterologous" protein or "heterologous" antigen, including a heterologous fusion protein, in connection with a yeast vehicle of the invention means that the protein or antigen is not a protein or antigen that is naturally expressed by the yeast, although a fusion protein may include yeast sequences or proteins or portions thereof that are naturally expressed by yeast (e.g., an Aga protein as described herein). For example, a fusion protein of an influenza hemagglutinin protein and a yeast Aga protein is considered to be a heterologous protein with respect to the yeast vehicle for the purposes of the present invention, since such a fusion protein is not naturally expressed by a yeast.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA), immunoblot assays, etc.).

Reference to a protein or polypeptide in the present invention includes full-length proteins, fusion proteins, or any fragment, domain, conformational epitope, or homologue of such proteins. More specifically, an isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. In one aspect of the invention, an isolated protein of the present invention is produced recombinantly. According to the present invention, the terms "modification" and "mutation" can be used interchangeably, particularly with regard to modifications/mutations to the amino acid sequence of proteins or portions thereof.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, or substantially similar properties as compared to the naturally occurring protein or peptide. A homologue can include an agonist of a protein or an antagonist of a protein. Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

A homologue of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and in one aspect of the present invention, is a virus or a plasmid. Recombinant vectors can be used in the cloning, sequencing, and/or otherwise manipulating of nucleic acid molecules, and can be used in delivery of such molecules (e.g., as in a DNA vaccine or a viral vector-based vaccine). Recombinant vectors may be used in the expression of nucleic acid molecules, and can also be referred to as expression vectors. Some recombinant vectors are capable of being expressed in a transfected host cell.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

The following experimental results are provided for purposes of illustration and are not intended to limit the scope of the invention.

EXAMPLES

Example 1

The following example demonstrates the generation of primary, antigen-specific CD8+ T cell-mediated immunity with whole yeast-based immunotherapy immunization.

It has been previously shown that immunization of mice with yeast engineered to express ovalbumin leads to the generation of cell-mediated destruction of ovalbumin expressing tumors (Stubbs et al., *Nat. Med.* 7:625-629 (2001)). Efficient tumor destruction in vivo required CD8+ T cells and was generated following at least two immunizations.

Using enhanced immunization procedures, the inventors determined whether detectable primary, antigen specific $CD8^+$ cell-mediated immune responses could be generated. The first approach, based on the premise that primary antigen-specific immune responses would be easier to detect if the frequency of antigen-specific T cells was improved, involved adoptive transfer of T cells from the OT-1 transgenic mice, where the T cell repertoire is dominated by $CD8^+$ T cells bearing a single T cell receptor specific for the immunodominant ovalbumin peptide, SIINFEKL (SEQ ID NO:26). One immunization with whole *Saccharomyces cerevisiae* yeast engineered to recombinantly express ovalbumin (called OVAX) lead to the activation and expansion of adoptively transferred OT-1 $CD8^+$ T cells, as defined by dilution of CFSE staining (FIG. 1A). Similar results were observed with a mixture of soluble ovalbumin (ova) and *Saccharomyces cerevisiae* yeast transformed with only the CUP1 promoter plasmid (YVEC) (YVEC+ova; FIG. 1B). No ovalbumin specific T cell activation was observed with YVEC yeast alone (FIG. 1C) or in naïve adoptive recipients (FIG. 1D). These results confirmed previous studies, where it was concluded that yeast can induce cross presentation of soluble antigen in vitro (Stubbs et al., 2001, supra; Haller et al., 2007, *Vaccine* 25:

1452-1463), although the present experiment demonstrated cross presentation using an in vivo approach.

CD40 signaling matures dendritic cells via cytokine production, induction of costimulatory molecules such as MHC Class II and CD80/86, and by facilitating cross presentation, all of which are considered to provide more efficient T cell activation and differentiation.

In order to optimize and increase the sensitivity of the yeast-based immunization approach such that endogenous antigen-specific CD8+ T cells could be generated with a single immunization (i.e., a primary response), the inventors used a mixture of yeast along with soluble antigen, in this case ovalbumin, and antibody to the dendritic cell (DC) activation antigen, CD40 (αCD40 or aCD40). Briefly, C57B1/6 wild-type (WT) mice were immunized once intravenously with various combinations of YVEC, soluble ovalbumin, and/or anti-CD40 (an antibody targeting the CD40 molecule on antigen presenting cells) as shown in FIGS. 2A-2D. Seven days later, peripheral blood lymphocytes were isolated from a blood sample. The peripheral blood cells were stained for the CD44 marker expressed on activated T cells (Y axis) as well as ovalbumin antigen-specific CD8+ T cells (X axis). The flow cytometry histograms show the relative number of cells in the sample that stain for both the T cell activation marker and the antigen-specific marker which indicates a productive immune response. The cells that stain for both markers run in the upper right quadrant of the histogram.

Figures 2A, 2B, 2C, 2D:
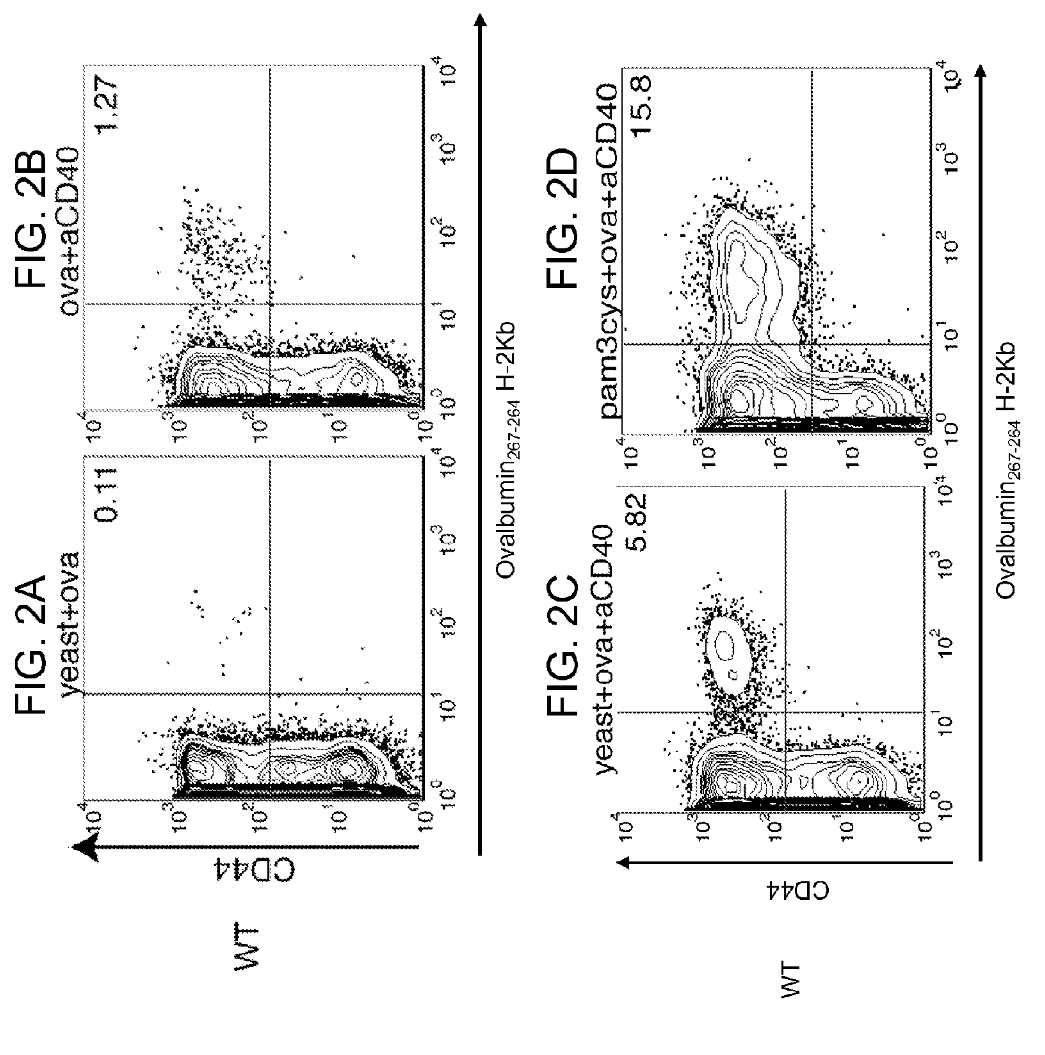
FIGS. 2A-2D are flow cytometry graphs showing the generation of primary, antigen-specific CD8+ T cell responses in wild-type mice immunized with yeast plus ovalbumin (FIG. 2A), ovalbumin plus anti-CD40 (FIG. 2B), yeast plus ovalbumin and anti-CD40 (FIG. 2C) and pam3cys plus ovalbumin and anti-CD40 (FIG. 2D).

As compared to the results shown in FIGS. 1A-1D above, even more vigorous primary responses were observed when anti-CD40 antibody was included in the experiment (see FIGS. 2A-2D). Anti-CD40 antibody was used as a means to engage CD40 on antigen presenting cells, as this is believed to provide more efficient antigen presentation (Ahonen et al, 2009). This immunization approach, where anti-CD40 antibody was combined with ovalbumin and yeast (yeast+ova+aCD40), led to demonstrable tetramer positive, endogenous OVA antigen-specific CD8+ T cells in a wild type (WT) animal (FIG. 2C), compared to yeast plus ovalbumin alone (yeast+ova; FIG. 2A) or ovalbumin plus anti-CD40 alone (ova+aCD40; FIG. 2B). The generation of endogenous, primary antigen-specific CD8+ T cells eliminated the need for OT-1 transgenic T cell adoptive transfer in order to embellish the primary immune response signal. While yeast plus ovalbumin plus anti-CD40 antibody generated an antigen specific CD8 frequency of about 5% (FIG. 2C), immunization with the TLR2 agonist, pam3cys, in combination with ovalbumin and anti-CD40 (FIG. 2D) generated approximately a three-fold (5.8 versus 15.8) increase in antigen-specific CD8+ T cells as compared to the yeast immunization (FIG. 2C).

Example 2

The following example shows that TLR-dependent generation of primary antigen-specific CD8+ cell-mediated immunity with whole yeast-based immunization is demonstrably influenced by IL-12 and CD4+ TH1 T cells.

This series of experiments investigated what relationship exists between the yeast-based generation of TH1 T cells and antigen-specific CD8+ T cells, and whether the cell-mediated immune response could be modulated by inhibiting certain types of immune responses.

The inventors initially focused on whole yeast-based immune responses generated in mice deficient in the ability to recognize yeast-associated, pathogen molecular patterns; mice deficient in the Th1-specific transcription factor, Tbet; and mice unable to recognize the TH1-associated cytokine, IL-12. Yeast engage Toll-Like Receptors (TLRs) on antigen presenting cells, and the most likely TLRs engaged by yeast are believed to be TLR 2 and 4, both of which are Myd88 signaling-dependent. Tbet is the Th1-specific transcription factor, and mice lacking the gene encoding Tbet do not produce Th1-type CD4+ T cells. IL-12 is a cytokine associated with TH1 induction that is initiated by engaging TLRs on DCs (Pasare and Medzhitov, 2003).

Figures 4A, 4B, 4C:
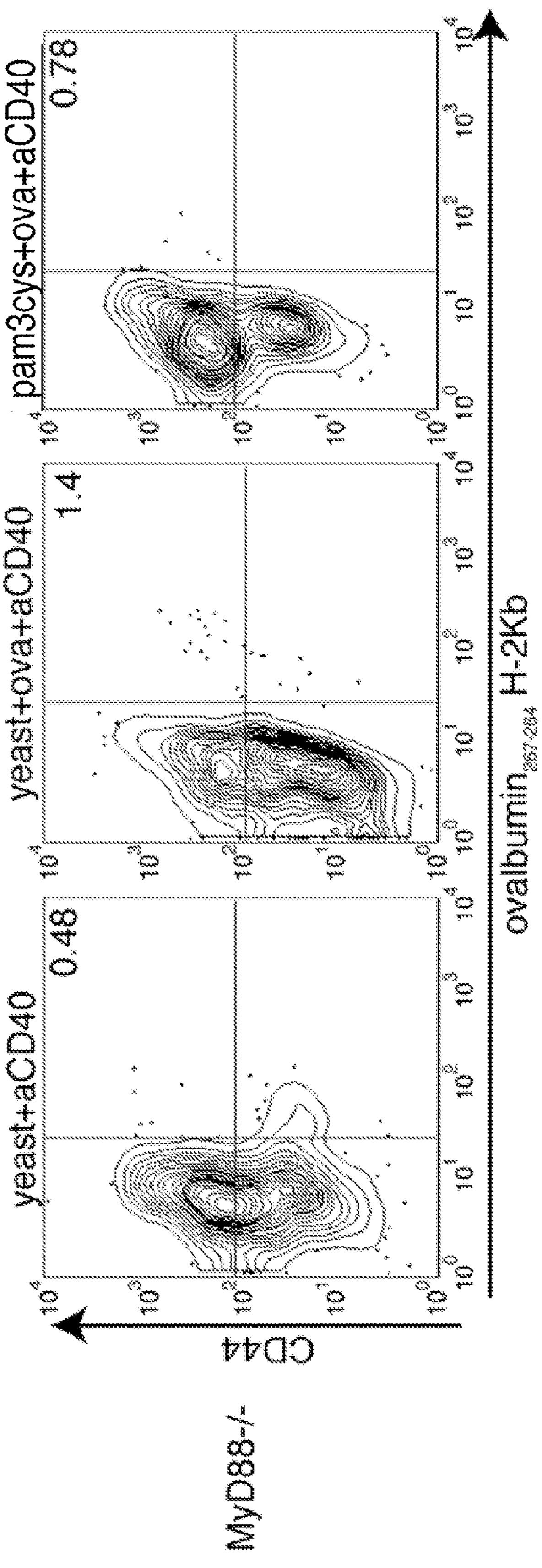
FIGS. 4A-4C are flow cytometry graphs showing the generation of primary, antigen-specific CD8+ T cell responses in MyD88 knockout mice immunized with yeast plus anti-CD40 (FIG. 4A), yeast plus ovalbumin and anti-CD40 (FIG. 4B) and pam3cys plus ovalbumin and anti-CD40 (FIG. 4C).
Figure 5:
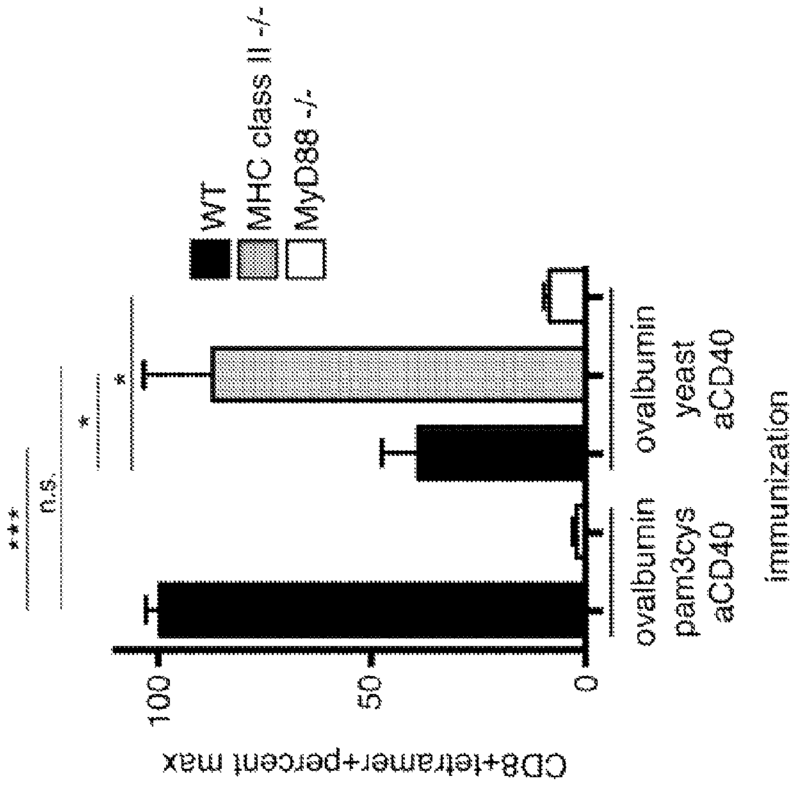
FIG. 5 is a bar graph showing the percentage of CD8+ T cells generated in wild-type mice (WT, black bars), mice lacking the TLR signaling protein MyD88 (MyD88−/−, white bars), or mice lacking CD4+ T cells (MHC Class II−/−, gray bar), as compared on the Y axis with the frequency of antigen specific CD8+ T cells generated in response to pam3cys in WT mice (represented as 100% in the first row).

Briefly, different groups of mice (described below) were immunized once intravenously with various combinations of YVEC (yeast containing an empty vector, denoted "yeast"), soluble ovalbumin (ova), the TLR2 agonist known as pam3cys, and/or anti-CD40 (aCD40; an antibody targeting the CD40 molecule on antigen presenting cells) as indicated in FIGS. 3-5. In some experiments, naïve animals were included, which were not immunized (denoted "naïve"). Seven days later, peripheral blood lymphocytes were isolated from a blood sample, and the peripheral blood cells were stained for the CD44 marker expressed on activated T cells (FIGS. 3 and 4, Y axis) as well as ovalbumin antigen-specific CD8+ T cells (FIGS. 3 and 4, X axis), as described in the experiments in Example 1 above.

Figures 3A, 3B, 3C, 3D, 3E, 3F, 3G, 3H, 3I:
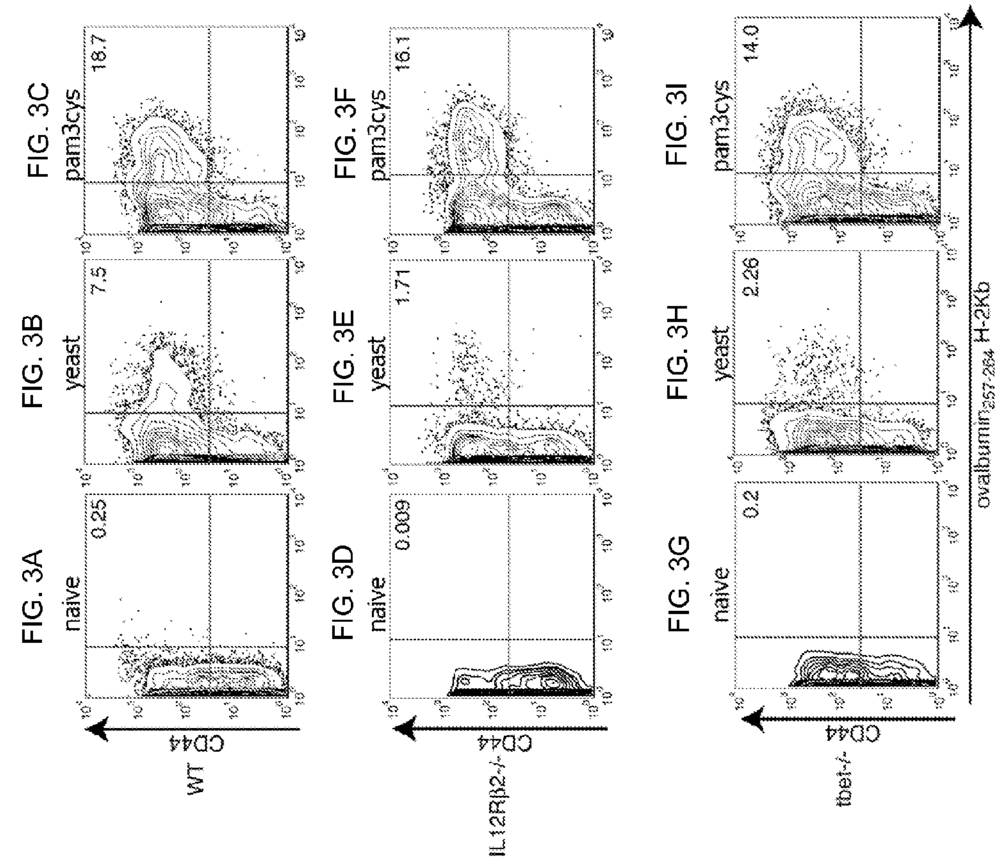
FIGS. 3A-3C are flow cytometry graphs showing the generation of primary, antigen-specific CD8+ T cell responses in wild-type mice (WT): not immunized (naïve, FIG. 3A), immunized with yeast plus ovalbumin and anti-CD40 (yeast, FIG. 3B), and immunized with pam3cys plus ovalbumin and anti-CD40 (pam3cys, FIG. 3C).
FIGS. 3D-3F are flow cytometry graphs showing the generation of primary, antigen-specific CD8+ T cell responses in IL-12Rβ knockout mice (IL-12Rβ−/−): not immunized (na- ïve, FIG. 3D), immunized with yeast plus ovalbumin and anti-CD40 (yeast, FIG. 3E), and immunized with pam3cys plus ovalbumin and anti-CD40 (pam3cys, FIG. 3F).
FIGS. 3G-3I are flow cytometry graphs showing the generation of primary, antigen-specific CD8+ T cell responses in tbet knockout mice (tbet−/−): not immunized (naïve, FIG. 3G), immunized with yeast plus ovalbumin and anti-CD40 (yeast, FIG. 3H), and immunized with pam3cys plus ovalbumin and anti-CD40 (pam3cys, FIG. 3I).

FIGS. 3A-3I show the results of an experiment to evaluate the requirement for TH1 activation for CD8+ responses generated by yeast-based immunotherapeutics. IL-12Rβ−/− mice lack an IL-12 receptor subunit and are accordingly rendered deficient in IL-12-induced biological functions. Tbet−/− mice lack the major transcription factor, Tbet, that is associated with production of TH1 cells and are accordingly deficient in TH1 CD4+ T cells. Wild-type mice (WT; FIGS. 3A-3C), IL-12Rβ−/− mice (FIGS. 3D-3F) and tbet−/− mice (FIGS. 3G-3I) were immunized with (1) nothing (denoted "naïve"; FIGS. 3A, 3D, 3G), (2) YVEC plus soluble ovalbumin plus anti-CD40 (denoted "yeast"; FIGS. 3B, 3E, 3H), or (3) pam3cys plus soluble ovalbumin plus anti-CD40 (denoted "pam3cys"; FIGS. 3C, 3F, 3I).

The upper right quadrant of each panel in FIGS. 3A-3I represents the percentage of antigen-specific CD8+ T cells produced; for example, using WT mice, yeast-based immunization (FIG. 3B) generated approximately 40% the frequency of CD8 T cells compared to pam3cys-immunization (FIG. 3C) (7.5% vs 18.7%, respectively).

In mice unable to develop TH1 CD4+ T cells (tbet−/− mice) (Szabo et al, 2000) the yeast-generated response was reduced essentially to background (FIG. 3H). A similar outcome occurred by eliminating the IL-12-dependent TH1 responses in mice lacking the IL-12 receptor (FIG. 3E). Neither interfering with IL-12 receptivity nor eliminating TH1 CD4+ T cells had any significant effect on pam3cys responses (FIGS. 3F and 3I). These data indicated that pam3cys and yeast differed in several important ways. First, knocking out the CD4+ TH1 subset, or the principal cytokine (IL-12) derived by dendritic cells (DCs) that drives this response, dropped CD8+ T cell generation to or near background levels in yeast-immunized animals while having no apparent effect on pam3cys generation of CD8+ T cells. Thus, the yeast-based immunization generated a TH1 CD4-dependent and an IL-12-dependent response, while the pam3cys response was neither TH1 CD4-dependent nor IL-12-dependent. Second, it appears that the pam3cys response is more robust, approximately 2.5× in magnitude compared to yeast, with the caveat that the experiments are performed in normal (wild-type) mice, as shown in FIGS. 3A-3C.

To determine what signals are required for CD8+ T cells to become activated in response to yeast-based immunotherapy versus pam3cys immunotherapy, FIGS. 4A-4C and FIG. 5 show the results of experiments to evaluate the requirement for TLR signaling and MHC Class II signaling for CD8+ responses generated by these therapeutic approaches. MyD88−/− mice are C57B1/6 mice in which all of the Toll-Like Receptors (TLRs) except TLR3 have been rendered dysfunctional (i.e., all TLRs except TLR3 require MyD88 for productive signaling). Class II MHC knockout mice (MHC Class II−/−) are mice which are negative for MHC Class II molecules, rendering the mice devoid of all types of CD4+ T cells.

In a first experiment, MyD88−/− mice were immunized with: (1) YVEC plus anti-CD40 (yeast+aCD40; FIG. 4A), (2) YVEC plus soluble ovalbumin plus anti-CD40 (yeast+ova+aCD40; FIG. 4B), or (3) pam3cys plus ovalbumin plus anti-CD40 (pam3cys+ova+aCD40; FIG. 4C). These results show that rendering all TLRs except TLR3 dysfunctional leads to a marked diminution, if not elimination, of the immune response in both yeast-immunized and pam3cys-immunized mice, indicating that both responses are dependent upon functional TLR signaling. By comparing FIGS. 2A-2D with FIGS. 4A-4C, responses to yeast+ova+anti-CD40 went from 5.8% to 1.4% while responses with pam3cys+ova+anti-CD40 went from 15.8% to 0.78%.

In a second experiment shown in FIG. 5, the percentage of CD8+ T cells generated in mice lacking the TLR signaling protein MyD88 (MyD88−/−) are compared on the Y axis with the frequency of antigen specific CD8+ T cells generated in response to pam3cys in WT mice (represented as 100% in the first column). Wild-type (WT; black bars) or MyD88−/− mice (white bars) were immunized with: (1) YVEC plus ovalbumin plus anti-CD40 (ovalbumin, yeast, aCD40) or (2) pam3cys plus ovalbumin plus anti-CD40 (ovalbumin, pam3cys, aCD40). In this experiment, it can be observed that the response to yeast-based immunization of WT mice was 40% of that observed for pam3cys (as shown also in earlier figures). As in FIG. 4, it can also be observed that the absence of the MyD88 receptor, which is essential for TLR2 and all other TLR signaling except TLR3, essentially eliminates the response to both yeast and pam3cys (FIG. 5, compare lanes 2 and 5 vs. lane 1) (*$p<0.05$, *$p<0.0001$). Taken together, the experiments in FIGS. 4 and 5 demonstrate that MyD88-dependent TLRs (except TLR3) were required for both yeast and pam3cys CD8+ T cell responses, since responses dropped to near background levels when MyD88 was not operative (FIG. 5**, lanes 2 and 5).

The inventors also investigated the impact of eliminating all CD4 T cell subsets on the generation of antigen specific CD8+ T cells via yeast-based immunization by performing an experiment in Class II MHC knockout mice (i.e., mice devoid of all types of CD4+ T cells). The results are shown in FIG. 5 (gray bar, col. 4). FIG. 5 shows that, whereas the yeast-based CD8+ T cell response was reduced to background levels as compared to pam3cys treatment in MyD88−/− animals lacking only TH1 CD4+ T cells (white bars), a CD8+ T cell response to yeast was produced and indeed, was nearly equivalent to that elicited by pam3cys treatment, when all CD4+ T cell subsets were missing in the Class II MHC−/− animal (FIG. 5, compare row 1 with row 4). Elimination of CD4+ T cells had no impact on pam3cys treated Class II MHC−/− mice as compared to WT mice (data not shown).

In other words, while the pam3cys response in wild-type mice was approximately 2.5× higher than that generated by yeast-based immunization (see FIGS. 3B and 3C), in the animals deficient in all CD4+ T cells, the yeast and pam3cys responses were comparable. Taken together, these results indicate that CD4+ T cells regulate the CD8+ T cell response to yeast in ways that are distinct from the immune response to the pam3cys TLR-specific stimulus. While yeast are capable of provoking a CD4-independent CD8 T cell response comparable to that observed with the CD4-independent TLR agonist pam3cys, with the caveat that the experiments are performed in animals devoid of CD4 T cells, unlike pam3cys treatment, they can also provoke a TH1 CD4-dependent/IL-12-dependent CD8+ T cell response that is influenced by yet another CD4 subset, confirming a role for yeast-generated CD4 T cells in both inducing and regulating the response to yeast-based immunotherapy.

Example 3

The following example shows that TLR-dependent generation of a primary antigen-specific CD8+ cell-mediated immunity with whole yeast-based immunization is demonstrably influenced by IL-6.

This series of experiments investigated what relationship, if any, exists between the yeast-based generation of TH1 T cells and antigen-specific CD8+ T cells, and the generation of other T cell subsets, such as TH17 T cells, and further, whether the cell-mediated immune response could be modulated by inhibiting certain types of immune responses. The experiments utilized mice deficient in the ability to produce the proinflammatory and TH17-related cytokine, IL-6. TH17 production is favored by the engagement of receptors such as Dectin-1 which bind to yeast-derived beta glucans, leading to IL-6 production (Korn et al, 2008; Dennehey et al, 2009).

With the demonstration in Example 2 that CD4+ TH1 cells are the inducers of a CD4-dependent CD8+ response to yeast-based immunotherapy when the CD4+ T cell populations are intact, the inventors next sought to determine which CD4 subset was responsible for regulating the response to yeast immunotherapy.

Figures 6A, 6B, 6C:
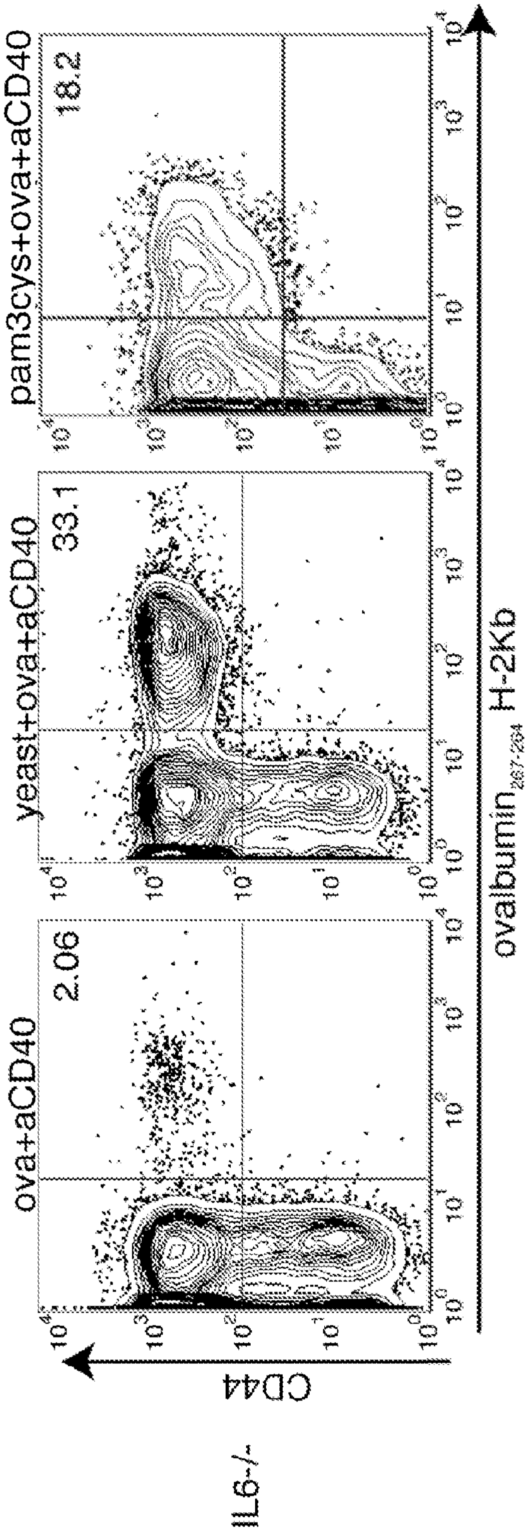
FIGS. 6A-6C are flow cytometry graphs showing the generation of primary, antigen-specific CD8+ T cell responses in IL-6 knockout mice immunized with ovalbumin plus anti-CD40 (FIG. 6A), yeast plus ovalbumin and anti-CD40 (FIG. 6B) and pam3cys plus ovalbumin and anti-CD40 (FIG. 6C).

The controlling CD4 population elicited by yeast-based immunotherapy is IL-6-dependent as shown in FIGS. 6A-6C. This experiment evaluated the requirement for IL-6 in the immune responses generated by yeast-based immunotherapy. IL-6−/− mice are C57B1/6 mice that do not have the capacity to produce IL-6 (IL-6 knockout mice). IL-6−/− mice were immunized with (1) ovalbumin plus anti-CD40 (ova+aCD40; FIG. 6A), (2) YVEC plus soluble ovalbumin plus anti-CD40 (yeast+ova+aCD40; FIG. 6B), or (3) pam3cys plus ovalbumin plus anti-CD40 (pam3cys+ova+aCD40; FIG. 6C). Seven days later, peripheral blood lymphocytes were isolated from a blood sample, and the peripheral blood cells were stained for the CD44 marker expressed on activated T cells (Y axis) as well as ovalbumin antigen-specific CD8+ T cells (X axis), as described in the experiments in Example 1 above.

While immunization of IL-6 deficient animals with pam3sys+ova+anti-CD40 had no clear effect as compared to WT controls (18.2% vs 15.8%, comparing FIG. 6C to FIG. 2D), immunization with yeast+ova+anti-CD40 in an IL-6 deficient environment dramatically improved responses, e.g., by six-fold (33.1% vs 5.82%, comparing FIG. 6B to FIG. 2C), comparing to the immunization of WT mice with the same combination of yeast, antigen and anti-CD-40. In other experiments (data not shown), the frequency of antigen-specific CD8+ T cells was enhanced by as much as 25-fold or more in IL-6−/− mice as compared to WT mice. Indeed, elimination of IL-6, while leaving CD4 T cells intact, actually increases the CD8+ T cell frequencies in the response to yeast-based immunotherapy to values that were reproducibly twice the maximum observed for pam3cys treatment (FIGS. 6B and 6C). Therefore, an IL-6-dependent CD4+ T cell population is responsible for controlling CD8+ T cell responses to yeast-based immunotherapy, but not to pam3cys-based immunotherapy, and elimination of IL-6-dependent regulation resulted in a dramatically elevated CD8+ response to yeast-based immunization.

Figure 7:
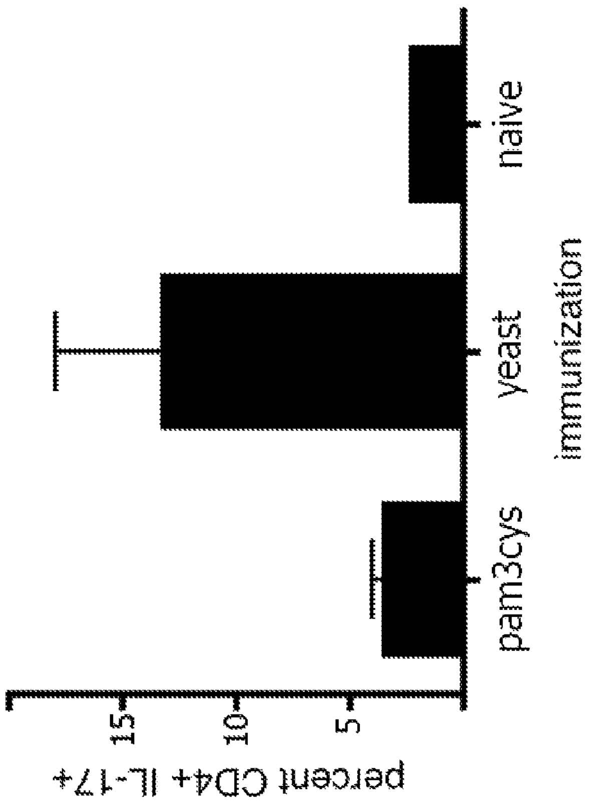
FIG. 7 is a bar graph showing the frequency of CD4+ T cells producing IL-17 (Y-axis) produced by naïve mice (not immunized), by mice immunized with pam3cys plus ovalbumin and anti-CD40 (pam3cys), and by mice immunized with yeast plus ovalbumin and anti-CD40 (yeast).

Referring to FIG. 7, the inventors then showed that the IL-6-dependent CD4+ T cell population that regulated the yeast-based immunotherapeutic response was the CD4+ TH17 T cell population, as defined by IL-17 production. In this experiment, wild-type (WT) mice were immunized with yeast (YVEC plus ovalbumin plus anti-CD40) or pam3cys (pam3cys plus ovalbumin plus anti-CD40) as described above, and peripheral blood was examined 7 days later for the frequency of CD4+ T cells producing IL-17 (as defined by intracellular cytokine staining developed via flow cytometry). On the Y axis, the percentage of IL-17-producing CD4+ T cells generated from pam3cys treatment is less than 5% and is not significantly greater than the response observed in naïve mice (column 1 versus 3), while the percentage of TH17 in animals treated with yeast-based immunotherapy can be as high as 15% (most pronounced when TH1 cells are eliminated, data not shown).

Given the data shown above, wherein the absence of IL-6 enhanced the generation of antigen-specific CD8+ T cells with yeast-based immunization but not pam3cys immunization, the frequencies of TH17 T cells following yeast-based immunization were analyzed. The approach was to look for intracellular IL-17 production of CD4+ T cells using flow cytometry. Briefly, T cells were isolated from spleen and lung and examined for cytokine production immediately following a five hour pulse with PMA to develop cytokine. Using this approach in wild-type mice, it was difficult to reproducibly detect TH17 by measuring IL-17 production even after whole yeast-based immunization under optimal conditions. TH17 signals have been previously detected in other systems using an extended in vitro stimulation step which utilizes TH17-inducing cytokines as a means to enhance the TH17 signal. However, to avoid the potential confounding influences, of such methods, the inventors chose instead to examine TH17 in a T-bet knockout mouse, where TH1 T cells are deficient due to the lack of this critical TH1 transcription factor (see, e.g., Koch et al., 2009).

Figure 8A:
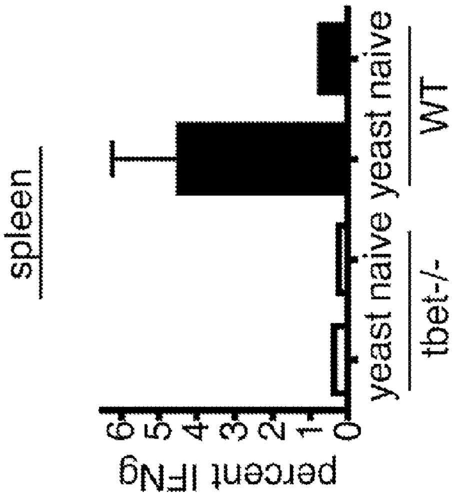
FIGS. 8A-8B are bar graphs showing the percentage interferon-γ produced in the spleen (FIG. 8A) and lung (FIG. 8B) of tbet knockout and wild-type mice following immunization with a yeast-based immunotherapy composition.
Figure 8B:
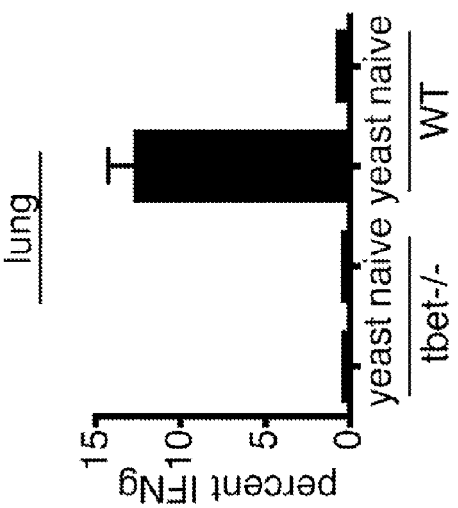

Referring to FIGS. 8A (spleen) and 8B (lung), interferon-γ-producing CD4+ T cells (percent IFNg) were not observed in the T-bet knockout after yeast-based (yeast) immunization (FIGS. 8A and 8B (see tbet−/− columns)) or pam3cys immunization (data not shown), while they were readily enhanced in frequency following whole yeast-based immunization in WT mice (FIGS. 8A and 8B, (WT, yeast)).

Figure 8C:
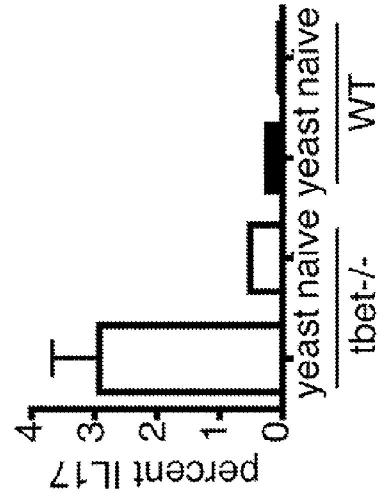
FIGS. 8C-8D are bar graphs showing the percentage interleukin-17 (IL-17) produced in the spleen (FIG. 8C) and lung (FIG. 8D) of tbet knockout and wild-type mice following immunization with a yeast-based immunotherapy composition.
Figure 8D:
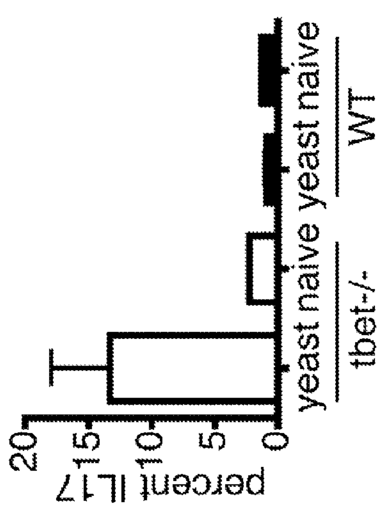

In the T-bet knockout mice immunized with yeast, TH17 cells could be directly detected ex vivo in non-manipulated animals and their frequencies increased in spleen (FIG. 8C) and lung (FIG. 8D) as a function of immunization with yeast. This increase in IL-17 producing CD4 T cells was not observed if the T-bet knockout mice were immunized with pam3cys (data not shown). Therefore, yeast-based immunization is associated with an increase in both interferon-γ-producing and IL-17-producing CD4 T cells.

These results show that the frequency of IL-17 producing CD4 T cells is increased following whole yeast-based immunization in a T bet knockout mouse that is deficient in TH1 T cell development. This demonstrates that TH17 CD4 T cells develop following presentation of yeast. In addition, these results demonstrate that yeast can also induce CD4 T cells with a TH1 phenotype. The demonstration that TH17 are increased in the T-bet knockout, TH1-deficient environment and that TH1 are increased in an IL-6-deficient environment indicates that both TH1 and TH17 are induced by whole yeast-based immunization, and that the immune responses can be modulated by manipulation of the immunization system or process.

Therefore, yeast-based immunotherapy can generate CD8+ T cells via a TH1-dependent process influenced/controlled by TH17 cells that are in turn induced by an IL-6 dependent process. One important difference between the TLR (MyD88-dependent) agonists, such as pam3cys, and yeast is that yeast likely engage multiple C-type lectin receptors on dendritic cells, such as dectins and mannose receptors, due to the presence of glucans and mannans on the yeast surface (LeibundGut-Landmann et al, 2007; Netea et al, 2008; Robinson et al, 2009; Ferwerda et al, 2009; Glocker et al, 2009; Geitjenbeek and Gringhuis, 2009). Induction through the C-type lectin receptors leads to IL-6 production, the interference with the IL-12 dependent pathway of TH1 generation and the promulgation of another CD4 population, TH17 (Dennehy and Brown, 2009). As pam3cys is in essence exclusively a TLR agonist (i.e. without substantive C-type lectin receptor activation) (Chen et al, 2009), no interference effect on with TH1, IL-12 or IL-6 was observed, and therefore, the pam3cys-specific response generated appears to be essentially IL-12- and CD4-independent.

Example 4

The following example shows that TLR-dependent generation of a primary antigen-specific CD8+ cell-mediated immunity with whole yeast-based immunization is not demonstrably influenced by the Dectin-1 receptor alone.

Figures 9A, 9B, 9C:
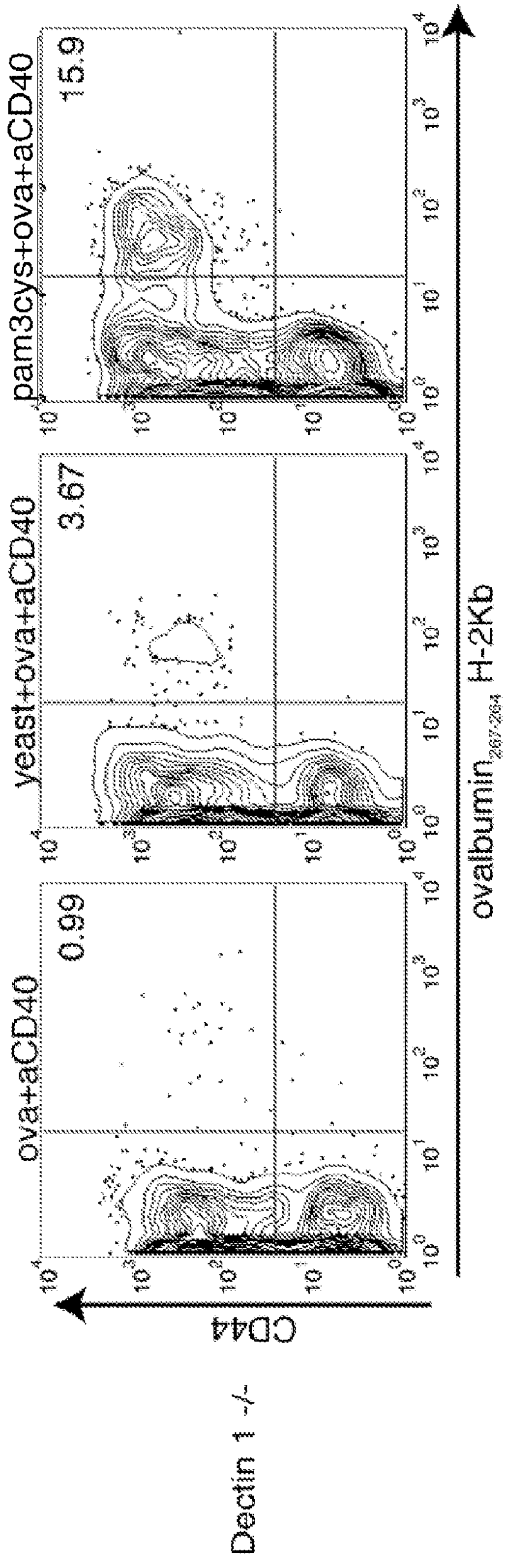
FIGS. 9A-9C are flow cytometry graphs showing the generation of primary, antigen-specific CD8+ T cell responses in Dectin-1 knockout mice (Dectin 1−/−) immunized with ovalbumin plus anti-CD40 (FIG. 9A), yeast plus ovalbumin and anti-CD40 (FIG. 9B) and pam3cys plus ovalbumin and anti-CD40 (FIG. 9C).

FIGS. 9A-9C show the results of an experiment to evaluate the requirement for signaling through the dectin-1 receptor in immune responses generated by yeast-based immunotherapeutics. Dectin 1−/− mice lack dectin-1, which is the myeloid receptor for β-glucan. Yeast-based immunotherapeutic compositions engage not only TLRs such as 2 and 4 but also express sugar residues (e.g., β-glucans) that bind the dectin-1 receptor on APCs. The literature reports that engaging dectin 1 is one pathway leading to IL-6 production. Dectin-1 knockout mice may productively engage TLR without dectin-1 receptor engagement. Dectin-1−/− mice were immunized with (1) ovalbumin plus anti-CD40 (ova+aCD40; FIG. 9A), (2) YVEC plus soluble ovalbumin plus anti-CD40 (yeast+ova+aCD40; FIG. 9B), or (3) pam3cys plus ovalbumin plus anti-CD40 (pam3cys+ova+aCD40; FIG. 9C). Seven days later, peripheral blood lymphocytes were isolated from a blood sample, and the peripheral blood cells were stained for the CD44 marker expressed on activated T cells (Y axis) as well as ovalbumin antigen-specific CD8+ T cells (X axis), as described in the experiments in Example 1 above. Results did not show a clearly demonstrable effect of Dectin-1 receptivity on responses for yeast+ova+aCD40 (3.67% vs 5.82%, comparing FIG. 9B to FIG. 2C) or pam3cys+ova+anti-CD40 (15.9% vs 15.8%, comparing FIG. 9C to FIG. 2D).

Given that the Dectin-1 receptor is considered to be an important phagocytic receptor leading to the induction of IL-6, it might have been expected that knocking out this receptor would diminish TH17 responses and with it, increase primary CD8+ responses in immunized mice. However, referring to FIGS. 9A-9C, the antigen-specific CD8 response by Dectin-1 knockout mice appeared to be comparable to that observed with WT mice in both yeast-immunized and pam3cys immunized mice. The Dectin-1 knockout mouse also had reductions in Treg frequency comparable to that which was observed for the WT mice (data not shown), suggesting demonstrable TH17 cells were induced as a result of yeast-based immunotherapy immunization in these mice.

Without being bound by theory, the inventors believe that the simplest interpretation of this data is that IL-6 can be produced as a result of engagement of other receptors in addition to the Dectin-1 receptor. Since the yeast express mannan on the cell surface in large quantity, one likely source is the mannan receptor that also engages IL-6 production, Dectin-2, or DC-SIGN.

Example 5

The following example describes additional experiments showing that CD8+ antigen-specific T cell responses can be modulated by modulating the CD4+ T cell response induced by yeast-based immunotherapy.

In this additional exemplary experiment, MyD88−/− mice (FIG. 10A), wild-type (WT) mice (FIG. 10B), and IL-6−/− mice (FIG. 10C) were immunized once intravenously with whole *Saccharomyces cerevisiae* yeast that have been genetically modified (by recombinant technology) to express ovalbumin (OVAX). Mice were immunized with OVAX and an antibody targeting the CD40 molecule on antigen presenting cells (anti-CD40). Seven days later, peripheral blood lymphocytes were isolated from a blood sample. The peripheral blood cells were stained for the CD44 marker expressed on activated T cells (FIGS. 10A-10C, Y axis) as well as ovalbumin antigen-specific CD8+ T cells (FIGS. 10A-10C, X axis).

Confirming the results shown in Examples 2 and 3, the data show that MyD88−/− mice (left) lack the ability to generate antigen-specific T cells since they lack the ability to signal via TLRs using the MyD88 pathway (all but TLR3). The data also confirm that deleting the ability to produce IL-6 dramatically improves the number of ovalbumin-specific CD8 T cells as compared to WT mice, as shown in Example 4. These data confirm that the generation of antigen-specific CD8+ T cell responses to yeast-based immunotherapy can be influenced by IL-6 and TLR engagement, or inhibition thereof, and that this occurs whether the ovalbumin is recombinantly produced by the yeast (this example) or mixed with the yeast (Examples 2-4).

Figures 10A, 10B, 10C:
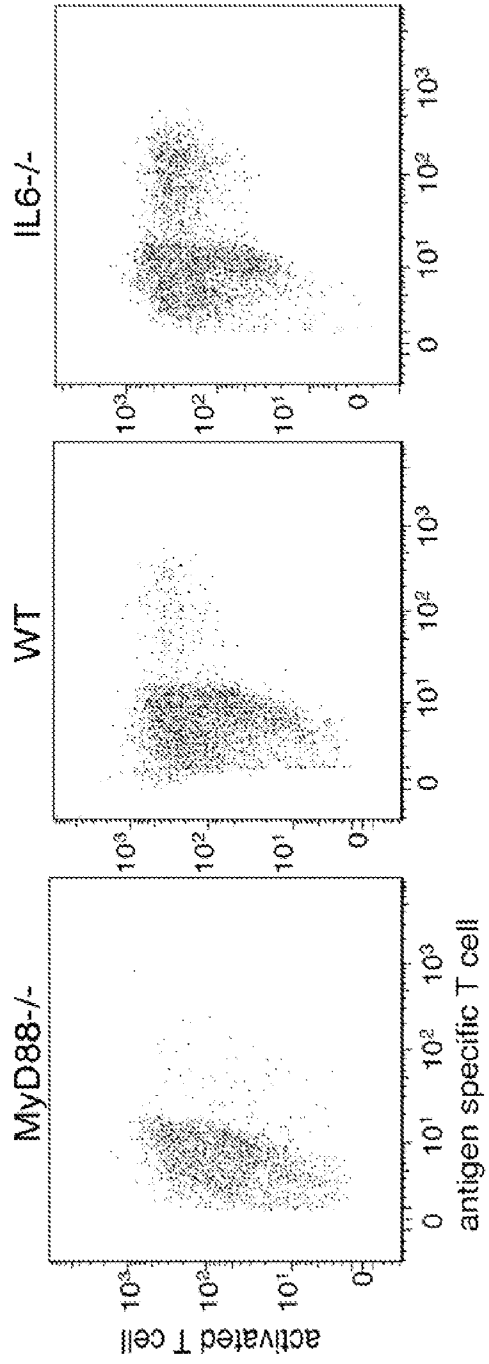
FIGS. 10A-10C are flow cytometry graphs showing the generation of primary, antigen-specific CD8+ T cell responses in MyD88 knockout mice (FIG. 10A), wild-type mice (FIG. 10B), and IL-6 knockout mice (FIG. 10C) after immunization with yeast, ovalbumin and anti-CD40.
Figure 11:
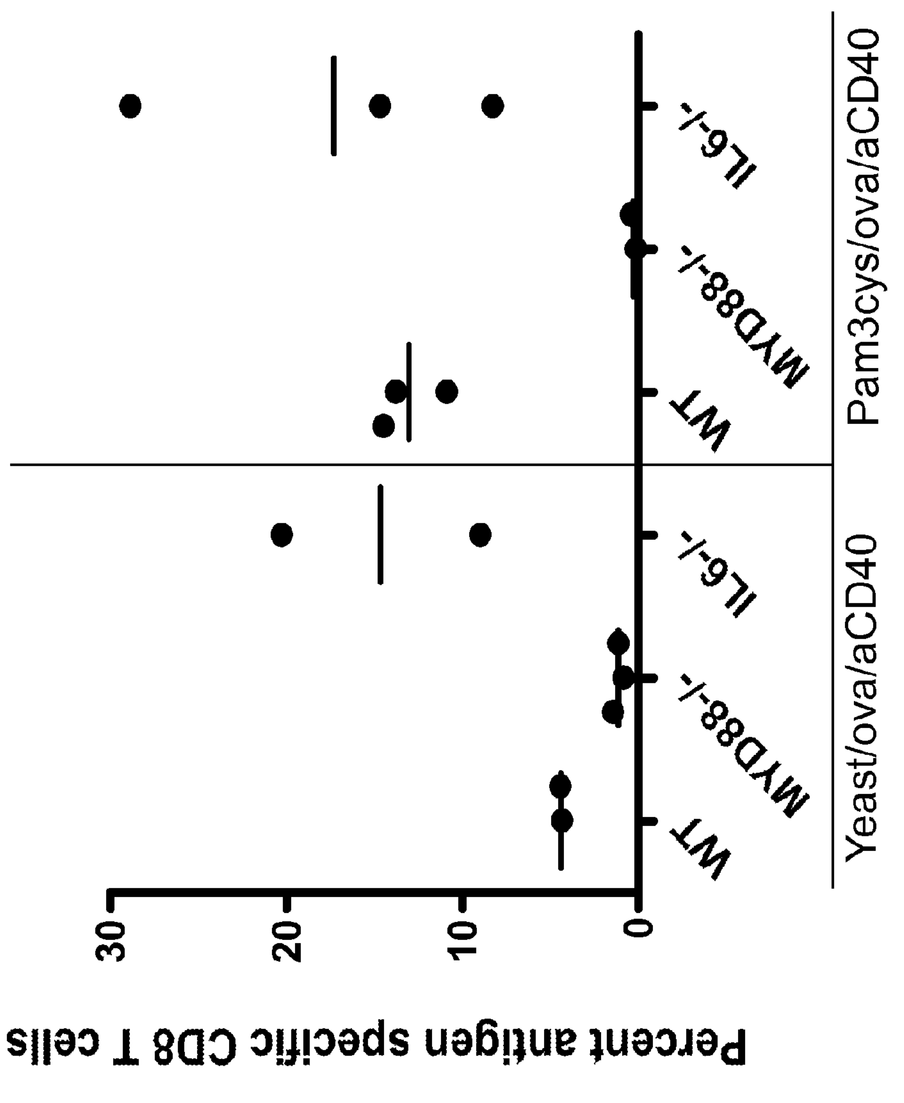
FIG. 11 is a graph showing the actual percentage of CD8 T cells in the population from mice immunized with yeast-based immunotherapy in FIGS. 3A-3C that are antigen-specific for ovalbumin.

FIG. 11 quantifies the actual percentage of the CD8 T cells in the population from mice immunized with yeast-based immunotherapy (Yeast/ova/aCD40) that are antigen-specific for ovalbumin presented in FIGS. 10A-10C, by gating on CD8 T cells prior to assessing antigen-specific markers. Similar data generated using mice immunized with pam3cys in combination with ovalbumin and anti-CD40 are also shown for comparison to yeast-based immunization (Pam3cys/ova/aCD40). The data show that the antigen-specific T cells produced by the yeast-based immunotherapy, but not the pam3cys immunotherapy, are improved by removal of IL-6. The lack of improvement in CD8 T cell responses in the pam3cys system reflects the fact that this agent is not influenced by IL-6. Therefore the influence on yeast-based immunotherapy by IL-6 is not likely to be occurring via a TLR, since both yeast and pam3cys can engage TLRs.

Figure 12:
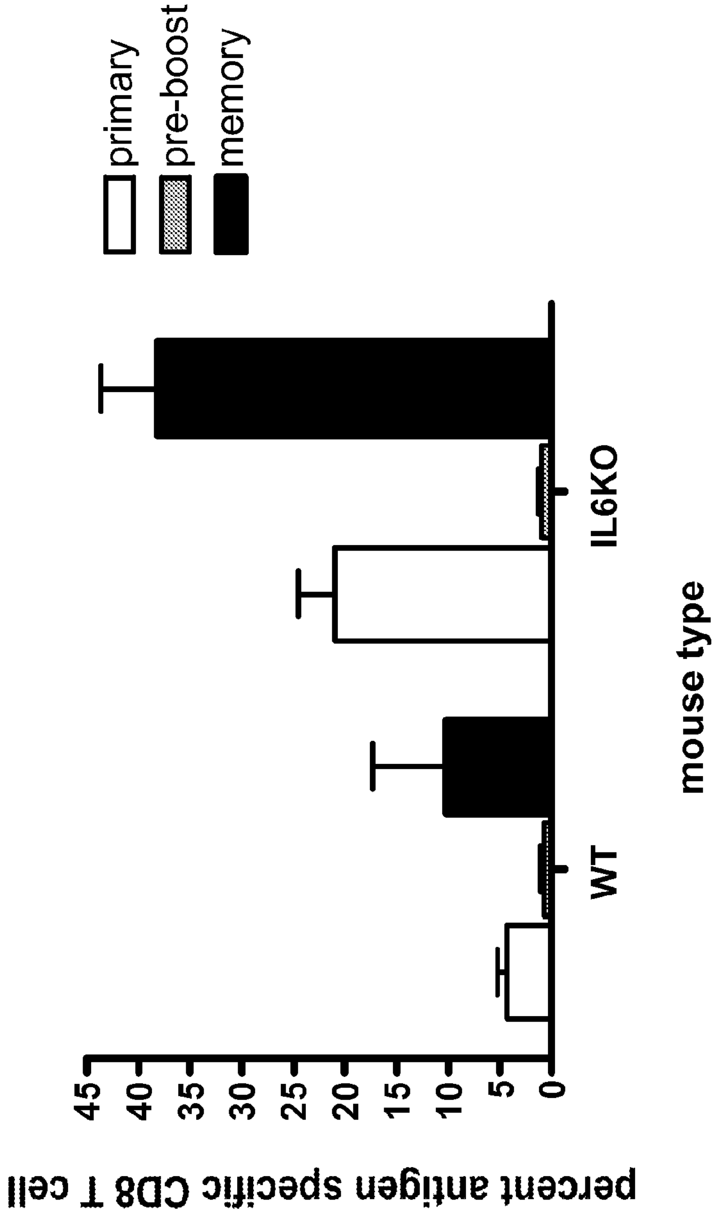
FIG. 12 is a bar graph showing the frequency of antigen-specific CD8 T cells following one immunization (primary, white bars) with yeast-based immunotherapy, and following an identical second immunization 60 days later (memory, black bars), in wild-type and IL-6 knockout mice.

FIG. 12 examines the frequency of antigen-specific CD8 T cells following not only one immunization (primary) but also following an identical second immunization 60 days later (memory). These are compared with an intermediate time point (pre-boost) where the number of antigen-specific T cells has returned to near undetectable levels.

The data show that the frequency of antigen specific T cells after a second immunization continues to improve in the IL-6 deficient mice, indicating that removal of IL-6 does not, within this time frame, appear to interfere with the long term development of immunity as a result of administration of a yeast-based immunotherapy composition.

The frequency of antigen-specific CD8+ T cells has reproducibly generated between 1 in 100 and 5 in 100 antigen-specific CD8+ cells following one dose of appropriately administered yeast-based immunotherapy in wild-type mice (e.g., see FIGS. 2A-2C). The frequency of antigen-specific CD8+ T cells following one dose of appropriately administered yeast-based immunotherapy increased to between about 1 in 3 to about 1 in 4 in an IL-6 knockout mouse, demonstrating that the inhibition of pathways associated with IL-6, which include TH17 development, can be utilized to enhance TH1-mediated and CD8+ immune responses.

Example 6

The following example demonstrates the correlation between yeast-based immunization and a reduction in regulatory T cells (Treg).

It is generally believed in the art that TH17 may outcompete Treg through the ability of TH17 to respond to lower concentrations of TGFβ, which may be further facilitated by IL-6 neutralizing Treg via FoxP3 signal uncoupling. Therefore, the inventors examined whether any correlation existed between the frequencies of TH17 and Treg in the context of yeast-based immunotherapy and whether this correlation, if present, was influenced by the presence or absence of IL-6.

Baseline CD4 Treg frequencies were measured and compared to the frequencies in IL-6 knockout and WT mice after whole yeast based immunization. The approach involved flow cytometric analyses of CD4+ T cells expressing the Treg transcription factor, FoxP3, that can be detected with commercially available antibodies.

Figure 13:
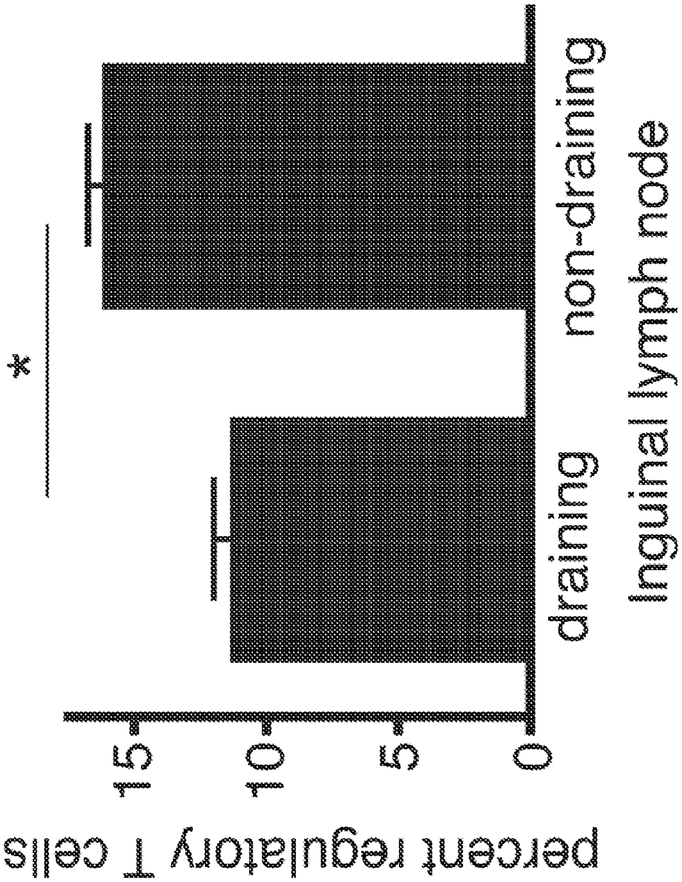
FIG. 13 is a bar graph showing the percentage of regulatory T cells (Treg) in the draining and non-draining lymph node of an IL-6 knockout mouse immunized with a yeast-based immunotherapy composition.

Following immunization, the data (FIG. 13) show a negative correlation in the levels of Treg as a function of immunization with yeast-based immunotherapy. IL-6 knockout mice had increased frequencies of Treg compared to WT mice as previously reported by Korn et al, 2007. However, the data here show that Treg frequencies were decreased in the draining lymph node of IL-6 knockout animals that were immunized with a yeast-based immunotherapeutic (FIG. 13). In wild-type mice, Treg generation was thwarted even when measured in the peripheral blood as a result of yeast-based immunotherapy (data not shown). This lack of Treg expansion in WT mice correlated with an increase in IL-17-producing T cells (data not shown). Expansion of Treg did occur when mice were immunized with pam3cys. Since pam3cys activation of T cells is unaffected by IL-6 depletion, these data support the interpretation that an IL-6 mediated induction of TH17 adversely impacts the ability of the animal to generate regulatory T cells (Treg). Thus, yeast-based induction of TH17 provides a means to negatively influence regulatory T cells that otherwise normally subvert persistent TH1 and CD8 T cell activation and expansion.

Taken together with the earlier examples, these data show that yeast induce IL-17 producing TH17 T cells, and this is associated with a diminution in regulatory T cell (Treg) generation. Without being bound by theory, the inventors believe that since both TH17 and TH1 are driven in common by TGFβ, TH17 T cells, because of their requirement for lower amounts of TGFβ, "outcompete" Treg for this essential growth factor. Accordingly, IL-6 may not be necessary to target Treg. This is supported by data generated from the IL-6 knockout in which the IL-6 knockout had reduced frequencies of Treg even though IL-6 is not present. In this scenario, it is possible, again without being bound by theory, that an IL-21-dependent alternative pathway can also induce TH17 as a result of yeast-based immunotherapy when IL-6 is not present or when IL-6 is limiting. If one assumed that the absence of IL-6 ultimately favors the induction of uncontrolled Treg, then antigen specific CD8+ responses might be expected to deteriorate with the frequency of immunization. However, in contradiction of this theory and in support of the concept that yeast-based immunization induces TH17 through more than one pathway, in the studies of repetitive immunization described in Example 5, yeast-based immunization leads to persisting immune responses over time, even in the IL-6 knockout mouse.

Having observed an inverse correlation between Treg and TH17 generation following primary whole yeast based immunization (see Examples 3 and 6), even in an environment devoid of IL-6, and given the role for Treg in downregulating TH1 responses, the long term consequences of repeated immunization by yeast-based immunotherapy or pam2cys immunotherapy are examined.

Whole yeast-based immunization induces CD8 populations that expand and persist at secondary (see FIG. 12) immunizations, and that are expected to continue to expand and persist at tertiary immunizations. IL-17 producing CD4 T cells are expected to expand after each yeast-based immunotherapy immunization. Treg frequencies are expected to be inversely correlated with TH17 frequencies. It is also expected that there will be an inverse correlation between the frequency of Treg observed following the TH17-associated yeast-based immunization and the frequency of antigen-specific CD8 generation following repeated immunization.

TH17 thrive in what appears to be a potentially self-perpetuating environment that influences other T cell subset development. However, the pro-inflammatory environment that supports TH17 development also signals anti-inflammatory counter measures, such as the production of Type I interferons that enhance cross presentation of antigen to the Class I pathway and subsequent CD8 T cell generation. Indeed, costimulation via CD28 can augment interferon-γ and IL-2 production that both impairs TH17 cells and promotes the Th1 pathway. In addition, IL-17-mediated recruitment of neutrophils can clear the pathogen and reduce the production of IL-6 which is important to drive TH17.

Accordingly, and without being bound by theory, the inventors believe that in certain individuals and certain disease states, there is value in generating concomitantly a TH17 and TH1 response, such as that induced by yeast-based immunotherapy, wherein the TH17 may ultimately improve TH1 responses by targeting Treg as well as produce cytokines such as IL-21 that promote durable memory CD8 responses. Alternatively, by modulating the responses generated by yeast-based immunotherapy, a "personalized" approach or a "disease-specific" approach is now possible based on the teachings described herein, since the inventors have shown that by modulating the TH17/TH1 pathways targeted by yeast, one can upregulate or downregulate TH17, TH1, Treg and/or CD8+ antigen-specific T cells responses. In summary, the yeast-based immunotherapy approach provides a plethora of opportunities for complex interactions which can now be tailored to better treat a particular individual or a particular infection or other disease state.

Example 7

The following example demonstrates the relationship between CD4-dependence (TH1, TH17) and interferon-independence of the yeast-based immune response.

It is known that type I interferons can inhibit the CD4-dependent pathway (Guo et al, 2008; Moschen et al, 2008; Alexander et al, 2010; Aristimuno et al, 2010; Axtell et al, 2010). The inventors therefore sought to determine whether a yeast-induced CD4-dependent pathway can function in an interferon-independent fashion.

Figure 14:
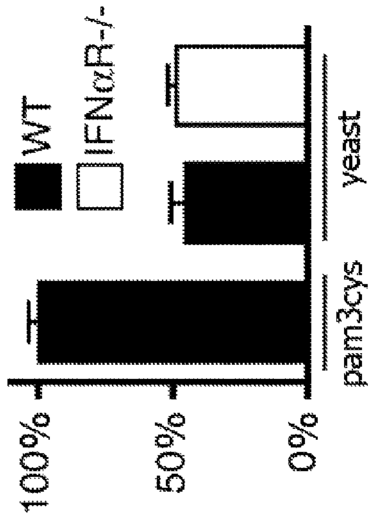
FIG. 14 is a bar graph showing the percentage of CD8+ T cells generated in wild-type (WT, black bars) and type I interferon receptor knockout mice (IFNαR−/−, white bar) in mice immunized with pam3cys plus ovalbumin plus anti-CD40 (pam3cys, control set at 100% shown in WT only) and in mice immunized with yeast plus ovalbumin plus anti-CD40 (yeast).

Mice engineered to be defective in the expression of the type I interferon receptor (IFNαR−/−) were immunized as described in Example 2 and compared to mice immunized with pam3cys as described in the experiment shown in FIG. 5. The data, shown in FIG. 14, are represented as the percentage of the tetramer positive cells generated in WT mice with pam3cys where that value is 100%. The results show the reproducible reduction in the generation of CD8 T cells when comparing yeast to pam3cys (column 1 vs 2) with no change in the outcome in mice lacking receptivity to type I interferon (column 3). Accordingly, wherein generating CD8 T cells with yeast-based immunotherapy in type I interferon receptor knockout mice does not significantly influence the frequency of CD8 T cells generated. These results indicate that yeast-based immunotherapy can trigger CD8 responses independent of type I IFN treatment and this occurs in the presence of and dependence on CD4 T cells. Thus, yeast-based immunotherapy is demonstrably a CD4-dependent, type I interferon-independent process. Evidence for a CD4-independent pathway resulting from yeast-based immunotherapy was provided in Example 2 (FIG. 5), although it is unclear whether one pathway dominates in a significant manner in a wild-type (CD4-"normal") environment, with the caveat that "wild-type human" subjects are genetically heterogeneous.

Example 8

In this example, the direct anti-tumor activity of TH17 and the contributions of IL-6 and anti-CD40 are evaluated.

TH17 cells and IL-17 have very recently been associated with anti-tumor activity. IL-17 may have direct anti-tumoricidal activity and IL-17 recruits anti-tumoricidal neutrophils. Thus the inventors believe that yeast-based immunotherapeutics could be intrinsically anti-tumoricidal through their ability as fungi to induce TH17. TH17 may also indirectly have anti-tumor activity by interfering with Treg development. These anti-tumor properties appear to be enhanced on concomitant treatment with anti-CD40 antibody. While anti-CD40 antibody treatment in and of itself has not been reported to produce substantive anti-tumoricidal effects CD40 engagement is anti-tumoricidal, for example, in the presence of exogenous sources of IL-15 or in combination with TLR agonists.

Yeast-based immunotherapy immunization combined with anti-CD40 antibody generates specific and non specific anti-tumor in vivo CTL activity. The inventors believe that yeast-based compositions induce TH17 with non-specific cytokine- and chemokine-associated, anti-tumoricidal properties and TH1 with specific tumoricidal potential via CD8 activation and expansion. The necessity for CD40 engagement is unclear but likely influential in focusing APC activity. The following experiment measures CTL activity induced via yeast-based immunotherapy and assesses how tumoricidal specificity is influenced by the presence of IL-6 and or anti-CD40.

Antigen-specific, in vivo CTL experiments are performed with YVEC (empty vector yeast) immunized animals as well as OVAX immunized animals. The YVEC immunized animals are immunized with and without ovalbumin. The contribution of anti-CD40 antibody is also assessed by performing immunizations with and without this reagent. WT and IL-6 KO immunized mice are compared. Briefly, immunized mice are evaluated to determine whether they generate antigen-specific CD8+ CTL responses against target tumor cells that express the antigen (ovalbumin in this case).

Example 9

The following example describes the use of other immunomodulatory agents to enhance TH1-mediated and/or CD8+ T cell responses.

Animals (WT and IL-6 knockout mice) are immunized with a yeast-based immunotherapeutic, such as yeast combined with ovalbumin or OVAX, with or without anti-CD40, and with and without an immunomodulator that downregulates TH17 responses, downregulates Treg and/or upregulates TH1 immune responses. It is expected that administration of the immunomodulator will enhance TH1 and CD8 T cell responses in the wild-type animals, and may also enhance TH1 and CD8 T cell responses in the IL-6 KO animals.

Example 10

The following example describes the use of yeast produced using a method that downregulates TH17 immune responses, and/or upregulates TH1 immune responses.

Animals (WT and IL-6 knockout mice) are immunized with a yeast-based immunotherapeutic, such as yeast combined with ovalbumin or OVAX, with or without anti-CD40, wherein the yeast have been produced under conditions that down-regulate TH17 responses and/or upregulate TH1 immune responses, as compared to yeast produced without such conditions. It is expected that administration of the yeast produced under conditions that enhance TH1 immune responses will enhance TH1 and CD8 T cell responses in the wild-type animals, and may also enhance TH1 and CD8 T cell responses in the IL-6 KO animals.

Example 11

The following example describes the use of immunomodulatory agents to enhance TH1-mediated and/or CD8+ T cell responses in a subject that has cancer.

Subjects with cancer are immunized with a yeast-based immunotherapeutic, such as yeast expressing one or more cancer antigens (e.g., cancer antigens that are expressed by the subject's cancer) and/or immunogenic domains thereof, and with an agent that downregulates TH17 responses, downregulates Treg and/or upregulates TH1 immune responses. The subject can also receive one or more therapeutic treatments that are useful for the treatment of the cancer, such as chemotherapy, radiation, and/or surgical removal of a tumor. The yeast-based immunotherapeutic can be administered intermittently with the agent and/or therapeutic treatment, and may also be administered before or after the regimen of therapeutic treatment and or the agent.

Such an agent can be selected from, but is not limited to, any one or more of anti-IL-1 or an IL-1 antagonist, anti-IL-6 or an IL-6 antagonist, anti-IL-17 or an IL-17 antagonist, anti-IL-21 or an IL-21 antagonist, anti-IL-22 or an IL-22 antagonist, anti-IL-23 or an IL-23 antagonist, IL-25 or an agonist thereof, IL-27 or an agonist thereof, an agent that blocks FOXP3, a Toll-like receptor (TLR) agonists, including but not limited to TLR-2 agonists, TLR-4 agonists, TLR-7 agonists, and TLR-9 agonists; an anti-inflammatory agent, an immunomodulatory agent, and/or another immunotherapeutic vaccine.

It is expected that administration of the combination of yeast-based immunotherapeutic and the agent will enhance TH1 and CD8 T cell responses in the subject, thereby ameliorating one or more symptoms of the cancer, e.g., reduce tumor growth, reduce tumor burden, and/or increase survival of the subject.

Example 12

The following example describes the use of immunomodulatory agents to enhance TH1-mediated and/or CD8+ T cell responses in a subject that has a viral-associated disease, such as hepatitis.

Subjects with hepatitis are immunized with a yeast-based immunotherapeutic, such as yeast expressing one or more hepatitis virus antigens and/or immunogenic domains thereof, and with an agent that downregulates TH17 responses, down-regulates Treg and/or upregulates TH1 immune responses. The subject can also receive one or more therapeutic treatments that are useful for the treatment of hepatitis, such as interferon therapy and/or anti-viral therapy. The yeast-based immunotherapeutic can be administered intermittently with the agent and/or therapeutic treatment, and may also be administered before or after the regimen of therapeutic treatment and or the agent.

Such an agent can be selected from, but is not limited to, any one or more of anti-IL-1 or an IL-1 antagonist, anti-IL-6 or an IL-6 antagonist, anti-IL-17 or an IL-17 antagonist, anti-IL-21 or an IL-21 antagonist, anti-IL-22 or an IL-22 antagonist, anti-IL-23 or an IL-23 antagonist, IL-25 or an agonist thereof, IL-27 or an agonist thereof, an agent that blocks FOXP3, a Toll-like receptor (TLR) agonists, including but not limited to TLR-2 agonists, TLR-4 agonists, TLR-7 agonists, and TLR-9 agonists; an anti-inflammatory agent, an immunomodulatory agent, and/or another immunotherapeutic vaccine.

It is expected that administration of the combination of yeast-based immunotherapeutic and the agent will enhance TH1 and CD8 T cell responses in the subject, thereby ameliorating one or more symptoms of the hepatitis, e.g., reduce viral load and/or improve liver function in the subject.

Example 13

The following example describes the use of yeast produced using a method that downregulates TH17 immune responses, and/or upregulates TH1 immune responses.

Subjects with cancer are immunized with a yeast-based immunotherapeutic, such as yeast expressing one or more cancer antigens (e.g., cancer antigens that are expressed by the subject's cancer) and/or immunogenic domains thereof. The yeast have been produced under conditions that down-regulate TH17 responses and/or upregulate TH1 immune responses, as compared to yeast produced without such conditions. The subject can also receive one or more therapeutic treatments that are useful for the treatment of the cancer, such as chemotherapy, radiation, and/or surgical removal of a tumor. The yeast-based immunotherapeutic can be administered intermittently with an agent and/or therapeutic treatment, and may also be administered before or after the regimen of therapeutic treatment and or an agent.

It is expected that administration of the modified yeast-based immunotherapeutic will enhance TH1 and CD8 T cell responses in the subject, thereby ameliorating one or more symptoms of the cancer, e.g., reduce tumor growth, reduce tumor burden, and/or increase survival of the subject.

Example 14

The following example describes the use of yeast produced using a method that downregulates TH17 immune responses, and/or upregulates TH1 immune responses in a subject that has a viral-associated disease, such as hepatitis.

Subjects with hepatitis are immunized with a yeast-based immunotherapeutic, such as yeast expressing one or more hepatitis virus antigens and/or immunogenic domains thereof. The yeast have been produced under conditions that downregulate TH17 responses and/or upregulate TH1 immune responses, as compared to yeast produced without such conditions. The subject can also receive one or more therapeutic treatments that are useful for the treatment of hepatitis, such as interferon therapy and/or anti-viral therapy. The yeast-based immunotherapeutic can be administered intermittently with the agent and/or therapeutic treatment, and may also be administered before or after the regimen of therapeutic treatment and or the agent.

It is expected that administration of the combination of the modified yeast-based immunotherapeutic will enhance TH1 and CD8 T cell responses in the subject, thereby ameliorating one or more symptoms of the hepatitis, e.g., reduce viral load and/or improve liver function in the subject.

Example 15

The following example describes the use of immunomodulatory agents to enhance TH17 T cell responses in a subject that has a fungal disease.

Subjects with a fungal disease, such as a disease caused by *Aspergillus* infection, fungal disease caused by *Coccidioides immitis*, or *Cryptococcosis*-associated conditions, are immunized with a yeast-based immunotherapeutic, such as yeast expressing one or more fungal antigens and/or immunogenic domains thereof, and with an agent that upregulates TH17 responses. The subject can also receive one or more therapeutic treatments that are useful for the treatment of the fungal disease. The yeast-based immunotherapeutic can be administered intermittently with the agent and/or therapeutic treatment, and may also be administered before or after the regimen of therapeutic treatment and or the agent.

Such an agent can be selected from, but is not limited to, any one or more of IL-1 or an agonist thereof, IL-6 or an agonist thereof, IL-17 or an agonist thereof, IL-21 or an agonist thereof, IL-22 or an agonist thereof, IL-23 or an agonist thereof, anti-IL-25 or IL-25 antagonist, anti-IL-27 or an IL-27 antagonist, a Toll-like receptor (TLR) antagonist, a pro-inflammatory agent, or a bacterial or fungal component, which may include additional yeast.

After the initial anti-fungal immune response is observed by alleviation of one or more symptoms of the disease, or after about 1-5 doses of yeast-based immunotherapy in conjunction with the agent, the agent is omitted from additional therapy, in order to allow a TH1 type response to occur in the individual.

It is expected that administration of the combination of yeast-based immunotherapeutic and the agent will enhance TH17 T cell responses in the subject, thereby ameliorating one or more symptoms of the fungal disease, e.g., reduce fungal burden and/or increase survival of the subject.

Example 16

The following example demonstrates the measurement of proliferation of peripheral blood lymphocytes in response to yeast-based immunotherapy.

In this example, data from one human subject in a Phase I mutated ras cancer clinical trial (GlobeImmune, Inc.) are shown. In this experiment, the ability of a subject's peripheral blood lymphocytes (PBLs) to proliferate in response to various stimuli was evaluated. Briefly, PBLs were evaluated for proliferation to PHA, *Candida* extracts, and two different concentrations of a yeast-based immunotherapy composition (heat-killed *Saccharomyces cerevisiae* expressing a recombinant mutated ras antigen, denoted "4016") by measuring thymidine incorporation 5 days after culture initiation for yeast-based immunotherapy composition or *Candida* extracts, and 3 days for PHA. It is expected that PBLs from most individuals will respond to PHA and also to *Candida* yeast extracts. These data clearly show that the PBLs from this patient do not proliferate to a yeast-based immunotherapeutic in vitro but strongly proliferate upon exposure to PHA and *Candida* extracts.

TABLE 1

| | Well 1 | Well 2 | Well 3 | Mean | SD | SI[1] | SI Error |
|---|---|---|---|---|---|---|---|
| Unstimulated-Day 3 | 183 | 123 | 85 | 130.3 | 49.4 | 1.00 | 0.54 |
| Unstimulated-Day 6 | 263 | 188 | 124 | 191.7 | 69.6 | 1.00 | 0.51 |
| PHA | 58271 | 69995 | 55102 | 61122.7 | 7845.3 | 468.97 | 187.70 |
| Candida | 23515 | 21853 | 19908 | 21758.7 | 1805.3 | 113.52 | 42.27 |
| 4016 1:2 | 664 | 105 | 329 | 366.0 | 281.3 | 1.91 | 1.62 |
| 4016 1:20 | 234 | 456 | 218 | 302.7 | 133.0 | 1.58 | 0.90 |

[1]SI = stimulation index of antigen versus unstimulated control

In the next example (Table 2) the experiment was repeated with PBLs from the same subject one week after the subject was immunized (in vivo) with the yeast-based immunotherapy composition (4016). It is clear that the patient's response to yeast-based immunotherapy has developed as a consequence of immunization.

TABLE 2

| | Well 1 | Well 2 | Well 3 | Mean | SD | SI | SI Error |
|---|---|---|---|---|---|---|---|
| Unstimulated-Day 3 | 71 | 105 | 88 | 88.0 | 17.0 | 1.00 | 0.27 |
| Unstimulated-Day 6 | 224 | 133 | 241 | 199.3 | 58.1 | 1.00 | 0.41 |
| PHA | 105678 | 125217 | 84292 | 105062.3 | 20469.4 | 1193.89 | 327.57 |
| Candida | 33391 | 52816 | 30749 | 38985.3 | 12050.3 | 195.58 | 83.07 |

TABLE 2-continued

| | Well 1 | Well 2 | Well 3 | Mean | SD | SI | SI Error |
|---|---|---|---|---|---|---|---|
| 4016 1:2 | 14869 | 7401 | 12493 | 11587.7 | 3815.4 | 58.13 | 25.56 |
| 4016 1:20 | 1996 | 5111 | 1748 | 2951.7 | 1874.1 | 14.81 | 10.34 |

The “non-responder” phenotype detailed in Table 1 that becomes a responder following immunization with the yeast-based immunotherapy is observed in approximately 25% of subjects tested from various clinical trials (data not shown). A second phenotype, representing 50% of the population, is characterized by subjects whose PBLs respond to yeast-based immunotherapy compositions in vitro before immunization and who remain responders after immunization. The final 25% of subjects are non-responders by proliferation to yeast-based immunotherapy compositions in vitro prior to immunization and their T cells continue to fail to proliferate in response to yeast-based immunotherapy compositions in vitro even after immunization with the composition. It is noted that “non-responder” is used in the context of proliferation of PBLs in response to exposure to a yeast-based immunotherapeutic in vitro, but is not necessarily an indicator that the subject is “non-responsive” to yeast-based immunotherapy as a therapeutic. Indeed, without being bound by theory, the present inventors believe that these “non-proliferators” are actually likely to be hyper-TH17 responders (individuals who produce strong, high or very high TH17 responses), where the TH17 microenvironment may actually be anti-proliferative rather than truly non-responsive. In other words, in these individuals, exposure to yeast-based compositions in vitro (and also in vivo) is most likely activating TH17 cells, but not TH1 cells (or is overcommitted to the TH17 pathway at the expense of the TH1 pathway), whereas the proliferation assay measures TH1-type CD4+ responses that are known to be proliferative in nature. Such subjects may be particularly good candidates for administration of yeast-based immunotherapy in conjunction with an agent that inhibits the TH17 response, when a TH1-mediated CD8 immune response is deemed to be beneficial (e.g., in the context of eliciting a therapeutic immune response against a virus, a tumor and/or an intracellular pathogen or other pathogen).

Example 17

The following example demonstrates methods of screening subjects for predicted immune response to yeast-based immunotherapy.

Peripheral blood mononuclear cell samples and serum are collected from an individual to be screened. Serum samples are evaluated to determine levels of IL-17 and/or IL-23 versus IL-12, where IL-17 and IL-23 are considered to be TH17 cytokines and IL-12 a TH1 cytokine Serum collected from clotted blood and frozen at −80° C. until use will be tested with a commercially available ELISA kit, such as that from Human Quantikine R&D Systems where the lower limits of detection for IL-12, IL-23 and IL-17 are 15.0, 6.8 and 15.0 pg/ml, respectively. The subject will be evaluated to determine whether the TH17 and TH1 levels in the subject differ from that expected in the normal population, and to determine whether the subject can be broadly classified as a high (stronger) or lower (weak) IL-17 producer, or as a “normal” IL-17 producer. Another category of “very high” IL-17 producers may be established, in which the subject produces very little or no IL-12 and appears to have a nearly exclusive TH17 response in response to stimuli. In the event that the serum profiles do not provide a clear demarcation of high/strong versus low/weak for IL-17 or IL-12, then IL-23 values are expected to resolve the analysis. IL-23 shares the heavy chain with IL-12, is produced by DCs and correlates with TH17 durability (reviewed by Korn et al, 2009).

It is expected that subjects with the highest (strong) IL-17 activity in response to yeast-based immunotherapy will have an immune response skewed towards the IFN-independent, CD4- and IL-12-dependent pathway. Conversely, those with a lower (weak) or more balanced TH17 activity will have a less dominant TH17/TH1 response and be more skewed towards an IFN-dependent, and CD4- and IL-12-independent pathway.

In another experiment, peripheral blood mononuclear cells collected from blood draws are phenotyped by flow cytometric intracellular cytokine staining for relative percentages of CD3+CD4+ cells, and for CD3+CD8+ cells that are producers of IFN-γ or IL-17, each defined via intracellular staining following a short pulse with ionomycin as described by Chen et al, 2010. CD8 IFN-γ ELISpots are also performed. The frequency and phenotype of T cells that produce IL-17 or the IL-12 associated T cell cytokine IFN-γ, are evaluated, as is the frequency of IFN-γ-producing CD8+ T cells. A correlation is developed between IL-17 and TH17 cells and IL-12 and IFN-γ-producing CD4 T cells.

In another experiment, frequencies of Treg cells are evaluated as a function of yeast-based immunization since TH17 and Treg are expected to be inversely correlated. Cells from patients are phenotyped for CD25+FoxP3+CD4+ T cells as markers for Treg.

In another experiment, patient peripheral blood lymphocytes are evaluated for their ability to proliferate in response to yeast in vitro as a consequence of immunization. It is expected that subjects will be separated into at least three populations as described in Example 16: (1) those whose lymphocytes always proliferate to yeast in vitro, regardless of whether they previously received yeast-based immunotherapy or not, (2) those that proliferate in response to yeast in vitro only as a result of receiving yeast-based immunotherapy prior to the assay, and (3) those that never proliferate to yeast in vitro regardless of their treatment. Without being bound by theory, it is expected that the latter population will include a TH17 hyper-responsive population (high/strong and/or very high/very strong TH17 responders), because the TH17 transcription factor RORγt may lead to TH17 associated anti-proliferative signaling.

In these assays, peripheral blood mononuclear cells (denoted PBL or PBMC) are isolated from peripheral blood and cultured at 300,000 and 150,000 cells per well (on average containing about 30% CD3+ T cells) with heat-killed yeast at a ratio of 10:1 or 1:1 yeast per PBL. Two positive controls can include *Candida* yeast extracts and the T cell mitogen, phytohemagglutinin (PHA), to which most individuals' PBLs should respond (see tables in Example 16).

As in Example 16 above, establishing the level of TH17-type responsiveness and TH1-type responsiveness (or the ratio of the two responses) in an individual can be used to determine how best to treat the individual using yeast-based immunotherapy, given the disease to be prevented or treated, the type of immune response that is predicted to be the most efficacious for that disease, and the type of immune response that the individual is predicted to produce in response to yeast-based immunotherapy without other intervention. Accordingly, the treatment protocol can be modified to ensure that the most advantageous, beneficial, and/or therapeutic response is elicited for the specific individual and the specific disease or condition, improving the outcome of yeast-based immunotherapy.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to inhibit the production or survival of CD4+ TH17 cells in a subject, comprising administering to a subject:

a) a yeast-based immunotherapy composition comprising a whole yeast and an antigen; and b) an agent that inhibits the production or survival of CD4+ TH17 cells, wherein the agent inhibits interleukin-6 (IL 6), and wherein the agent is selected from an antibody or antigen binding portion thereof, or a soluble inactive form of IL-6 or its receptor;

wherein the administration of the agent is prior to, in conjunction with, and/or following administration of the yeast-based immunotherapy composition, and wherein the production or survival of CD4+ TH17 cells is inhibited in the subject.

2. The method of claim 1, wherein the subject, as a result of administration of the yeast-based immunotherapy composition in the absence of the agent, produces statistically significantly (p>0.05) more IL-17 and/or has more TH17 CD4+ T cells than the average level of IL-17 production or average number of TH17 cells in CD4+ T cells isolated from the same source from a population of individuals who are generally healthy or, as a group, are not experiencing a particular disease or condition.

3. The method of claim 1, wherein T cells that have been isolated from the subject do not proliferate or proliferate weakly in response to contact with a yeast-based immunotherapy composition.

4. The method of claim 1, wherein T cells that have been isolated from the subject have greater than normal retinoid-related orphan receptor (ROR)-γexpression and/or have greater than normal levels of IL-17 production.

5. The method of claim 1, wherein the yeast-based immunotherapy composition is administered in one or more doses over a period of time prior to commencing the administration of the agent.

6. The method of claim 1, wherein the agent is administered for a period of time sufficient to induce an initial immune response in the subject, followed by a period of time wherein the yeast-based immunotherapy composition is administered in the absence of the agent.

7. The method of claim 1, wherein the whole yeast is a heat-inactivated whole yeast.

8. The method of claim 1, wherein the whole yeast is from *Saccharomyces.*

9. The method of claim 1, wherein the whole yeast is from *Saccharomyces cerevisiae.*

10. The method of claim 1, wherein the agent is anti-IL-6.

11. A composition comprising:

a) a yeast-based immunotherapy composition comprising a whole yeast and an antigen; and b) an agent that inhibits the production or survival of CD4+ TH17 cells, wherein the agent inhibits interleukin-6 (IL 6), and wherein the agent is selected from an antibody or antigen binding portion thereof, or a soluble inactive form of IL-6 or its receptor.

12. The composition of claim 11, wherein the agent is anti-IL-6.

* * * * *

```
                              SEQUENCE LISTING


<160> NUMBER OF SEQ ID NOS: 26

<210> SEQ ID NO 1
<211> LENGTH: 6
<212> TYPE: PRT
<213> ORGANISM: Artificial
<220> FEATURE:
<223> OTHER INFORMATION: synthetic peptide

<400> SEQUENCE: 1

Met Ala Asp Glu Ala Pro
1               5


<210> SEQ ID NO 2
<211> LENGTH: 1859
<212> TYPE: DNA
<213> ORGANISM: Homo sapiens
<220> FEATURE:
<221> NAME/KEY: CDS
<222> LOCATION: (46)..(513)

<400> SEQUENCE: 2

gcaggcacaa actcatccat ccccagttga ttggaagaaa caacg atg act cct ggg      57
                                                  Met Thr Pro Gly
                                                  1

aag acc tca ttg gtg tca ctg cta ctg ctg ctg agc ctg gag gcc ata      105
Lys Thr Ser Leu Val Ser Leu Leu Leu Leu Leu Ser Leu Glu Ala Ile
5                   10                  15                  20

gtg aag gca gga atc aca atc cca cga aat cca gga tgc cca aat tct      153
Val Lys Ala Gly Ile Thr Ile Pro Arg Asn Pro Gly Cys Pro Asn Ser
                25                  30                  35

gag gac aag aac ttc ccc cgg act gtg atg gtc aac ctg aac atc cat      201
Glu Asp Lys Asn Phe Pro Arg Thr Val Met Val Asn Leu Asn Ile His
            40                  45                  50

aac cgg aat acc aat acc aat ccc aaa agg tcc tca gat tac tac aac      249
Asn Arg Asn Thr Asn Thr Asn Pro Lys Arg Ser Ser Asp Tyr Tyr Asn
        55                  60                  65

cga tcc acc tca cct tgg aat ctc cac cgc aat gag gac cct gag aga      297
Arg Ser Thr Ser Pro Trp Asn Leu His Arg Asn Glu Asp Pro Glu Arg
    70                  75                  80

tat ccc tct gtg atc tgg gag gca aag tgc cgc cac ttg ggc tgc atc      345
Tyr Pro Ser Val Ile Trp Glu Ala Lys Cys Arg His Leu Gly Cys Ile
85                  90                  95                  100

aac gct gat ggg aac gtg gac tac cac atg aac tct gtc ccc atc cag      393
Asn Ala Asp Gly Asn Val Asp Tyr His Met Asn Ser Val Pro Ile Gln
                105                 110                 115

caa gag atc ctg gtc ctg cgc agg gag cct cca cac tgc ccc aac tcc      441
Gln Glu Ile Leu Val Leu Arg Arg Glu Pro Pro His Cys Pro Asn Ser
            120                 125                 130

ttc cgg ctg gag aag ata ctg gtg tcc gtg ggc tgc acc tgt gtc acc      489
Phe Arg Leu Glu Lys Ile Leu Val Ser Val Gly Cys Thr Cys Val Thr
        135                 140                 145
```

```
ccg att gtc cac cat gtg gcc taa gagctctggg gagcccacac tccccaaagc     543
Pro Ile Val His His Val Ala
    150                 155

agttagacta tggagagccg acccagcccc tcaggaaccc tcatccttca aagacagcct    603

catttcggac taaactcatt agagttctta aggcagtttg tccaattaaa gcttcagagg    663

taacacttgg ccaagatatg agatctgaat tacctttccc tctttccaag aaggaaggtt    723

tgactgagta ccaatttgct tcttgtttac ttttttaagg gctttaagtt atttatgtat    783

ttaatatgcc ctgagataac tttggggtat aagattccat tttaatgaat tacctacttt    843

attttgtttg tctttttaaa gaagataaga ttctgggctt gggaatttta ttatttaaaa    903

ggtaaaacct gtatttattt gagctattta aggatctatt tatgtttaag tatttagaaa    963

aaggtgaaaa agcactatta tcagttctgc ctaggtaaat gtaagataga attaaatggc   1023

agtgcaaaat ttctgagtct ttacaacata cggatatagt atttcctcct ctttgttttt   1083

aaaagttata acatggctga aaagaaagat taaacctact ttcatatgta ttaatttaaa   1143

ttttgcaatt tgttgaggtt ttacaagaga tacagcaagt ctaactctct gttccattaa   1203

acccttataa taaaatcctt ctgtaataat aaagtttcaa aagaaaatgt ttatttgttc   1263

tcattaaatg tattttagca aactcagctc ttccctattg ggaagagtta tgcaaattct   1323

cctataagca aaacaaagca tgtctttgag taacaatgac ctggaaatac ccaaaattcc   1383

aagttctcga tttcacatgc cttcaagact gaacaccgac taaggttttc atactattag   1443

ccaatgctgt agacagaagc attttgatag gaatagagca aataagataa tggccctgag   1503

gaatggcatg tcattattaa agatcatatg ggaaaatga aaccctcccc aaaatacaag    1563

aagttctggg aggagacatt gtcttcagac tacaatgtcc agtttctccc ctagactcag   1623

gcttcctttg gagattaagg cccctcagag atcaacagac caacattttt ctcttcctca   1683

agcaacactc ctagggcctg gcttctgtct gatcaaggca ccacacaacc cagaaaggag   1743

ctgatggggc agaacgaact ttaagtatga gaaaagttca gcccaagtaa aataaaaact   1803

caatcacatt caattccaga gtagtttcaa gtttcacatc gtaaccattt tcgccc       1859


<210> SEQ ID NO 3
<211> LENGTH: 155
<212> TYPE: PRT
<213> ORGANISM: Homo sapiens

<400> SEQUENCE: 3

Met Thr Pro Gly Lys Thr Ser Leu Val Ser Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
```

-continued

```
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155


<210> SEQ ID NO 4
<211> LENGTH: 808
<212> TYPE: DNA
<213> ORGANISM: Homo sapiens
<220> FEATURE:
<221> NAME/KEY: CDS
<222> LOCATION: (72)..(563)

<400> SEQUENCE: 4

gaacacaggc atacacagga agatacattc acagaaagag cttcctgcac aaagtaagcc      60

accagcgcaa c atg aca gtg aag acc ctg cat ggc cca gcc atg gtc aag      110
             Met Thr Val Lys Thr Leu His Gly Pro Ala Met Val Lys
             1               5                   10

tac ttg ctg ctg tcg ata ttg ggg ctt gcc ttt ctg agt gag gcg gca      158
Tyr Leu Leu Leu Ser Ile Leu Gly Leu Ala Phe Leu Ser Glu Ala Ala
    15                  20                  25

gct cgg aaa atc ccc aaa gta gga cat act ttt ttc caa aag cct gag      206
Ala Arg Lys Ile Pro Lys Val Gly His Thr Phe Phe Gln Lys Pro Glu
30                  35                  40                  45

agt tgc ccg cct gtg cca gga ggt agt atg aag ctt gac att ggc atc      254
Ser Cys Pro Pro Val Pro Gly Gly Ser Met Lys Leu Asp Ile Gly Ile
                50                  55                  60

atc aat gaa aac cag cgc gtt tcc atg tca cgt aac atc gag agc cgc      302
Ile Asn Glu Asn Gln Arg Val Ser Met Ser Arg Asn Ile Glu Ser Arg
            65                  70                  75

tcc acc tcc ccc tgg aat tac act gtc act tgg gac ccc aac cgg tac      350
Ser Thr Ser Pro Trp Asn Tyr Thr Val Thr Trp Asp Pro Asn Arg Tyr
        80                  85                  90

ccc tcg gaa gtt gta cag gcc cag tgt agg aac ttg ggc tgc atc aat      398
Pro Ser Glu Val Val Gln Ala Gln Cys Arg Asn Leu Gly Cys Ile Asn
    95                  100                 105

gct caa gga aag gaa gac atc tcc atg aat tcc gtt ccc atc cag caa      446
Ala Gln Gly Lys Glu Asp Ile Ser Met Asn Ser Val Pro Ile Gln Gln
110                 115                 120                 125

gag acc ctg gtc gtc cgg agg aag cac caa ggc tgc tct gtt tct ttc      494
Glu Thr Leu Val Val Arg Arg Lys His Gln Gly Cys Ser Val Ser Phe
                130                 135                 140

cag ttg gag aag gtg ctg gtg act gtt ggc tgc acc tgc gtc acc cct      542
Gln Leu Glu Lys Val Leu Val Thr Val Gly Cys Thr Cys Val Thr Pro
            145                 150                 155

gtc atc cac cat gtg cag taa gaggtgcata tccactcagc tgaagaagct         593
Val Ile His His Val Gln
        160

gtagaaatgc cactccttac ccagtgctct gcaacaagtc ctgtctgacc cccaattccc    653

tccacttcac aggactctta ataagacctg cacggatgga aacagaaaat attcacaatg    713

tatgtgtgta tgtactacac tttatatttg atatctaaaa tgttaggaga aaaattaata    773

tattcagtgc taatataata aagtattaat aattt                               808


<210> SEQ ID NO 5
<211> LENGTH: 163
<212> TYPE: PRT
<213> ORGANISM: Homo sapiens
```

<400> SEQUENCE: 5

```
Met Thr Val Lys Thr Leu His Gly Pro Ala Met Val Lys Tyr Leu Leu
1               5                   10                  15

Leu Ser Ile Leu Gly Leu Ala Phe Leu Ser Glu Ala Ala Ala Arg Lys
            20                  25                  30

Ile Pro Lys Val Gly His Thr Phe Phe Gln Lys Pro Glu Ser Cys Pro
        35                  40                  45

Pro Val Pro Gly Gly Ser Met Lys Leu Asp Ile Gly Ile Ile Asn Glu
    50                  55                  60

Asn Gln Arg Val Ser Met Ser Arg Asn Ile Glu Ser Arg Ser Thr Ser
65                  70                  75                  80

Pro Trp Asn Tyr Thr Val Thr Trp Asp Pro Asn Arg Tyr Pro Ser Glu
                85                  90                  95

Val Val Gln Ala Gln Cys Arg Asn Leu Gly Cys Ile Asn Ala Gln Gly
            100                 105                 110

Lys Glu Asp Ile Ser Met Asn Ser Val Pro Ile Gln Gln Glu Thr Leu
        115                 120                 125

Val Val Arg Arg Lys His Gln Gly Cys Ser Val Ser Phe Gln Leu Glu
    130                 135                 140

Lys Val Leu Val Thr Val Gly Cys Thr Cys Val Thr Pro Val Ile His
145                 150                 155                 160

His Val Gln
```

<210> SEQ ID NO 6
<211> LENGTH: 1201
<212> TYPE: DNA
<213> ORGANISM: Homo sapiens
<220> FEATURE:
<221> NAME/KEY: CDS
<222> LOCATION: (117)..(755)

<400> SEQUENCE: 6

```
aatattagag tctcaacccc caataaatat aggactggag atgtctgagg ctcattctgc      60

cctcgagccc accgggaacg aaagagaagc tctatctccc ctccaggagc ccagct atg     119
                                                              Met
                                                              1

aac tcc ttc tcc aca agc gcc ttc ggt cca gtt gcc ttc tcc ctg ggg       167
Asn Ser Phe Ser Thr Ser Ala Phe Gly Pro Val Ala Phe Ser Leu Gly
            5                   10                  15

ctg ctc ctg gtg ttg cct gct gcc ttc cct gcc cca gta ccc cca gga       215
Leu Leu Leu Val Leu Pro Ala Ala Phe Pro Ala Pro Val Pro Pro Gly
        20                  25                  30

gaa gat tcc aaa gat gta gcc gcc cca cac aga cag cca ctc acc tct       263
Glu Asp Ser Lys Asp Val Ala Ala Pro His Arg Gln Pro Leu Thr Ser
    35                  40                  45

tca gaa cga att gac aaa caa att cgg tac atc ctc gac ggc atc tca       311
Ser Glu Arg Ile Asp Lys Gln Ile Arg Tyr Ile Leu Asp Gly Ile Ser
50                  55                  60                  65

gcc ctg aga aag gag aca tgt aac aag agt aac atg tgt gaa agc agc       359
Ala Leu Arg Lys Glu Thr Cys Asn Lys Ser Asn Met Cys Glu Ser Ser
                70                  75                  80

aaa gag gca ctg gca gaa aac aac ctg aac ctt cca aag atg gct gaa       407
Lys Glu Ala Leu Ala Glu Asn Asn Leu Asn Leu Pro Lys Met Ala Glu
            85                  90                  95

aaa gat gga tgc ttc caa tct gga ttc aat gag gag act tgc ctg gtg       455
Lys Asp Gly Cys Phe Gln Ser Gly Phe Asn Glu Glu Thr Cys Leu Val
        100                 105                 110
```

-continued

```
aaa atc atc act ggt ctt ttg gag ttt gag gta tac cta gag tac ctc      503
Lys Ile Ile Thr Gly Leu Leu Glu Phe Glu Val Tyr Leu Glu Tyr Leu
    115                 120                 125

cag aac aga ttt gag agt agt gag gaa caa gcc aga gct gtg cag atg      551
Gln Asn Arg Phe Glu Ser Ser Glu Glu Gln Ala Arg Ala Val Gln Met
130                 135                 140                 145

agt aca aaa gtc ctg atc cag ttc ctg cag aaa aag gca aag aat cta      599
Ser Thr Lys Val Leu Ile Gln Phe Leu Gln Lys Lys Ala Lys Asn Leu
                150                 155                 160

gat gca ata acc acc cct gac cca acc aca aat gcc agc ctg ctg acg      647
Asp Ala Ile Thr Thr Pro Asp Pro Thr Thr Asn Ala Ser Leu Leu Thr
            165                 170                 175

aag ctg cag gca cag aac cag tgg ctg cag gac atg aca act cat ctc      695
Lys Leu Gln Ala Gln Asn Gln Trp Leu Gln Asp Met Thr Thr His Leu
        180                 185                 190

att ctg cgc agc ttt aag gag ttc ctg cag tcc agc ctg agg gct ctt      743
Ile Leu Arg Ser Phe Lys Glu Phe Leu Gln Ser Ser Leu Arg Ala Leu
    195                 200                 205

cgg caa atg tag catgggcacc tcagattgtt gttgttaatg ggcattcctt          795
Arg Gln Met
210

cttctggtca gaaacctgtc cactgggcac agaacttatg ttgttctcta tggagaacta    855

aaagtatgag cgttaggaca ctattttaat tatttttaat ttattaatat ttaaatatgt    915

gaagctgagt taatttatgt aagtcatatt tatattttta agaagtacca cttgaaacat    975

tttatgtatt agttttgaaa taataatgga aagtggctat gcagtttgaa tatcctttgt   1035

ttcagagcca gatcatttct tggaaagtgt aggcttacct caaataaatg gctaacttat   1095

acatattttt aaagaaatat ttatattgta tttatataat gtataaatgg tttttatacc   1155

aataaatggc attttaaaaa attcagcaaa aaaaaaaaaa aaaaaa                  1201


<210> SEQ ID NO 7
<211> LENGTH: 212
<212> TYPE: PRT
<213> ORGANISM: Homo sapiens

<400> SEQUENCE: 7

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160
```

```
Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210


<210> SEQ ID NO 8
<211> LENGTH: 616
<212> TYPE: DNA
<213> ORGANISM: Homo sapiens
<220> FEATURE:
<221> NAME/KEY: CDS
<222> LOCATION: (46)..(534)

<400> SEQUENCE: 8

ctgaagtgaa aacgagacca aggtctagct ctactgttgg tactt atg aga tcc agt      57
                                                  Met Arg Ser Ser
                                                  1

cct ggc aac atg gag agg att gtc atc tgt ctg atg gtc atc ttc ttg       105
Pro Gly Asn Met Glu Arg Ile Val Ile Cys Leu Met Val Ile Phe Leu
5                   10                  15                  20

ggg aca ctg gtc cac aaa tca agc tcc caa ggt caa gat cgc cac atg       153
Gly Thr Leu Val His Lys Ser Ser Ser Gln Gly Gln Asp Arg His Met
                25                  30                  35

att aga atg cgt caa ctt ata gat att gtt gat cag ctg aaa aat tat       201
Ile Arg Met Arg Gln Leu Ile Asp Ile Val Asp Gln Leu Lys Asn Tyr
            40                  45                  50

gtg aat gac ttg gtc cct gaa ttt ctg cca gct cca gaa gat gta gag       249
Val Asn Asp Leu Val Pro Glu Phe Leu Pro Ala Pro Glu Asp Val Glu
        55                  60                  65

aca aac tgt gag tgg tca gct ttt tcc tgc ttt cag aag gcc caa cta       297
Thr Asn Cys Glu Trp Ser Ala Phe Ser Cys Phe Gln Lys Ala Gln Leu
    70                  75                  80

aag tca gca aat aca gga aac aat gaa agg ata atc aat gta tca att       345
Lys Ser Ala Asn Thr Gly Asn Asn Glu Arg Ile Ile Asn Val Ser Ile
85                  90                  95                  100

aaa aag ctg aag agg aaa cca cct tcc aca aat gca ggg aga aga cag       393
Lys Lys Leu Lys Arg Lys Pro Pro Ser Thr Asn Ala Gly Arg Arg Gln
                105                 110                 115

aaa cac aga cta aca tgc cct tca tgt gat tct tat gag aaa aaa cca       441
Lys His Arg Leu Thr Cys Pro Ser Cys Asp Ser Tyr Glu Lys Lys Pro
            120                 125                 130

ccc aaa gaa ttc cta gaa aga ttc aaa tca ctt ctc caa aag atg att       489
Pro Lys Glu Phe Leu Glu Arg Phe Lys Ser Leu Leu Gln Lys Met Ile
        135                 140                 145

cat cag cat ctg tcc tct aga aca cac gga agt gaa gat tcc tga           534
His Gln His Leu Ser Ser Arg Thr His Gly Ser Glu Asp Ser
    150                 155                 160

ggatctaact tgcagttgga cactatgtta catactctaa tatagtagtg aaagtcattt     594

ctttgtattc caagtggagg ag                                              616


<210> SEQ ID NO 9
<211> LENGTH: 162
<212> TYPE: PRT
<213> ORGANISM: Homo sapiens

<400> SEQUENCE: 9
```

```
Met Arg Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser


<210> SEQ ID NO 10
<211> LENGTH: 1147
<212> TYPE: DNA
<213> ORGANISM: Homo sapiens
<220> FEATURE:
<221> NAME/KEY: CDS
<222> LOCATION: (54)..(593)

<400> SEQUENCE: 10

cgaccaggtt ctccttcccc agtcaccagt tgctcgagtt agaattgtct gca atg        56
                                                           Met
                                                           1

gcc gcc ctg cag aaa tct gtg agc tct ttc ctt atg ggg acc ctg gcc      104
Ala Ala Leu Gln Lys Ser Val Ser Ser Phe Leu Met Gly Thr Leu Ala
            5                   10                  15

acc agc tgc ctc ctt ctc ttg gcc ctc ttg gta cag gga gga gca gct      152
Thr Ser Cys Leu Leu Leu Leu Ala Leu Leu Val Gln Gly Gly Ala Ala
        20                  25                  30

gcg ccc atc agc tcc cac tgc agg ctt gac aag tcc aac ttc cag cag      200
Ala Pro Ile Ser Ser His Cys Arg Leu Asp Lys Ser Asn Phe Gln Gln
    35                  40                  45

ccc tat atc acc aac cgc acc ttc atg ctg gct aag gag gct agc ttg      248
Pro Tyr Ile Thr Asn Arg Thr Phe Met Leu Ala Lys Glu Ala Ser Leu
50                  55                  60                  65

gct gat aac aac aca gac gtt cgt ctc att ggg gag aaa ctg ttc cac      296
Ala Asp Asn Asn Thr Asp Val Arg Leu Ile Gly Glu Lys Leu Phe His
                70                  75                  80

gga gtc agt atg agt gag cgc tgc tat ctg atg aag cag gtg ctg aac      344
Gly Val Ser Met Ser Glu Arg Cys Tyr Leu Met Lys Gln Val Leu Asn
            85                  90                  95

ttc acc ctt gaa gaa gtg ctg ttc cct caa tct gat agg ttc cag cct      392
Phe Thr Leu Glu Glu Val Leu Phe Pro Gln Ser Asp Arg Phe Gln Pro
        100                 105                 110

tat atg cag gag gtg gtg ccc ttc ctg gcc agg ctc agc aac agg cta      440
Tyr Met Gln Glu Val Val Pro Phe Leu Ala Arg Leu Ser Asn Arg Leu
    115                 120                 125
```

```
agc aca tgt cat att gaa ggt gat gac ctg cat atc cag agg aat gtg      488
Ser Thr Cys His Ile Glu Gly Asp Asp Leu His Ile Gln Arg Asn Val
130                 135                 140                 145

caa aag ctg aag gac aca gtg aaa aag ctt gga gag agt gga gag atc      536
Gln Lys Leu Lys Asp Thr Val Lys Lys Leu Gly Glu Ser Gly Glu Ile
                150                 155                 160

aaa gca att gga gaa ctg gat ttg ctg ttt atg tct ctg aga aat gcc      584
Lys Ala Ile Gly Glu Leu Asp Leu Leu Phe Met Ser Leu Arg Asn Ala
            165                 170                 175

tgc att tga ccagagcaaa gctgaaaaat gaataactaa cccccttcc              633
Cys Ile

ctgctagaaa taacaattag atgccccaaa gcgatttttt ttaaccaaaa ggaagatggg    693

aagccaaact ccatcatgat gggtggattc caaatgaacc cctgcgttag ttacaaagga    753

aaccaatgcc acttttgttt ataagaccag aaggtagact ttctaagcat agatatttat    813

tgataacatt tcattgtaac tggtgttcta tacacagaaa acaatttatt ttttaaataa    873

ttgtcttttt ccataaaaaa gattactttc cattccttta ggggaaaaaa cccctaaata    933

gcttcatgtt tccataatca gtactttata tttataaatg tatttattat tattataaga    993

ctgcatttta tttatatcat tttattaata tggatttatt tatagaaaca tcattcgata   1053

ttgctacttg agtgtaaggc taatattgat atttatgaca ataattatag agctataaca   1113

tgtttatttg acctcaataa acacttggat atcc                               1147


<210> SEQ ID NO 11
<211> LENGTH: 179
<212> TYPE: PRT
<213> ORGANISM: Homo sapiens

<400> SEQUENCE: 11

Met Ala Ala Leu Gln Lys Ser Val Ser Ser Phe Leu Met Gly Thr Leu
1               5                   10                  15

Ala Thr Ser Cys Leu Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
    130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile


<210> SEQ ID NO 12
```

-continued

<211> LENGTH: 1049
<212> TYPE: DNA
<213> ORGANISM: Homo sapiens
<220> FEATURE:
<221> NAME/KEY: CDS
<222> LOCATION: (167)..(736)

<400> SEQUENCE: 12

```
aaaacaacag gaagcagctt acaaactcgg tgaacaactg agggaaccaa accagagacg      60

cgctgaacag agagaatcag gctcaaagca agtggaagtg ggcagagatt ccaccaggac     120

tggtgcaagg cgcagagcca gccagatttg agaagaaggc aaaaag atg ctg ggg        175
                                                   Met Leu Gly
                                                   1

agc aga gct gta atg ctg ctg ttg ctg ctg ccc tgg aca gct cag ggc       223
Ser Arg Ala Val Met Leu Leu Leu Leu Leu Pro Trp Thr Ala Gln Gly
    5                   10                  15

aga gct gtg cct ggg ggc agc agc cct gcc tgg act cag tgc cag cag       271
Arg Ala Val Pro Gly Gly Ser Ser Pro Ala Trp Thr Gln Cys Gln Gln
20                  25                  30                  35

ctt tca cag aag ctc tgc aca ctg gcc tgg agt gca cat cca cta gtg       319
Leu Ser Gln Lys Leu Cys Thr Leu Ala Trp Ser Ala His Pro Leu Val
                40                  45                  50

gga cac atg gat cta aga gaa gag gga gat gaa gag act aca aat gat       367
Gly His Met Asp Leu Arg Glu Glu Gly Asp Glu Glu Thr Thr Asn Asp
            55                  60                  65

gtt ccc cat atc cag tgt gga gat ggc tgt gac ccc caa gga ctc agg       415
Val Pro His Ile Gln Cys Gly Asp Gly Cys Asp Pro Gln Gly Leu Arg
        70                  75                  80

gac aac agt cag ttc tgc ttg caa agg atc cac cag ggt ctg att ttt       463
Asp Asn Ser Gln Phe Cys Leu Gln Arg Ile His Gln Gly Leu Ile Phe
    85                  90                  95

tat gag aag ctg cta gga tcg gat att ttc aca ggg gag cct tct ctg       511
Tyr Glu Lys Leu Leu Gly Ser Asp Ile Phe Thr Gly Glu Pro Ser Leu
100                 105                 110                 115

ctc cct gat agc cct gtg ggc cag ctt cat gcc tcc cta ctg ggc ctc       559
Leu Pro Asp Ser Pro Val Gly Gln Leu His Ala Ser Leu Leu Gly Leu
                120                 125                 130

agc caa ctc ctg cag cct gag ggt cac cac tgg gag act cag cag att       607
Ser Gln Leu Leu Gln Pro Glu Gly His His Trp Glu Thr Gln Gln Ile
            135                 140                 145

cca agc ctc agt ccc agc cag cca tgg cag cgt ctc ctt ctc cgc ttc       655
Pro Ser Leu Ser Pro Ser Gln Pro Trp Gln Arg Leu Leu Leu Arg Phe
        150                 155                 160

aaa atc ctt cgc agc ctc cag gcc ttt gtg gct gta gcc gcc cgg gtc       703
Lys Ile Leu Arg Ser Leu Gln Ala Phe Val Ala Val Ala Ala Arg Val
    165                 170                 175

ttt gcc cat gga gca gca acc ctg agt ccc taa aggcagcagc tcaaggatgg     756
Phe Ala His Gly Ala Ala Thr Leu Ser Pro
180                 185

cactcagatc tccatggccc agcaaggcca agataaatct accaccccag gcacctgtga     816

gccaacaggt taattagtcc attaatttta gtgggacctg catatgttga aaattaccaa     876

tactgactga catgtgatgc tgacctatga taaggttgag tatttattag atgggaaggg     936

aaatttgggg attatttatc ctcctgggga cagtttgggg aggattattt attgtattta     996

tattgaatta tgtacttttt tcaataaagt cttatttttg tggctaaaaa aaa           1049
```

<210> SEQ ID NO 13
<211> LENGTH: 189
<212> TYPE: PRT

```
<213> ORGANISM: Homo sapiens

<400> SEQUENCE: 13

Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185


<210> SEQ ID NO 14
<211> LENGTH: 2347
<212> TYPE: DNA
<213> ORGANISM: Homo sapiens
<220> FEATURE:
<221> NAME/KEY: CDS
<222> LOCATION: (43)..(1029)

<400> SEQUENCE: 14

ctgtttcagg gccattggac tctccgtcct gcccagagca ag atg tgt cac cag        54
                                               Met Cys His Gln
                                               1

cag ttg gtc atc tct tgg ttt tcc ctg gtt ttt ctg gca tct ccc ctc      102
Gln Leu Val Ile Ser Trp Phe Ser Leu Val Phe Leu Ala Ser Pro Leu
5                   10                  15                  20

gtg gcc ata tgg gaa ctg aag aaa gat gtt tat gtc gta gaa ttg gat      150
Val Ala Ile Trp Glu Leu Lys Lys Asp Val Tyr Val Val Glu Leu Asp
                25                  30                  35

tgg tat ccg gat gcc cct gga gaa atg gtg gtc ctc acc tgt gac acc      198
Trp Tyr Pro Asp Ala Pro Gly Glu Met Val Val Leu Thr Cys Asp Thr
            40                  45                  50

cct gaa gaa gat ggt atc acc tgg acc ttg gac cag agc agt gag gtc      246
Pro Glu Glu Asp Gly Ile Thr Trp Thr Leu Asp Gln Ser Ser Glu Val
        55                  60                  65

tta ggc tct ggc aaa acc ctg acc atc caa gtc aaa gag ttt gga gat      294
Leu Gly Ser Gly Lys Thr Leu Thr Ile Gln Val Lys Glu Phe Gly Asp
    70                  75                  80

gct ggc cag tac acc tgt cac aaa gga ggc gag gtt cta agc cat tcg      342
Ala Gly Gln Tyr Thr Cys His Lys Gly Gly Glu Val Leu Ser His Ser
85                  90                  95                  100
```

-continued

```
ctc ctg ctg ctt cac aaa aag gaa gat gga att tgg tcc act gat att      390
Leu Leu Leu Leu His Lys Lys Glu Asp Gly Ile Trp Ser Thr Asp Ile
                105                 110                 115

tta aag gac cag aaa gaa ccc aaa aat aag acc ttt cta aga tgc gag      438
Leu Lys Asp Gln Lys Glu Pro Lys Asn Lys Thr Phe Leu Arg Cys Glu
            120                 125                 130

gcc aag aat tat tct gga cgt ttc acc tgc tgg tgg ctg acg aca atc      486
Ala Lys Asn Tyr Ser Gly Arg Phe Thr Cys Trp Trp Leu Thr Thr Ile
        135                 140                 145

agt act gat ttg aca ttc agt gtc aaa agc agc aga ggc tct tct gac      534
Ser Thr Asp Leu Thr Phe Ser Val Lys Ser Ser Arg Gly Ser Ser Asp
    150                 155                 160

ccc caa ggg gtg acg tgc gga gct gct aca ctc tct gca gag aga gtc      582
Pro Gln Gly Val Thr Cys Gly Ala Ala Thr Leu Ser Ala Glu Arg Val
165                 170                 175                 180

aga ggg gac aac aag gag tat gag tac tca gtg gag tgc cag gag gac      630
Arg Gly Asp Asn Lys Glu Tyr Glu Tyr Ser Val Glu Cys Gln Glu Asp
                185                 190                 195

agt gcc tgc cca gct gct gag gag agt ctg ccc att gag gtc atg gtg      678
Ser Ala Cys Pro Ala Ala Glu Glu Ser Leu Pro Ile Glu Val Met Val
            200                 205                 210

gat gcc gtt cac aag ctc aag tat gaa aac tac acc agc agc ttc ttc      726
Asp Ala Val His Lys Leu Lys Tyr Glu Asn Tyr Thr Ser Ser Phe Phe
        215                 220                 225

atc agg gac atc atc aaa cct gac cca ccc aag aac ttg cag ctg aag      774
Ile Arg Asp Ile Ile Lys Pro Asp Pro Pro Lys Asn Leu Gln Leu Lys
    230                 235                 240

cca tta aag aat tct cgg cag gtg gag gtc agc tgg gag tac cct gac      822
Pro Leu Lys Asn Ser Arg Gln Val Glu Val Ser Trp Glu Tyr Pro Asp
245                 250                 255                 260

acc tgg agt act cca cat tcc tac ttc tcc ctg aca ttc tgc gtt cag      870
Thr Trp Ser Thr Pro His Ser Tyr Phe Ser Leu Thr Phe Cys Val Gln
                265                 270                 275

gtc cag ggc aag agc aag aga gaa aag aaa gat aga gtc ttc acg gac      918
Val Gln Gly Lys Ser Lys Arg Glu Lys Lys Asp Arg Val Phe Thr Asp
            280                 285                 290

aag acc tca gcc acg gtc atc tgc cgc aaa aat gcc agc att agc gtg      966
Lys Thr Ser Ala Thr Val Ile Cys Arg Lys Asn Ala Ser Ile Ser Val
        295                 300                 305

cgg gcc cag gac cgc tac tat agc tca tct tgg agc gaa tgg gca tct     1014
Arg Ala Gln Asp Arg Tyr Tyr Ser Ser Ser Trp Ser Glu Trp Ala Ser
    310                 315                 320

gtg ccc tgc agt tag gttctgatcc aggatgaaaa tttggaggaa aagtggaaga     1069
Val Pro Cys Ser
325

tattaagcaa aatgtttaaa gacacaacgg aatagaccca aaaagataat ttctatctga   1129

tttgctttaa aacgtttttt taggatcaca atgatatctt tgctgtattt gtatagttag   1189

atgctaaatg ctcattgaaa caatcagcta atttatgtat agattttcca gctctcaagt   1249

tgccatgggc cttcatgcta tttaaatatt taagtaattt atgtatttat tagtatatta   1309

ctgttattta acgtttgtct gccaggatgt atggaatgtt tcatactctt atgacctgat   1369

ccatcaggat cagtccctat tatgcaaaat gtgaatttaa ttttatttgt actgacaact   1429

tttcaagcaa ggctgcaagt acatcagttt tatgacaatc aggaagaatg cagtgttctg   1489

ataccagtgc catcatacac ttgtgatgga tgggaacgca agagatactt acatggaaac   1549

ctgacaatgc aaacctgttg agaagatcca ggagaacaag atgctagttc ccatgtctgt   1609

gaagacttcc tggagatggt gttgataaag caatttaggg ccacttacac ttctaagcaa   1669
```

```
gtttaatctt tggatgcctg aattttaaaa gggctagaaa aaaatgattg accagcctgg   1729

gaaacataac aagaccccgt ctctacaaaa aaaatttaaa attagccagg cgtggtggct   1789

catgcttgtg gtcccagctg ttcaggagga tgaggcagga ggatctcttg agcccaggag   1849

gtcaaggcta tggtgagccg tgattgtgcc actgcatacc agcctaggtg acagaatgag   1909

accctgtctc aaaaaaaaaa atgattgaaa ttaaaattca gctttagctt ccatggcagt   1969

cctcaccccc acctctctaa aagacacagg aggatgacac agaaacaccg taagtgtctg   2029

gaaggcaaaa agatcttaag attcaagaga gaggacaagt agttatggct aaggacatga   2089

aattgtcaga atggcaggtg gcttcttaac agccctgtga gaagcagaca gatgcaaaga   2149

aaatctggaa tccctttctc attagcatga atgaacctga tacacaatta tgaccagaaa   2209

atatggctcc atgaaggtgc tacttttaag taatgtatgt gcgctctgta aagtgattac   2269

atttgtttcc tgtttgttta tttatttatt tatttttgca ttctgaggct gaactaataa   2329

aaactcttct ttgtaatc                                                 2347


<210> SEQ ID NO 15
<211> LENGTH: 328
<212> TYPE: PRT
<213> ORGANISM: Homo sapiens

<400> SEQUENCE: 15

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
```

```
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325


<210> SEQ ID NO 16
<211> LENGTH: 1387
<212> TYPE: DNA
<213> ORGANISM: Homo sapiens
<220> FEATURE:
<221> NAME/KEY: CDS
<222> LOCATION: (311)..(844)

<400> SEQUENCE: 16

ctcaagtcac tccctaaaaa gacagtggaa ataaatttga ataaacaaaa caggcttgct      60

gaaaataaaa tcaggactcc taacctgctc cagtcagcct gcttccacga ggcctgtcag     120

tcagtgcccc acttgtgact gagtgtgcag tgcccagcat gtaccaggtc agtgcagagg     180

gctgcctgag ggctgtgctg agagggagag gagcagagat gctgctgagg gtggagggag     240

gccaagctgc caggtttggg gctgggggcc aagtggagtg agaaactggg atcccagggg     300

gagggtgcag atg agg gag cga ccc aga tta ggt gag gac agt tct ctc       349
           Met Arg Glu Arg Pro Arg Leu Gly Glu Asp Ser Ser Leu
           1               5                   10

att agc ctt ttc cta cag gtg gtt gca ttc ttg gca atg gtc atg gga      397
Ile Ser Leu Phe Leu Gln Val Val Ala Phe Leu Ala Met Val Met Gly
    15                  20                  25

acc cac acc tac agc cac tgg ccc agc tgc tgc ccc agc aaa ggg cag      445
Thr His Thr Tyr Ser His Trp Pro Ser Cys Cys Pro Ser Lys Gly Gln
30                  35                  40                  45

gac acc tct gag gag ctg ctg agg tgg agc act gtg cct gtg cct ccc      493
Asp Thr Ser Glu Glu Leu Leu Arg Trp Ser Thr Val Pro Val Pro Pro
                50                  55                  60

cta gag cct gct agg ccc aac cgc cac cca gag tcc tgt agg gcc agt      541
Leu Glu Pro Ala Arg Pro Asn Arg His Pro Glu Ser Cys Arg Ala Ser
            65                  70                  75

gaa gat gga ccc ctc aac agc agg gcc atc tcc ccc tgg aga tat gag      589
Glu Asp Gly Pro Leu Asn Ser Arg Ala Ile Ser Pro Trp Arg Tyr Glu
        80                  85                  90

ttg gac aga gac ttg aac cgg ctc ccc cag gac ctg tac cac gcc cgt      637
Leu Asp Arg Asp Leu Asn Arg Leu Pro Gln Asp Leu Tyr His Ala Arg
    95                  100                 105

tgc ctg tgc ccg cac tgc gtc agc cta cag aca ggc tcc cac atg gac      685
Cys Leu Cys Pro His Cys Val Ser Leu Gln Thr Gly Ser His Met Asp
110                 115                 120                 125

ccc cgg ggc aac tcg gag ctg ctc tac cac aac cag act gtc ttc tac      733
Pro Arg Gly Asn Ser Glu Leu Leu Tyr His Asn Gln Thr Val Phe Tyr
                130                 135                 140

cgg cgg cca tgc cat ggc gag aag ggc acc cac aag ggc tac tgc ctg      781
Arg Arg Pro Cys His Gly Glu Lys Gly Thr His Lys Gly Tyr Cys Leu
            145                 150                 155

gag cgc agg ctg tac cgt gtt tcc tta gct tgt gtg tgt gtg cgg ccc      829
```

```
Glu Arg Arg Leu Tyr Arg Val Ser Leu Ala Cys Val Cys Val Arg Pro
        160                 165                 170

cgt gtg atg ggc tag ccggacctgc tggaggctgg tcccttttg ggaaacctgg      884
Arg Val Met Gly
    175

agccaggtgt acaaccactt gccatgaagg gccaggatgc ccagatgctt ggcccctgtg    944

aagtgctgtc tggagcagca ggatcccggg acaggatggg gggctttggg gaaagcctgc   1004

acttctgcac attttgaaaa gagcagctgc tgcttagggc cgccggaagc tggtgtcctg   1064

tcattttctc tcaggaaagg ttttcaaagt tctgcccatt tctggaggcc accactcctg   1124

tctcttcctc ttttcccatc ccctgctacc ctggcccagc acaggcactt tctagatatt   1184

tccccccttgc tggagaagaa agagcccctg gttttatttg tttgtttact catcactcag  1244

tgagcatcta ctttgggtgc attctagtgt agttactagt cttttgacat ggatgattct   1304

gaggaggaag ctgttattga atgtatagag atttatccaa ataaatatct ttatttaaaa   1364

atgaaaaaaa aaaaaaaaaa aaa                                           1387


<210> SEQ ID NO 17
<211> LENGTH: 177
<212> TYPE: PRT
<213> ORGANISM: Homo sapiens

<400> SEQUENCE: 17

Met Arg Glu Arg Pro Arg Leu Gly Glu Asp Ser Ser Leu Ile Ser Leu
1               5                   10                  15

Phe Leu Gln Val Val Ala Phe Leu Ala Met Val Met Gly Thr His Thr
            20                  25                  30

Tyr Ser His Trp Pro Ser Cys Cys Pro Ser Lys Gly Gln Asp Thr Ser
        35                  40                  45

Glu Glu Leu Leu Arg Trp Ser Thr Val Pro Val Pro Pro Leu Glu Pro
    50                  55                  60

Ala Arg Pro Asn Arg His Pro Glu Ser Cys Arg Ala Ser Glu Asp Gly
65                  70                  75                  80

Pro Leu Asn Ser Arg Ala Ile Ser Pro Trp Arg Tyr Glu Leu Asp Arg
                85                  90                  95

Asp Leu Asn Arg Leu Pro Gln Asp Leu Tyr His Ala Arg Cys Leu Cys
            100                 105                 110

Pro His Cys Val Ser Leu Gln Thr Gly Ser His Met Asp Pro Arg Gly
        115                 120                 125

Asn Ser Glu Leu Leu Tyr His Asn Gln Thr Val Phe Tyr Arg Arg Pro
    130                 135                 140

Cys His Gly Glu Lys Gly Thr His Lys Gly Tyr Cys Leu Glu Arg Arg
145                 150                 155                 160

Leu Tyr Arg Val Ser Leu Ala Cys Val Cys Val Arg Pro Arg Val Met
                165                 170                 175

Gly


<210> SEQ ID NO 18
<211> LENGTH: 1044
<212> TYPE: DNA
<213> ORGANISM: Homo sapiens
<220> FEATURE:
<221> NAME/KEY: CDS
<222> LOCATION: (24)..(755)

<400> SEQUENCE: 18
```

-continued gaccaaagag gctgggcccc gcc atg ggc cag acg gca ggc gac ctt ggc tgg 53
Met Gly Gln Thr Ala Gly Asp Leu Gly Trp
1 5 10 cgg ctc agc ctg ttg ctg ctt ccc ttg ctc ctg gtt caa gct ggt gtc 101
Arg Leu Ser Leu Leu Leu Leu Pro Leu Leu Leu Val Gln Ala Gly Val
15 20 25 tgg gga ttc cca agg ccc cca ggg agg ccc cag ctg agc ctg cag gag 149
Trp Gly Phe Pro Arg Pro Pro Gly Arg Pro Gln Leu Ser Leu Gln Glu
30 35 40 ctg cgg agg gag ttc aca gtc agc ctg cat ctc gcc agg aag ctg ctc 197
Leu Arg Arg Glu Phe Thr Val Ser Leu His Leu Ala Arg Lys Leu Leu
45 50 55 tcc gag gtt cgg ggc cag gcc cac cgc ttt gcg gaa tct cac ctg cca 245
Ser Glu Val Arg Gly Gln Ala His Arg Phe Ala Glu Ser His Leu Pro
60 65 70 gga gtg aac ctg tac ctc ctg ccc ctg gga gag cag ctc cct gat gtt 293
Gly Val Asn Leu Tyr Leu Leu Pro Leu Gly Glu Gln Leu Pro Asp Val
75 80 85 90 tcc ctg acc ttc cag gcc tgg cgc cgc ctc tct gac ccg gag cgt ctc 341
Ser Leu Thr Phe Gln Ala Trp Arg Arg Leu Ser Asp Pro Glu Arg Leu
95 100 105 tgc ttc atc tcc acc acg ctt cag ccc ttc cat gcc ctg ctg gga ggg 389
Cys Phe Ile Ser Thr Thr Leu Gln Pro Phe His Ala Leu Leu Gly Gly
110 115 120 ctg ggg acc cag ggc cgc tgg acc aac atg gag agg atg cag ctg tgg 437
Leu Gly Thr Gln Gly Arg Trp Thr Asn Met Glu Arg Met Gln Leu Trp
125 130 135 gcc atg agg ctg gac ctc cgc gat ctg cag cgg cac ctc cgc ttc cag 485
Ala Met Arg Leu Asp Leu Arg Asp Leu Gln Arg His Leu Arg Phe Gln
140 145 150 gtg ctg gct gca gga ttc aac ctc ccg gag gag gag gag gag gaa gag 533
Val Leu Ala Ala Gly Phe Asn Leu Pro Glu Glu Glu Glu Glu Glu Glu
155 160 165 170 gag gag gag gag gag gag agg aag ggg ctg ctc cca ggg gca ctg ggc 581
Glu Glu Glu Glu Glu Glu Arg Lys Gly Leu Leu Pro Gly Ala Leu Gly
175 180 185 agc gcc tta cag ggc ccg gcc cag gtg tcc tgg ccc cag ctc ctc tcc 629
Ser Ala Leu Gln Gly Pro Ala Gln Val Ser Trp Pro Gln Leu Leu Ser
190 195 200 acc tac cgc ctg ctg cac tcc ttg gag ctc gtc tta tct cgg gcc gtg 677
Thr Tyr Arg Leu Leu His Ser Leu Glu Leu Val Leu Ser Arg Ala Val
205 210 215 cgg gag ttg ctg ctg ctg tcc aag gct ggg cac tca gtc tgg ccc ttg 725
Arg Glu Leu Leu Leu Leu Ser Lys Ala Gly His Ser Val Trp Pro Leu
220 225 230 ggg ttc cca aca ttg agc ccc cag ccc tga tcggtggctt cttagccccc 775
Gly Phe Pro Thr Leu Ser Pro Gln Pro
235 240 tgccccccac cctttagaac tttaggactg gagtcttggc atcagggcag ccttcgcatc 835 atcagccttg gacaagggag ggctcttcca gccccctgcc ccaggctcta cccagtaact 895 gaaagcccct ctggtcctcg ccagctattt atttcttgga tatttattta ttgtttaggg 955 agatgatggt ttatttattg tcttggggcc cgatggtcct cctcgggcca agcccccatg 1015 ctgggtgccc aataaagcac tctcatcca 1044

<210> SEQ ID NO 19
<211> LENGTH: 243
<212> TYPE: PRT
<213> ORGANISM: Homo sapiens

<400> SEQUENCE: 19

```
Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
            20                  25                  30

Pro Gly Arg Pro Gln Leu Ser Leu Gln Glu Leu Arg Arg Glu Phe Thr
        35                  40                  45

Val Ser Leu His Leu Ala Arg Lys Leu Leu Ser Glu Val Arg Gly Gln
    50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
    130                 135                 140

Arg Asp Leu Gln Arg His Leu Arg Phe Gln Val Leu Ala Ala Gly Phe
145                 150                 155                 160

Asn Leu Pro Glu Glu Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
            180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
    210                 215                 220

Ser Lys Ala Gly His Ser Val Trp Pro Leu Gly Phe Pro Thr Leu Ser
225                 230                 235                 240

Pro Gln Pro
```

<210> SEQ ID NO 20
<211> LENGTH: 1498
<212> TYPE: DNA
<213> ORGANISM: Homo sapiens
<220> FEATURE:
<221> NAME/KEY: CDS
<222> LOCATION: (88)..(897)

<400> SEQUENCE: 20

```
accaaacctc ttcgaggcac aaggcacaac aggctgctct gggattctct tcagccaatc      60

ttcattgctc aagtgtctga agcagcc atg gca gaa gta cct gag ctc gcc agt    114
                              Met Ala Glu Val Pro Glu Leu Ala Ser
                              1               5

gaa atg atg gct tat tac agt ggc aat gag gat gac ttg ttc ttt gaa      162
Glu Met Met Ala Tyr Tyr Ser Gly Asn Glu Asp Asp Leu Phe Phe Glu
10                  15                  20                  25

gct gat ggc cct aaa cag atg aag tgc tcc ttc cag gac ctg gac ctc      210
Ala Asp Gly Pro Lys Gln Met Lys Cys Ser Phe Gln Asp Leu Asp Leu
                30                  35                  40

tgc cct ctg gat ggc ggc atc cag cta cga atc tcc gac cac cac tac      258
Cys Pro Leu Asp Gly Gly Ile Gln Leu Arg Ile Ser Asp His His Tyr
            45                  50                  55
```

-continued

```
agc aag ggc ttc agg cag gcc gcg tca gtt gtt gtg gcc atg gac aag      306
Ser Lys Gly Phe Arg Gln Ala Ala Ser Val Val Val Ala Met Asp Lys
        60                  65                  70

ctg agg aag atg ctg gtt ccc tgc cca cag acc ttc cag gag aat gac      354
Leu Arg Lys Met Leu Val Pro Cys Pro Gln Thr Phe Gln Glu Asn Asp
    75                  80                  85

ctg agc acc ttc ttt ccc ttc atc ttt gaa gaa gaa cct atc ttc ttc      402
Leu Ser Thr Phe Phe Pro Phe Ile Phe Glu Glu Glu Pro Ile Phe Phe
90                  95                  100                 105

gac aca tgg gat aac gag gct tat gtg cac gat gca cct gta cga tca      450
Asp Thr Trp Asp Asn Glu Ala Tyr Val His Asp Ala Pro Val Arg Ser
                110                 115                 120

ctg aac tgc acg ctc cgg gac tca cag caa aaa agc ttg gtg atg tct      498
Leu Asn Cys Thr Leu Arg Asp Ser Gln Gln Lys Ser Leu Val Met Ser
            125                 130                 135

ggt cca tat gaa ctg aaa gct ctc cac ctc cag gga cag gat atg gag      546
Gly Pro Tyr Glu Leu Lys Ala Leu His Leu Gln Gly Gln Asp Met Glu
        140                 145                 150

caa caa gtg gtg ttc tcc atg tcc ttt gta caa gga gaa gaa agt aat      594
Gln Gln Val Val Phe Ser Met Ser Phe Val Gln Gly Glu Glu Ser Asn
    155                 160                 165

gac aaa ata cct gtg gcc ttg ggc ctc aag gaa aag aat ctg tac ctg      642
Asp Lys Ile Pro Val Ala Leu Gly Leu Lys Glu Lys Asn Leu Tyr Leu
170                 175                 180                 185

tcc tgc gtg ttg aaa gat gat aag ccc act cta cag ctg gag agt gta      690
Ser Cys Val Leu Lys Asp Asp Lys Pro Thr Leu Gln Leu Glu Ser Val
                190                 195                 200

gat ccc aaa aat tac cca aag aag aag atg gaa aag cga ttt gtc ttc      738
Asp Pro Lys Asn Tyr Pro Lys Lys Lys Met Glu Lys Arg Phe Val Phe
            205                 210                 215

aac aag ata gaa atc aat aac aag ctg gaa ttt gag tct gcc cag ttc      786
Asn Lys Ile Glu Ile Asn Asn Lys Leu Glu Phe Glu Ser Ala Gln Phe
        220                 225                 230

ccc aac tgg tac atc agc acc tct caa gca gaa aac atg ccc gtc ttc      834
Pro Asn Trp Tyr Ile Ser Thr Ser Gln Ala Glu Asn Met Pro Val Phe
    235                 240                 245

ctg gga ggg acc aaa ggc ggc cag gat ata act gac ttc acc atg caa      882
Leu Gly Gly Thr Lys Gly Gly Gln Asp Ile Thr Asp Phe Thr Met Gln
250                 255                 260                 265

ttt gtg tct tcc taa agagagctgt acccagagag tcctgtgctg aatgtggact      937
Phe Val Ser Ser

caatccctag ggctggcaga aagggaacag aaaggttttt gagtacggct atagcctgga    997

ctttcctgtt gtctacacca atgcccaact gcctgcctta gggtagtgct aagaggatct   1057

cctgtccatc agccaggaca gtcagctctc tcctttcagg gccaatcccc agcccttttg   1117

ttgagccagg cctctctcac ctctcctact cacttaaagc ccgcctgaca gaaaccacgg   1177

ccacatttgg ttctaagaaa ccctctgtca ttcgctccca cattctgatg agcaaccgct   1237

tccctattta tttatttatt tgtttgtttg ttttattcat tggtctaatt tattcaaagg   1297

gggcaagaag tagcagtgtc tgtaaaagag cctagttttt aatagctatg gaatcaattc   1357

aatttggact ggtgtgctct ctttaaatca agtcctttaa ttaagactga aaatatataa   1417

gctcagatta tttaaatggg aatatttata aatgagcaaa tatcatactg ttcaatggtt   1477

ctgaaataaa cttcactgaa g                                             1498
```

<210> SEQ ID NO 21
<211> LENGTH: 269
<212> TYPE: PRT

```
<213> ORGANISM: Homo sapiens

<400> SEQUENCE: 21

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
    130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
    210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265


<210> SEQ ID NO 22
<211> LENGTH: 1444
<212> TYPE: DNA
<213> ORGANISM: Homo sapiens
<220> FEATURE:
<221> NAME/KEY: CDS
<222> LOCATION: (216)..(977)

<400> SEQUENCE: 22

tttcattttg ggccgagctg gaggcggcgg ggccgtcccg gaacggctgc ggccgggcac      60

cccgggagtt aatccgaaag cgccgcaagc cccgcgggcc ggccgcaccg cacgtgtcac     120

cgagaagctg atgtagagag agacacagaa ggagacagaa agcaagagac cagagtcccg     180

ggaaagtcct gccgcgcctc gggacaatta taaaa atg tgg ccc cct ggg tca        233
                                       Met Trp Pro Pro Gly Ser
                                       1               5

gcc tcc cag cca ccg ccc tca cct gcc gcg gcc aca ggt ctg cat cca       281
Ala Ser Gln Pro Pro Pro Ser Pro Ala Ala Ala Thr Gly Leu His Pro
            10                  15                  20
```

-continued

```
gcg gct cgc cct gtg tcc ctg cag tgc cgg ctc agc atg tgt cca gcg      329
Ala Ala Arg Pro Val Ser Leu Gln Cys Arg Leu Ser Met Cys Pro Ala
        25                  30                  35

cgc agc ctc ctc ctt gtg gct acc ctg gtc ctc ctg gac cac ctc agt      377
Arg Ser Leu Leu Leu Val Ala Thr Leu Val Leu Leu Asp His Leu Ser
    40                  45                  50

ttg gcc aga aac ctc ccc gtg gcc act cca gac cca gga atg ttc cca      425
Leu Ala Arg Asn Leu Pro Val Ala Thr Pro Asp Pro Gly Met Phe Pro
55                  60                  65                  70

tgc ctt cac cac tcc caa aac ctg ctg agg gcc gtc agc aac atg ctc      473
Cys Leu His His Ser Gln Asn Leu Leu Arg Ala Val Ser Asn Met Leu
                75                  80                  85

cag aag gcc aga caa act cta gaa ttt tac cct tgc act tct gaa gag      521
Gln Lys Ala Arg Gln Thr Leu Glu Phe Tyr Pro Cys Thr Ser Glu Glu
            90                  95                  100

att gat cat gaa gat atc aca aaa gat aaa acc agc aca gtg gag gcc      569
Ile Asp His Glu Asp Ile Thr Lys Asp Lys Thr Ser Thr Val Glu Ala
        105                 110                 115

tgt tta cca ttg gaa tta acc aag aat gag agt tgc cta aat tcc aga      617
Cys Leu Pro Leu Glu Leu Thr Lys Asn Glu Ser Cys Leu Asn Ser Arg
    120                 125                 130

gag acc tct ttc ata act aat ggg agt tgc ctg gcc tcc aga aag acc      665
Glu Thr Ser Phe Ile Thr Asn Gly Ser Cys Leu Ala Ser Arg Lys Thr
135                 140                 145                 150

tct ttt atg atg gcc ctg tgc ctt agt agt att tat gaa gac ttg aag      713
Ser Phe Met Met Ala Leu Cys Leu Ser Ser Ile Tyr Glu Asp Leu Lys
                155                 160                 165

atg tac cag gtg gag ttc aag acc atg aat gca aag ctt ctg atg gat      761
Met Tyr Gln Val Glu Phe Lys Thr Met Asn Ala Lys Leu Leu Met Asp
            170                 175                 180

cct aag agg cag atc ttt cta gat caa aac atg ctg gca gtt att gat      809
Pro Lys Arg Gln Ile Phe Leu Asp Gln Asn Met Leu Ala Val Ile Asp
        185                 190                 195

gag ctg atg cag gcc ctg aat ttc aac agt gag act gtg cca caa aaa      857
Glu Leu Met Gln Ala Leu Asn Phe Asn Ser Glu Thr Val Pro Gln Lys
    200                 205                 210

tcc tcc ctt gaa gaa ccg gat ttt tat aaa act aaa atc aag ctc tgc      905
Ser Ser Leu Glu Glu Pro Asp Phe Tyr Lys Thr Lys Ile Lys Leu Cys
215                 220                 225                 230

ata ctt ctt cat gct ttc aga att cgg gca gtg act att gat aga gtg      953
Ile Leu Leu His Ala Phe Arg Ile Arg Ala Val Thr Ile Asp Arg Val
                235                 240                 245

atg agc tat ctg aat gct tcc taa aaagcgaggt ccctccaaac cgttgtcatt    1007
Met Ser Tyr Leu Asn Ala Ser
            250

tttataaaac tttgaaatga ggaaactttg ataggatgtg gattaagaac tagggagggg   1067

gaaagaagga tgggactatt acatccacat gatacctctg atcaagtatt tttgacattt   1127

actgtggata aattgttttt aagttttcat gaatgaattg ctaagaaggg aaaatatcca   1187

tcctgaaggt gtttttcatt cactttaata gaagggcaaa tatttataag ctatttctgt   1247

accaaagtgt ttgtggaaac aaacatgtaa gcataactta ttttaaaata tttatttata   1307

taacttggta atcatgaaag catctgagct aacttatatt tatttatgtt atatttatta   1367

aattatttat caagtgtatt tgaaaaatat ttttaagtgt tctaaaaata aaagtattga   1427

attaaagtga aaaaaaa                                                  1444

<210> SEQ ID NO 23
```

<211> LENGTH: 253
<212> TYPE: PRT
<213> ORGANISM: Homo sapiens

<400> SEQUENCE: 23

Met Trp Pro Pro Gly Ser Ala Ser Gln Pro Pro Pro Ser Pro Ala Ala
1 5 10 15

Ala Thr Gly Leu His Pro Ala Ala Arg Pro Val Ser Leu Gln Cys Arg
20 25 30

Leu Ser Met Cys Pro Ala Arg Ser Leu Leu Leu Val Ala Thr Leu Val
35 40 45

Leu Leu Asp His Leu Ser Leu Ala Arg Asn Leu Pro Val Ala Thr Pro
50 55 60

Asp Pro Gly Met Phe Pro Cys Leu His His Ser Gln Asn Leu Leu Arg
65 70 75 80

Ala Val Ser Asn Met Leu Gln Lys Ala Arg Gln Thr Leu Glu Phe Tyr
85 90 95

Pro Cys Thr Ser Glu Glu Ile Asp His Glu Asp Ile Thr Lys Asp Lys
100 105 110

Thr Ser Thr Val Glu Ala Cys Leu Pro Leu Glu Leu Thr Lys Asn Glu
115 120 125

Ser Cys Leu Asn Ser Arg Glu Thr Ser Phe Ile Thr Asn Gly Ser Cys
130 135 140

Leu Ala Ser Arg Lys Thr Ser Phe Met Met Ala Leu Cys Leu Ser Ser
145 150 155 160

Ile Tyr Glu Asp Leu Lys Met Tyr Gln Val Glu Phe Lys Thr Met Asn
165 170 175

Ala Lys Leu Leu Met Asp Pro Lys Arg Gln Ile Phe Leu Asp Gln Asn
180 185 190

Met Leu Ala Val Ile Asp Glu Leu Met Gln Ala Leu Asn Phe Asn Ser
195 200 205

Glu Thr Val Pro Gln Lys Ser Ser Leu Glu Glu Pro Asp Phe Tyr Lys
210 215 220

Thr Lys Ile Lys Leu Cys Ile Leu Leu His Ala Phe Arg Ile Arg Ala
225 230 235 240

Val Thr Ile Asp Arg Val Met Ser Tyr Leu Asn Ala Ser
245 250

<210> SEQ ID NO 24
<211> LENGTH: 2217
<212> TYPE: DNA
<213> ORGANISM: Homo sapiens
<220> FEATURE:
<221> NAME/KEY: CDS
<222> LOCATION: (883)..(2055)

<400> SEQUENCE: 24
ccccgccgcc gccgcccttc gcgccctggg ccatctccct cccacctccc tccgcggagc 60
agccagacag cgagggcccc ggccgggggc aggggggacg ccccgtccgg ggcacccccc 120
cggctctgag ccgcccgcgg ggccggcctc ggcccggagc ggaggaagga gtcgccgagg 180
agcagcctga ggccccagag tctgagacga gccgccgccg cccccgccac tgcggggagg 240
agggggagga ggagcgggag gagggacgag ctggtcggga gaagaggaaa aaaacttttg 300
agacttttcc gttgccgctg ggagccggag gcgcggggac ctcttggcgc gacgctgccc 360
cgcgaggagg caggacttgg ggaccccaga ccgcctccct ttgccgccgg ggacgcttgc 420

-continued

```
tccctccctg ccccctacac ggcgtccctc aggcgccccc attccggacc agccctcggg    480

agtcgccgac ccggcctccc gcaaagactt ttccccagac ctcgggcgca ccccctgcac    540

gccgccttca tccccggcct gtctcctgag cccccgcgca tcctagaccc tttctcctcc    600

aggagacgga tctctctccg acctgccaca gatcccctat tcaagaccac ccaccttctg    660

gtaccagatc gcgcccatct aggttatttc cgtgggatac tgagacaccc ccggtccaag    720

cctcccctcc accactgcgc ccttctccct gaggacctca gctttccctc gaggccctcc    780

taccttttgc cgggagaccc ccagcccctg caggggcggg gcctccccac cacaccagcc    840

ctgttcgcgc tctcggcagt gccggggggc gccgcctccc cc atg ccg ccc tcc       894
                                               Met Pro Pro Ser
                                               1

ggg ctg cgg ctg ctg ccg ctg ctg cta ccg ctg ctg tgg cta ctg gtg      942
Gly Leu Arg Leu Leu Pro Leu Leu Leu Pro Leu Leu Trp Leu Leu Val
5                   10                  15                  20

ctg acg cct ggc cgg ccg gcc gcg gga cta tcc acc tgc aag act atc      990
Leu Thr Pro Gly Arg Pro Ala Ala Gly Leu Ser Thr Cys Lys Thr Ile
                25                  30                  35

gac atg gag ctg gtg aag cgg aag cgc atc gag gcc atc cgc ggc cag     1038
Asp Met Glu Leu Val Lys Arg Lys Arg Ile Glu Ala Ile Arg Gly Gln
            40                  45                  50

atc ctg tcc aag ctg cgg ctc gcc agc ccc ccg agc cag ggg gag gtg     1086
Ile Leu Ser Lys Leu Arg Leu Ala Ser Pro Pro Ser Gln Gly Glu Val
        55                  60                  65

ccg ccc ggc ccg ctg ccc gag gcc gtg ctc gcc ctg tac aac agc acc     1134
Pro Pro Gly Pro Leu Pro Glu Ala Val Leu Ala Leu Tyr Asn Ser Thr
    70                  75                  80

cgc gac cgg gtg gcc ggg gag agt gca gaa ccg gag ccc gag cct gag     1182
Arg Asp Arg Val Ala Gly Glu Ser Ala Glu Pro Glu Pro Glu Pro Glu
85                  90                  95                  100

gcc gac tac tac gcc aag gag gtc acc cgc gtg cta atg gtg gaa acc     1230
Ala Asp Tyr Tyr Ala Lys Glu Val Thr Arg Val Leu Met Val Glu Thr
                105                 110                 115

cac aac gaa atc tat gac aag ttc aag cag agt aca cac agc ata tat     1278
His Asn Glu Ile Tyr Asp Lys Phe Lys Gln Ser Thr His Ser Ile Tyr
            120                 125                 130

atg ttc ttc aac aca tca gag ctc cga gaa gcg gta cct gaa ccc gtg     1326
Met Phe Phe Asn Thr Ser Glu Leu Arg Glu Ala Val Pro Glu Pro Val
        135                 140                 145

ttg ctc tcc cgg gca gag ctg cgt ctg ctg agg ctc aag tta aaa gtg     1374
Leu Leu Ser Arg Ala Glu Leu Arg Leu Leu Arg Leu Lys Leu Lys Val
    150                 155                 160

gag cag cac gtg gag ctg tac cag aaa tac agc aac aat tcc tgg cga     1422
Glu Gln His Val Glu Leu Tyr Gln Lys Tyr Ser Asn Asn Ser Trp Arg
165                 170                 175                 180

tac ctc agc aac cgg ctg ctg gca ccc agc gac tcg cca gag tgg tta     1470
Tyr Leu Ser Asn Arg Leu Leu Ala Pro Ser Asp Ser Pro Glu Trp Leu
                185                 190                 195

tct ttt gat gtc acc gga gtt gtg cgg cag tgg ttg agc cgt gga ggg     1518
Ser Phe Asp Val Thr Gly Val Val Arg Gln Trp Leu Ser Arg Gly Gly
            200                 205                 210

gaa att gag ggc ttt cgc ctt agc gcc cac tgc tcc tgt gac agc agg     1566
Glu Ile Glu Gly Phe Arg Leu Ser Ala His Cys Ser Cys Asp Ser Arg
        215                 220                 225

gat aac aca ctg caa gtg gac atc aac ggg ttc act acc ggc cgc cga     1614
Asp Asn Thr Leu Gln Val Asp Ile Asn Gly Phe Thr Thr Gly Arg Arg
    230                 235                 240

ggt gac ctg gcc acc att cat ggc atg aac cgg cct ttc ctg ctt ctc     1662
```

-continued

```
Gly Asp Leu Ala Thr Ile His Gly Met Asn Arg Pro Phe Leu Leu Leu
245                 250                 255                 260

atg gcc acc ccg ctg gag agg gcc cag cat ctg caa agc tcc cgg cac     1710
Met Ala Thr Pro Leu Glu Arg Ala Gln His Leu Gln Ser Ser Arg His
                265                 270                 275

cgc cga gcc ctg gac acc aac tat tgc ttc agc tcc acg gag aag aac     1758
Arg Arg Ala Leu Asp Thr Asn Tyr Cys Phe Ser Ser Thr Glu Lys Asn
            280                 285                 290

tgc tgc gtg cgg cag ctg tac att gac ttc cgc aag gac ctc ggc tgg     1806
Cys Cys Val Arg Gln Leu Tyr Ile Asp Phe Arg Lys Asp Leu Gly Trp
        295                 300                 305

aag tgg atc cac gag ccc aag ggc tac cat gcc aac ttc tgc ctc ggg     1854
Lys Trp Ile His Glu Pro Lys Gly Tyr His Ala Asn Phe Cys Leu Gly
    310                 315                 320

ccc tgc ccc tac att tgg agc ctg gac acg cag tac agc aag gtc ctg     1902
Pro Cys Pro Tyr Ile Trp Ser Leu Asp Thr Gln Tyr Ser Lys Val Leu
325                 330                 335                 340

gcc ctg tac aac cag cat aac ccg ggc gcc tcg gcg gcg ccg tgc tgc     1950
Ala Leu Tyr Asn Gln His Asn Pro Gly Ala Ser Ala Ala Pro Cys Cys
                345                 350                 355

gtg ccg cag gcg ctg gag ccg ctg ccc atc gtg tac tac gtg ggc cgc     1998
Val Pro Gln Ala Leu Glu Pro Leu Pro Ile Val Tyr Tyr Val Gly Arg
            360                 365                 370

aag ccc aag gtg gag cag ctg tcc aac atg atc gtg cgc tcc tgc aag     2046
Lys Pro Lys Val Glu Gln Leu Ser Asn Met Ile Val Arg Ser Cys Lys
        375                 380                 385

tgc agc tga ggtcccgccc cgccccgccc cgccccggca ggcccggccc             2095
Cys Ser
    390

caccccgccc cgccccgct gccttgccca tgggggctgt atttaaggac acccgtgccc   2155

caagcccacc tggggcccca ttaaagatgg agagaggact gcggaaaaaa aaaaaaaaaa   2215

aa                                                                  2217


<210> SEQ ID NO 25
<211> LENGTH: 390
<212> TYPE: PRT
<213> ORGANISM: Homo sapiens

<400> SEQUENCE: 25

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110
```

-continued

```
Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390


<210> SEQ ID NO 26
<211> LENGTH: 8
<212> TYPE: PRT
<213> ORGANISM: Artificial
<220> FEATURE:
<223> OTHER INFORMATION: synthetic peptide

<400> SEQUENCE: 26

Ser Ile Ile Asn Phe Glu Lys Leu
1               5
```